(12) United States Patent
Buckley et al.

(10) Patent No.: US 8,093,238 B2
(45) Date of Patent: Jan. 10, 2012

(54) FUSED THIAZOLE DERIVATIVES AS KINASE INHIBITORS

(75) Inventors: George Martin Buckley, Slough (GB); Trevor Morgan, Slough (GB); Verity Margaret Sabin, Slough (GB)

(73) Assignee: UCB Pharma S.A., Brussels (BE)

( * ) Notice: Subject to any disclaimer, the term of this patent is extended or adjusted under 35 U.S.C. 154(b) by 222 days.

(21) Appl. No.: 12/445,056

(22) PCT Filed: Oct. 10, 2007

(86) PCT No.: PCT/GB2007/003853
§ 371 (c)(1),
(2), (4) Date: Nov. 30, 2009

(87) PCT Pub. No.: WO2008/044022
PCT Pub. Date: Apr. 17, 2008

(65) Prior Publication Data
US 2010/0069361 A1    Mar. 18, 2010

(30) Foreign Application Priority Data
Oct. 10, 2006  (GB) .................................. 0620059.6

(51) Int. Cl.
C07D 498/04 (2006.01)
C07D 513/04 (2006.01)
A61K 31/428 (2006.01)
A61K 31/429 (2006.01)

(52) U.S. Cl. .................................. 514/212.07; 540/503
(58) Field of Classification Search .................. 540/503; 514/212.07
See application file for complete search history.

(56) References Cited

U.S. PATENT DOCUMENTS
7,838,517 B2 *  11/2010  Knegtel et al. ........... 514/212.06

FOREIGN PATENT DOCUMENTS
| WO | WO2004078754 | 9/2004 |
| WO | WO2004096797 | 11/2004 |
| WO | WO2006051270 | 5/2006 |
| WO | WO2006114606 | 11/2006 |

OTHER PUBLICATIONS
International Search Report dated Feb. 6, 2008.
* cited by examiner

*Primary Examiner* — Kahsay T Habte
(74) *Attorney, Agent, or Firm* — McDonnell Boehnen Hulbert & Berghoff LLP

(57) ABSTRACT

A series of 5,5-dimethyl-5,6-dihydro-1,3-benzothiazol-7 (4H)-one and 7,7-dimethyl-5,6,7,8-tetrahydro-4H-[1,3]thiazolo[5,4-c]azepin-4-one derivatives, and analogues thereof, which are substituted in the 2-position by an optionally substituted benzofused morpholin-4-yl moiety, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions. Formula (I).

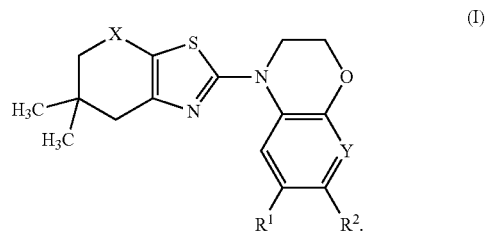

14 Claims, No Drawings

FUSED THIAZOLE DERIVATIVES AS KINASE INHIBITORS

This is a National Stage of International Application No. PCT/GB2007/003853, filed Oct. 10, 2007.

The present invention relates to a class of fused thiazole derivatives, and to their use in therapy. More particularly, the invention provides a family of 5,6-dihydro-1,3-benzothiazol-7(4H)-one derivatives, and analogues thereof, which are substituted in the 2-position by a 2,3-dihydrobenzo[1,4]oxazin-4-yl moiety, or an analogue thereof. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf S. Brader & S. A. Eccles, *Tumori*, 2004, 90, 2-8).

The compounds of the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds of the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

The specific compounds 2-(morpholin-4-yl)-5,6-dihydro-1,3-benzothiazol-7(4H)-one, 5,5-dimethyl-2-(morpholin-4-yl)-5,6-dihydro-1,3-benzothiazol-7(4H)-one, 2-(morpholin-4-yl)-5,6,7,8-tetrahydro-4H-[1,3]thiazolo[5,4-c]azepin-4-one and 7,7-dimethyl-2-(morpholin-4-yl)-5,6,7,8-tetrahydro-4H-[1,3]thiazolo[5,4-c]azepin-4-one are disclosed in *Russian Journal of General Chemistry* (translation of *Zhurnal Obshchei Khimii*), 2000, 70[5], 784-787; but no therapeutic utility is ascribed therein to those compounds.

Copending international patent application no. PCT/GB2006/001505, published on 2 Nov. 2006 as WO 2006/114606 A1 provides a series of 5,6-dihydro-1,3-benzothiazol-7(4H)-one derivatives, and analogues thereof, which are substituted in the 2-position by an optionally substituted morpholin-4-yl moiety; these compounds are stated to be selective inhibitors of PI3 kinase enzymes, and accordingly to be of benefit in medicine, for example in the treatment of inflammatory, autoimmune, cardiovascular, neurodegenerative, metabolic, oncological, nociceptive or ophthalmic conditions.

International patent application no. WO 2007/089034 discloses a class of benzoxazine and related nitrogen-containing heterobicyclic compounds as mineralcorticoid receptor modulating agents.

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I), or a pharmaceutically acceptable salt or solvate thereof:

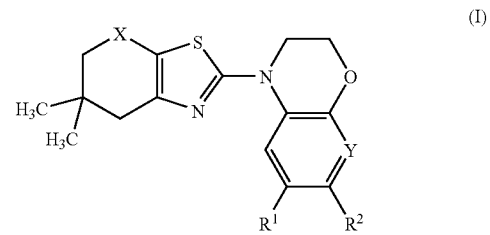

(I)

wherein

—X— represents a group of formula (a) or (b):

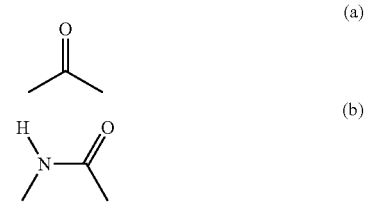

Y represents CH or N;

$R^1$ and $R^2$ independently represent hydrogen, halogen, nitro, hydroxy, $C_{1-6}$ alkyl, optionally substituted aryl, optionally substituted heteroaryl, —$NR^aR^b$, —$CONR^aR^b$, —$NR^a$-$COR^c$, —$N(COR^c)_2$, —$NR^aSO_2R^c$, —$CO_2R^d$ or —$OR^e$;

$R^a$ represents hydrogen, $C_{1-6}$ alkyl or heteroaryl; and $R^b$ represents hydrogen; or $C_{1-6}$ alkyl, aryl, $C_{3-7}$ heterocycloalkyl($C_{1-6}$)alkyl, heteroaryl or heteroaryl($C_{1-6}$)alkyl, any of which groups may be optionally substituted by one or more substituents; or $R^a$ and $R^b$, when taken together with the nitrogen atom to which they are both attached, represent optionally substituted $C_{3-7}$ heterocycloalkyl;

R$^c$ represents C$_{1-6}$alkyl, aryl or heteroaryl, any of which groups may be optionally substituted by one or more substituents;

R$^d$ represents C$_{1-6}$alkyl; and

R$^e$ represents optionally substituted heteroaryl;

provided that, when —X— represents a group of formula (a) as depicted above and R$^1$ and R$^2$ are both hydrogen, then Y represents N.

The compounds of the present invention are encompassed within the generic scope of copending international patent application no. WO 2006/114606 A1. There is, however, no actual disclosure in that application of any specific compound of formula (I) as defined above.

Where any group in the compounds of formula (I) above is referred to as being optionally substituted, this group may be unsubstituted, or substituted by one or more substituents. Typically, any such group will be unsubstituted, or substituted by one or two substitutents. Suitably, any such group will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes within its scope N-oxides of the compounds of formula (I) above.

Suitable alkyl groups which may be present on the compounds of the invention include straight-chained and branched C$_{1-6}$alkyl groups, for example C$_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "C$_{1-6}$alkoxy", "C$_{1-6}$alkylthio", "C$_{1-6}$alkylsulphonyl" and "C$_{1-6}$ alkylamino" are to be construed accordingly.

The expression "hydroxy(C$_{1-6}$)alkyl" refers to a C$_{1-6}$alkyl group, as defined above, substituted by one or more, typically one or two, hydroxy groups.

The expression "hydroxy(C$_{1-6}$)alkylamino" refers to a C$_{1-6}$ alkylamino group, substituted by one or more, typically one, hydroxy group.

The expression "hydroxy[(C$_{1-6}$)alkoxy](C$_{1-6}$)alkyl" refers to a C$_{1-6}$ alkyl group substituted by one or more, typically one, hydroxy group and one or more, typically one, C$_{1-6}$ alkoxy group.

The expression "C$_{1-6}$ alkoxy(C$_{2-6}$)alkenyl" refers to a C$_{2-6}$ alkenyl group, substituted by one or more, typically one, C$_{1-6}$ alkoxy group. Suitable examples of C$_{2-6}$ alkenyl groups include ethenyl and propenyl.

Suitable aryl groups include phenyl and naphthyl, preferably phenyl.

Suitable heterocycloalkyl groups, which may comprise benzo-fused analogues thereof, include azetidinyl, tetrahydrofuranyl, pyrrolidinyl, imidazolidinyl, tetrahydropyranyl, piperidinyl, 1,2,3,4-tetrahydroquinolinyl, 1,2,3,4-tetrahydroisoquinolinyl, piperazinyl, 1,2,3,4-tetrahydroquinoxalinyl, morpholinyl and thiomorpholinyl.

Suitable heteroaryl groups include furyl, benzofuryl, dibenzofuryl, thienyl, benzothienyl, pyrrolyl, indolyl, pyrrolo[2,3-b]pyridinyl, pyrazolyl, indazolyl, oxazolyl, isoxazolyl, thiazolyl, isothiazolyl, imidazolyl, benzimidazolyl, oxadiazolyl, thiadiazolyl, triazolyl, benzotriazolyl, tetrazolyl, pyridinyl, quinolinyl, isoquinolinyl, pyridazinyl, pyrimidinyl and pyrazinyl groups. Further suitable heteroaryl groups include imidazo[1,2-a]pyrazinyl and imidazo[1,2-a]pyrimidinyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)-enol (CH=CHOH) tautomers. Formula (I) and the formulae depicted hereinafter are intended to represent all individual tautomers and all possible mixtures thereof, unless stated or shown otherwise.

Specific sub-classes of compounds in accordance with the present invention are represented by the compounds of formula (IA), (IB), (IC) and (ID):

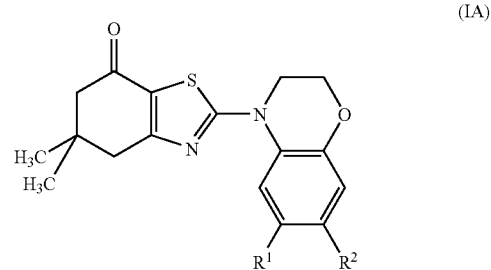

(IA)

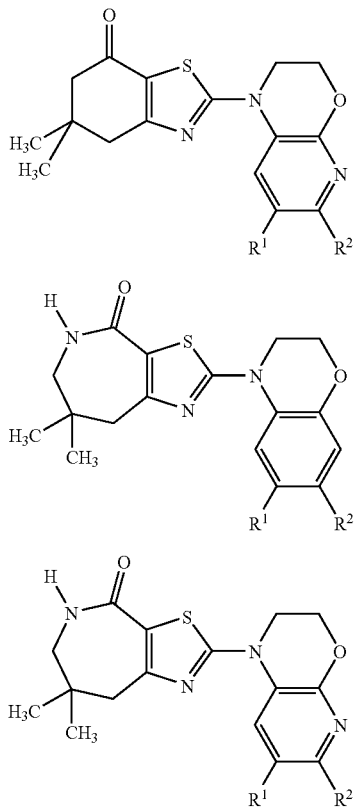

wherein $R^1$ and $R^2$ are as defined above.

Representative sub-classes of compounds in accordance with the present invention are represented by the compounds of formula (IA), (IB) and (IC) as depicted above.

In one embodiment, the present invention provides a compound of formula (IA) as depicted above, or a pharmaceutically acceptable salt or solvate thereof, wherein $R^1$ represents halogen, nitro, hydroxy, $C_{1-6}$ alkyl, optionally substituted aryl, optionally substituted heteroaryl, —$NR^aR^b$, —$CONR^aR^b$, —$NR^aCOR^c$, —$N(COR^c)_2$, —$NR^aSO_2R^c$, —$CO_2R^d$ or —$OR^e$;

$R^2$ represents hydrogen, halogen, nitro, hydroxy, $C_{1-6}$ alkyl, optionally substituted aryl, optionally substituted heteroaryl, —$NR^aR^b$, —$CONR^aR^b$, —$NR^aCOR^c$, —N$(COR^c)_2$, —$NR^aSO_2R^c$, —$CO_2R^d$ or —$OR^e$; and $R^a$, $R^b$, $R^c$, $R^d$ and $R^e$ are as defined above.

In another embodiment, the present invention provides a compound of formula (IA) as depicted above, or a pharmaceutically acceptable salt or solvate thereof, wherein $R^1$ represents halogen, nitro, hydroxy, optionally substituted aryl, optionally substituted heteroaryl, —$NR^aR^b$, —$CONR^aR^b$, —$NR^aCOR^c$, —$N(COR^c)_2$, —$NR^aSO_2R^c$ or —$CO_2R^d$;

$R^2$ represents hydrogen, halogen, nitro, hydroxy, optionally substituted aryl, optionally substituted heteroaryl, —$NR^aR^b$, —$CONR^aR^b$, —$NR^aCOR^c$, —$N(COR^c)_2$, —$NR^aSO_2R^c$ or —$CO_2R^d$; and $R^a$, $R^b$, $R^c$ and $R^d$ are as defined above.

In a further embodiment, the present invention provides a compound of formula (IA) as depicted above, or a pharmaceutically acceptable salt or solvate thereof, wherein $R^1$ represents hydrogen, halogen, nitro, hydroxy, $C_{1-6}$ alkyl, optionally substituted aryl, optionally substituted heteroaryl, —$NR^aR^b$, —$CONR^aR^b$, —$NR^aCOR^c$, —N$(COR^c)_2$, —$NR^aSO_2R^c$, —$CO_2R^d$ or —$OR^e$;

$R^2$ represents halogen, nitro, hydroxy, $C_{1-6}$ alkyl, optionally substituted aryl, optionally substituted heteroaryl, —$NR^aR^b$, —$CONR^aR^b$, —$NR^aCOR^c$, —$N(COR^c)_2$, $NR^aSO_2R^c$, —$CO_2R^d$ or —$OR^e$; and $R^a$, $R^b$, $R^c$, $R^d$ and $R^e$ are as defined above.

In an additional embodiment, the present invention provides a compound of formula (IA) as depicted above, or a pharmaceutically acceptable salt or solvate thereof, wherein $R^1$ represents hydrogen, halogen, nitro, hydroxy, optionally substituted aryl, optionally substituted heteroaryl, —$NR^aR^b$, —$CONR^aR^b$, —$NR^aCOR^c$, —$N(COR^c)_2$, —$NR^aSO_2R^c$ or —$CO_2R^d$;

$R^2$ represents halogen, nitro, hydroxy, optionally substituted aryl, optionally substituted heteroaryl, —$NR^aR^b$, —$CONR^aR^b$, —$NR^aCOR^c$, —$N(COR^c)_2$, —$NR^aSO_2R^c$ or —$CO_2R^d$; and $R^a$, $R^b$, $R^c$ and $R^d$ are as defined above.

In one embodiment, —X— represents a group of formula (a) as depicted above. In another embodiment, —X— represents a group of formula (b) as depicted above.

In one embodiment, Y represents CH. In another embodiment, Y represents N.

In one embodiment, $R^1$ and $R^2$ independently represent hydrogen, halogen, nitro, hydroxy, optionally substituted aryl, optionally substituted heteroaryl, —$NR^aR^b$, —$CONR^aR^b$, —$NR^aCOR^c$, —$N(COR^c)_2$, —$NR^aSO_2R^c$ or —$CO_2R^d$.

In another embodiment, $R^1$ and/or $R^2$ are other than —$NR^aSO_2R^c$.

In one embodiment, $R^1$ represents hydrogen and $R^2$ is other than hydrogen. In another embodiment, $R^2$ represents hydrogen and $R^1$ is other than hydrogen. In a further embodiment, $R^2$ represents methyl and $R^1$ is other than hydrogen.

Suitably, $R^a$ represents hydrogen or $C_{1-6}$ alkyl. In one embodiment, $R^a$ represents hydrogen. In another embodiment, $R^a$ represents $C_{1-6}$ alkyl. In a further embodiment, $R^a$ represents heteroaryl.

Particular values of $R^a$ include hydrogen, methyl and pyrazinyl.

The moiety $R^b$ typically represents hydrogen; or methyl, ethyl, phenyl, tetrahydrofuranylmethyl, piperidinylmethyl, morpholinylethyl, pyridinyl, pyrazinyl, pyrazolylmethyl, imidazolylmethyl or pyridinylmethyl, any of which groups may be optionally substituted by one or more substituents. The moiety $R^b$ also typically represents pyridazinyl optionally substituted by one or more substitutents.

Examples of typical substituents on $R^1$, $R^2$, $R^b$ or $R^c$, or on the cyclic moiety —$NR^aR^b$, include halogen, $C_{1-6}$ alkyl, $C_{1-6}$ alkoxy, di($C_{1-6}$)alkylamino and $C_{2-6}$ alkoxycarbonyl. Further examples of typical substituents on $R^1$, $R^2$, $R^b$ or $R^c$, or on the cyclic moiety —$NR^aR^b$, include hydroxy($C_{1-6}$)alkyl, hydroxy($C_{1-6}$)alkylamino, hydroxy-[($C_{1-6}$)alkoxy]($C_{1-6}$) alkyl and $C_{1-6}$ alkoxy($C_{2-6}$)alkenyl.

Examples of specific substituents on $R^1$, $R^2$, $R^b$ or $R^c$, or on the cyclic moiety —$NR^aR^b$, include fluoro, chloro, methyl, methoxy, dimethylamino and tert-butoxycarbonyl. Further examples of specific substituents on $R^1$, $R^2$, $R^b$ or $R^c$, or on the cyclic moiety —$NR^aR^b$, include 2-hydroxy-2-methylpropyl, 2,3-dihydroxypropyl, 2-hydroxyethyl, 2-hydroxyethylamino, 2-hydroxy-3-methoxypropyl and 2-methoxyethenyl.

Particular values of $R^b$ include hydrogen, methyl, methoxyethyl, dimethylaminoethyl, phenyl, tetrahydrofuranylmethyl, tert-butoxycarbonyl-piperidinylmethyl, morpholinylethyl, pyridinyl, fluoropyridinyl, chloropyridinyl, dimethylaminopyridinyl, pyrazinyl, methylpyrazolylmethyl, methylimidazolylmethyl, pyridinylmethyl and methoxypyridinylmethyl. Further particular values of $R^b$ include methylpyridazinyl and methoxyethenylpyridinyl.

Alternatively, the moiety —$NR^aR^b$ may suitably represent azetidin-1-yl, pyrrolidin-1-yl, piperidin-1-yl, morpholin-4-yl, thiomorpholin-4-yl, piperazin-1-yl, homopiperidin-1-yl or homomorpholin-4-yl, any of which groups may be optionally substituted by one or more substituents. Typically, the moiety —$NR^aR^b$ may suitably represent pyrrolidin-1-yl, morpholin-4-yl or piperazin-1-yl, any of which groups may be optionally substituted by one or more substituents. Suitably, the cyclic moiety —$NR^aR^b$ may be substituted by $C_{1-6}$ alkyl, especially methyl.

Particular values of —$NR^aR^b$ include pyrrolidin-1-yl, morpholin-4-yl and 4-methylpiperazin-1-yl.

In one embodiment, $R^c$ represents optionally substituted $C_{1-6}$ alkyl, e.g. methyl. In another embodiment, $R^c$ represents optionally substituted aryl, e.g. phenyl. In a further embodiment, $R^d$ represents optionally substituted heteroaryl, e.g. pyridinyl.

Typical values of $R^c$ include methyl, phenyl and pyridinyl.

Suitable values of $R^d$ include methyl and ethyl, especially methyl.

Examples of typical substituents on $R^e$ include $C_{1-6}$ alkyl and heterocycloalkyl.

Examples of specific substituents on $R^e$ include methyl and piperazinyl.

Suitable values of $R^e$ include methylpyridazinyl, methylthiadiazolyl and piperazinylpyridazinyl.

Typically $R^1$ and $R^2$ independently represent hydrogen, halogen, nitro, hydroxy, $C_{1-6}$ alkyl, optionally substituted phenyl, optionally substituted pyrazolyl, optionally substituted isoxazolyl, optionally substituted thiazolyl, optionally substituted imidazolyl, optionally substituted pyridinyl, optionally substituted pyridazinyl, optionally substituted pyrimidinyl, optionally substituted imidazo[1,2-a]pyrazinyl, optionally substituted imidazo[1,2-a]pyrimidinyl, —$NR^aR^b$, —$CONR^aR^b$, —$NR^aCOR^c$, —$N(COR^c)_2$, —$NR^aSO_2R^c$, —$CO_2R^d$ or —$OR^e$, in which $R^a$, $R^b$, $R^c$ and $R^d$ and $R^e$ are as defined above.

In one embodiment, $R^1$ and $R^2$ independently represent hydrogen, halogen, nitro, hydroxy, optionally substituted phenyl, optionally substituted pyrazolyl, optionally substituted isoxazolyl, optionally substituted thiazolyl, optionally substituted imidazolyl, optionally substituted pyridinyl, —$NR^aR^b$, —$CONR^aR^b$, —$NR^aCOR^c$, —$N(COR^c)_2$, —$NR^aSO_2R^c$ or —$CO_2R^d$, in which $R^a$, $R^b$, $R^c$ and $R^d$ are as defined above.

Suitably, $R^1$ and $R^2$ independently represent hydrogen, chloro, bromo, nitro, hydroxy, methyl, phenyl, dimethylaminophenyl, pyrazolyl, methylpyrazolyl, 2-hydroxy-2-methylpropylpyrazolyl, 2-hydroxy-3-methoxypropylpyrazolyl, 2,3-dihydroxypropyl-pyrazolyl, hydroxyethylpyrazolyl, dimethylisoxazolyl, thiazolyl, methoxythiazolyl, imidazolyl, dimethylimidazolyl, pyridinyl, methylpyridinyl, methylpyridinyl-N-oxide, dimethylamino-pyridinyl, methoxypyridinyl, hydroxyethylpyridinyl, pyridazinyl, hydroxyethylamino(methyl)pyrimidinyl, —$NR^aR^b$, —$CONR^aR^b$, —$NR^aCOR^c$, —$N(COR^c)_2$, —$NR^aSO_2R^c$, —$CO_2R^d$ or —$OR^e$, in which $R^a$, $R^b$, $R^c$ and $R^d$ and $R^e$ are as defined above.

In one embodiment, $R^1$ and $R^2$ independently represent hydrogen, chloro, bromo, nitro, hydroxy, phenyl, dimethylaminophenyl, pyrazolyl, methylpyrazolyl, dimethylisoxazolyl, thiazolyl, methoxythiazolyl, imidazolyl, pyridinyl, methylpyridinyl, dimethylamino-pyridinyl, —$CONR^aR^b$, —$NR^aCOR^c$, —$N(COR^c)_2$, —$NR^aSO_2R^c$ or —$CO_2R^d$, in which $R^a$, $R^b$, $R^c$ and $R^d$ are as defined above.

In one particular group of compounds according to formula (I), $R^1$ represents optionally substituted heteroaryl. Typical examples include optionally substituted pyrazolyl, optionally substituted isoxazolyl, optionally substituted thiazolyl, optionally substituted imidazolyl, and optionally substituted pyridinyl. Further typical examples include optionally substituted pyridazinyl, optionally substituted pyrimidinyl, optionally substituted imidazo[1,2-a]pyrazinyl and optionally substituted imidazo[1,2-a]pyrimidinyl. Preferred examples include optionally substituted pyrazolyl and optionally substituted pyridinyl. Typical substituents include those as described herein. Examples of suitable substituents include $C_{1-6}$alkyl, $C_{1-6}$alkoxy and di($C_{1-6}$)alkylamino. Further examples of suitable substituents include hydroxy($C_{1-6}$) alkyl, hydroxy($C_{1-6}$)alkylamino, hydroxy[($C_{1-6}$)-alkoxy]($C_{1-6}$)alkyl and $C_{1-6}$ alkoxy($C_{2-6}$)alkenyl. Specific examples include methyl, methoxy and dimethylamino. Further specific examples include 2-hydroxy-2-methyl-propyl, 2,3-dihydroxypropyl, 2-hydroxyethyl, 2-hydroxyethylamino, 2-hydroxy-3-methoxypropyl and 2-methoxyethenyl.

In one preferred group of compounds $R^1$ represents substituted pyrazolyl, typically pyrazol-4-yl, or substituted pyridinyl, typically pyridin-3-yl, in which the substituents are selected from $C_{1-6}$ alkyl, hydroxy($C_{1-6}$)alkyl and hydroxy[($C_{1-6}$)alkoxy]($C_{1-6}$)alkyl. Preferred substituents include methyl, 2-hydroxy-2-methylpropyl, 2-hydroxyethyl and 2-hydroxy-3-methoxypropyl. Specific examples include 6-methylpyridin-3-yl, 1-methylpyrazol-4-yl, 1-(2-hydroxy-2-methylpropyl)pyrazol-4-yl, 1-(2-hydroxy-3-methoxypropyl)pyrazol-4-yl and 1-(2-hydroxyethyl)pyrazol-4-yl.

In one particular embodiment when $R^1$ represents optionally substituted heteroaryl, $R^2$ represents hydrogen or $C_{1-6}$ alkyl, suitably methyl. In another embodiment when $R^1$ represents optionally substituted heteroaryl, $R^2$ represents hydrogen. In a further embodiment when $R^1$ represents optionally substituted heteroaryl, $R^2$ represents $C_{1-6}$ alkyl, suitably methyl.

One sub-class of compounds according to the present invention is represented by the compounds of formula (IIA), and pharmaceutically acceptable salts and solvates thereof:

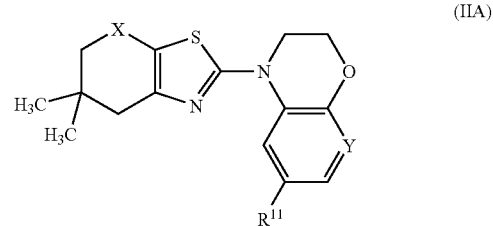

(IIA)

wherein $R^{11}$ represents halogen, nitro, hydroxy, optionally substituted aryl, optionally substituted heteroaryl, —$NR^aR^b$ or —$OR^e$; and —X—, Y, $R^a$ and $R^b$ are as defined above.

In one embodiment $R^{11}$ represents halogen, nitro, hydroxy, optionally substituted aryl, optionally substituted heteroaryl or —$NR^aR^b$.

Typically, $R^{11}$ represents halogen, nitro, hydroxy, optionally substituted phenyl, optionally substituted pyrazolyl, optionally substituted isoxazolyl, optionally substituted thiazolyl, optionally substituted imidazolyl, optionally substituted pyridinyl, optionally substituted pyridazinyl, optionally substituted pyrimidinyl, optionally substituted imidazo[1,2- a]pyrazinyl, optionally substituted imidazo[1,2-a]pyrimidinyl, —NR$^a$R$^b$ or —OR$^e$, in which R$^a$, R$^b$ and R$^e$ are as defined above.

In one embodiment, R$^{11}$ typically represents halogen, nitro, hydroxy, optionally substituted phenyl, optionally substituted pyrazolyl, optionally substituted isoxazolyl, optionally substituted thiazolyl, optionally substituted imidazolyl, optionally substituted pyridinyl or —NR$^a$R$^b$, in which R$^a$ and R$^b$ are as defined above.

Suitably, R$^{11}$ represents halogen, nitro, hydroxy, phenyl, dimethylaminophenyl, pyrazolyl, methylpyrazolyl, 2-hydroxy-2-methylpropylpyrazolyl, 2-hydroxy-3-methoxypropylpyrazolyl, 2,3-dihydroxypropylpyrazolyl, hydroxyethylpyrazolyl, dimethylisoxazolyl, thiazolyl, methoxythiazolyl, imidazolyl, dimethylimidazolyl, pyridinyl, methylpyridinyl, methylpyridinyl-N-oxide, dimethylaminopyridinyl, methoxypyridinyl, hydroxyethylpyridinyl, pyridazinyl, hydroxyethylamino(methyl)-pyrimidinyl, —NR$^a$R$^b$ or —OR$^e$, in which R$^a$, R$^b$ and R$^e$ are as defined above.

In one embodiment, R$^{11}$ suitably represents halogen, nitro, hydroxy, phenyl, dimethylaminophenyl, pyrazolyl, methylpyrazolyl, dimethylisoxazolyl, thiazolyl, methoxythiazolyl, imidazolyl, pyridinyl, methylpyridinyl, dimethylaminopyridinyl or —NR$^a$R$^b$, in which R$^a$ and R$^b$ are as defined above.

Another sub-class of compounds according to the present invention is represented by the compounds of formula (IIB), and pharmaceutically acceptable salts and solvates thereof:

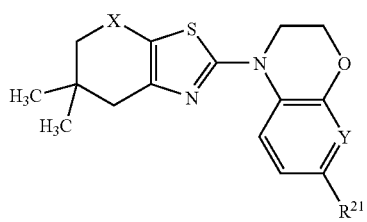

(IIB)

wherein

R$^{21}$ represents halogen, nitro, optionally substituted aryl, optionally substituted heteroaryl, —NR$^a$R$^b$, —CONR$^a$R$^b$, —NR$^a$COR$^c$, —N(COR$^c$)$_2$, —NR$^a$SO$_2$R$^c$ or —CO$_2$R$^d$; and —X—, Y, R$^a$, R$^b$, R$^c$ and R$^d$ are as defined above.

Typically, R$^{21}$ represents halogen, nitro, optionally substituted phenyl, optionally substituted pyrazolyl, optionally substituted isoxazolyl, optionally substituted thiazolyl, optionally substituted imidazolyl, optionally substituted pyridinyl, —NR$^a$R$^b$, —CONR$^a$R$^b$, —NR$^a$COR$^c$, —N(COR$^c$)$_2$, —NR$^a$SO$_2$R$^c$ or —CO$_2$R$^d$, in which R$^a$, R$^b$, R$^c$ and R$^d$ are as defined above.

Suitably, R$^{21}$ represents chloro, bromo, nitro, phenyl, dimethylaminophenyl, pyrazolyl, methylpyrazolyl, dimethylisoxazolyl, thiazolyl, methoxythiazolyl, imidazolyl, pyridinyl, methylpyridinyl, dimethylaminopyridinyl, —NR$^a$R$^b$, —CONR$^a$R$^b$, —NR$^a$COR$^c$, —N(COR$^c$)$_2$, —NR$^a$SO$_2$R$^c$ or —CO$_2$R$^d$, in which R$^a$, R$^b$, R$^c$ and R$^d$ are as defined above.

A further sub-class of compounds according to the present invention is represented by the compounds of formula (IIC), and pharmaceutically acceptable salts and solvates thereof:

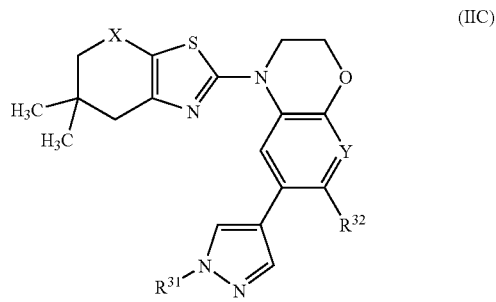

(IIC)

wherein

R$^{31}$ represents hydrogen, C$_{1-6}$ alkyl, hydroxy(C$_{1-6}$)alkyl or hydroxy[(C$_{1-6}$)alkoxy]-(C$_{1-6}$)alkyl;

R$^{32}$ represents hydrogen or C$_{1-6}$ alkyl; and

—X— and Y are as defined above.

Preferably R$^{31}$ represents C$_{1-6}$ alkyl, hydroxy(C$_{1-6}$)alkyl or hydroxy[(C$_{1-6}$)alkoxy]-(C$_{1-6}$)alkyl. Suitable examples include methyl, 2-hydroxy-2-methylpropyl, 2-hydroxyethyl and 2-hydroxy-3-methoxypropyl.

R$^{32}$ typically represents hydrogen or methyl. In one embodiment, R$^{32}$ represents hydrogen. In another embodiment, R$^{32}$ represents methyl.

Specific compounds in accordance with the present invention include each of the compounds whose preparation is described in the accompanying Examples 1-66, and pharmaceutically acceptable salts and solvates thereof. Further specific compounds in accordance with the present invention include each of the compounds whose preparation is described in the accompanying Examples 67-96, and pharmaceutically acceptable salts and solvates thereof.

The present invention also provides a pharmaceutical composition which comprises a compound of formula (I) as defined above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

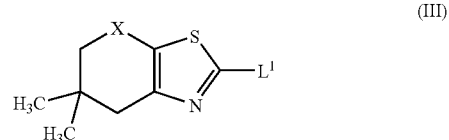

(III)

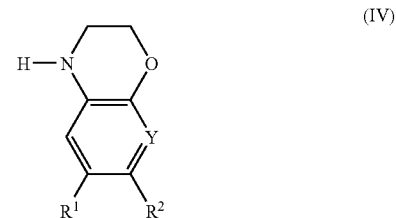

(IV)

wherein $R^1$, $R^2$ and X are as defined above, and $L^1$ represents a suitable leaving group.

The leaving group $L^1$ is typically a halogen atom, e.g. bromo.

The reaction is conveniently effected at an elevated temperature in a suitable solvent, e.g. a cyclic ether such as tetrahydrofuran or a hydrocarbon solvent such as toluene, typically in a base such as sodium tert-butoxide, ideally in the presence of a catalyst. The catalyst is typically a transition metal catalyst. A suitable transition metal catalyst is palladium(II) acetate, in which case the reaction is conveniently effected in the presence of tri-tert-butylphosphine tetrafluoroborate or dicyclohexylphosphino-naphthalene. Alternatively, the catalyst may suitably be dichloro[1,1'-bis(di-tert-butylphosphino)ferrocene]palladium.

Alternatively, the compounds of formula (I) above may be prepared by a process which comprises reacting a compound of formula (V) with a compound of formula (VI):

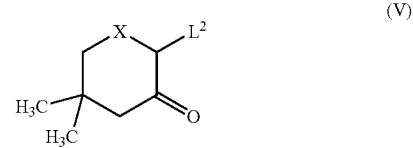

(V)

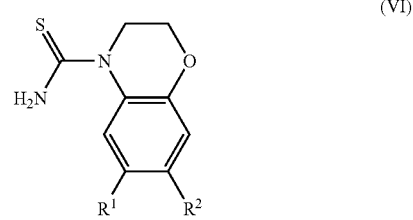

(VI)

wherein $R^1$, $R^2$ and X are as defined above, and $L^2$ represents a suitable leaving group.

The leaving group $L^2$ is typically a halogen atom, e.g. bromo.

The reaction is conveniently effected at an elevated temperature in a suitable solvent, e.g. a cyclic ether such as tetrahydrofuran, typically under basic conditions, e.g. in the presence of an organic base such as N,N-diisopropylethylamine.

The intermediates of formula (III) above wherein $L^1$ is bromo may be prepared from a compound of formula (VII):

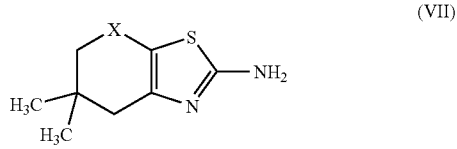
(VII)

wherein X is as defined above; by diazotization/bromination.

The reaction is conveniently effected by stirring compound (VII) with tert-butyl nitrite and copper(II) bromide in a suitable solvent, e.g. acetonitrile.

The intermediates of formula (VII) above may be prepared by reacting thiourea with a compound of formula (V) as defined above; under conditions analogous to those employed for the reaction between compounds (V) and (VI).

The intermediates of formula (IV) above may be prepared by reacting chloroacetyl chloride with a compound of formula (VIII):

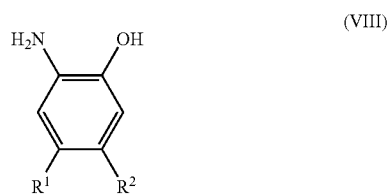
(VIII)

wherein $R^1$ and $R^2$ are as defined above; followed by reduction.

The reaction between chloroacetyl chloride and compound (VIII) is conveniently effected in a suitable solvent, e.g. a cyclic ether such as tetrahydrofuran, typically under basic conditions, e.g. in the presence of an organic base such as triethylamine.

Reduction of the resulting lactam intermediate is conveniently effected by treatment with a suitable reducing agent, e.g. borane-tetrahydrofuran complex, typically at an elevated temperature in a suitable solvent, e.g. a cyclic ether such as tetrahydrofuran.

The intermediates of formula (VI) above may be prepared by reacting the appropriate compound of formula (IV) with 1,1'-thiocarbonyldiimidazole; followed by reaction of the compound thereby obtained with ammonia.

Where they are not commercially available, the starting materials of formula (V) and (VIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^1$ or $R^2$ represents a halogen atom such as bromo may be converted into the corresponding compound wherein $R^1$ or $R^2$ represents optionally substituted aryl or heteroaryl by treatment with an optionally substituted aryl or heteroaryl boronic acid or an ester thereof, e.g. a pinacol ester, in the presence of a catalyst. The catalyst may typically be a transition metal catalyst. Suitable catalysts include tetrakis(triphenylphosphine)palladium(0) and bis(tri-tert-butylphosphino)palladium(0), in which case the transformation may conveniently be effected at an elevated temperature in the presence of a base such as sodium carbonate, potassium phosphate or potassium acetate, suitably in an inert solvent such as tetrahydrofuran, 1,2-dimethoxyethane or N,N-dimethylformamide, optionally in the presence of tetrabutylammonium bromide.

Alternatively, a compound of formula (I) wherein $R^1$ or $R^2$ represents a halogen atom such as bromo may be converted into the corresponding compound wherein $R^1$ or $R^2$ represents optionally substituted aryl or heteroaryl by a two-step procedure which comprises (i) initial conversion of the halogen to a boronic acid or an ester thereof, e.g. a pinacol ester, using methods known to those skilled in the art; and (ii) reaction of the derivative thereby obtained with an optionally substituted aryl or heteroaryl derivative possessing a suitable leaving group, for example a halogen such as chloro or bromo, using methods as described herein.

A compound of formula (I) wherein $R^1$ or $R^2$ represents a halogen atom such as bromo may be converted into the corresponding compound wherein $R^1$ or $R^2$ represents optionally substituted aryl or heteroaryl by treatment with the appropriate aryl- or heteroaryl-substituted tributylstannane reagent. The reaction may conveniently be effected at an elevated temperature in an inert solvent, e.g. an ethereal solvent such as tetrahydrofuran or 1,2-dimethoxyethane.

A compound of formula (I) wherein $R^1$ or $R^2$ represents a halogen atom such as bromo may be converted into the corresponding compound wherein $R^1$ or $R^2$ represents imidazol-1-yl, or an optionally substituted derivative thereof, by treatment with imidazole, or an optionally substituted derivative thereof, in the presence of a catalytic amount of copper(I) oxide. The reaction may conveniently be effected at an elevated temperature in a suitable solvent, e.g. acetonitrile, typically in the presence of salicylaldehyde hydrazine and a base, e.g. caesium carbonate.

A compound of formula (I) wherein $R^1$ or $R^2$ represents aryl or heteroaryl substituted by a halogen atom such as chloro may be converted into the corresponding compound wherein $R^1$ or $R^2$ represents unsubstituted aryl or heteroaryl by catalytic hydrogenation. The transformation is conveniently effected by a transfer hydrogenation procedure using a hydrogenation catalyst, e.g. palladium on charcoal, in the presence of a hydrogen donor such as cyclohexene, typically at an elevated temperature in a solvent such as ethanol.

A compound of formula (I) wherein $R^1$ or $R^2$ is nitro may be converted into the corresponding compound wherein $R^1$ or $R^2$ is $-NH_2$ by conventional catalytic hydrogenation.

A compound of formula (I) wherein $R^1$ or $R^2$ represents a halogen atom, e.g. bromo, may be converted into the corresponding compounds wherein $R^1$ or $R^2$ is $-NH_2$ by reaction with an imine, such as benzophenone imine, in the presence of a suitable base, e.g. sodium tert-butoxide, a catalyst such as tris(dibenzylidineacetone)dipalladium(0) and a chelating ligand such as rac-2,2'-bis(diphenylphosphino)-1,1'-binaphthyl, suitably in an inert solvent such as tetrahydrofuran.

A compound of formula (I) wherein $R^1$ or $R^2$ represents a halogen atom, e.g. chloro or bromo, may be converted into the corresponding compound wherein $R^1$ or $R^2$ represents $-NR^aR^b$ by treatment with the appropriate compound of formula $H-NR^aR^b$ in the presence of a catalyst. Similarly, a compound of formula (I) wherein $R^1$ or $R^2$ represents $-NH_2$ may be converted into the corresponding compound wherein $R^1$ or $R^2$ represents $-NHR^b$ by treatment with the appropriate compound of formula $R^b-Br$ or $R^b-Cl$ in the presence of a catalyst. The catalyst may typically be a transition metal catalyst. Suitable catalysts include palladium(II) acetate and dichloro[1,1'-bis(di-tert-butylphosphino)ferrocene]-palladium, in which case the transformation may conveniently be effected at an elevated temperature in a suitable solvent, e.g. a cyclic ether such as tetrahydrofuran, or a hydrocarbon such as toluene, typically in a base such as sodium tert-butoxide, ideally in the presence of palladium(II) acetate and tri-tert-butylphosphine tetrafluoroborate.

Alternatively, a compound of formula (I) wherein $R^1$ or $R^2$ represents —$NH_2$ may be converted into the corresponding compound wherein $R^1$ or $R^2$ represents —$NHR^b$ by treatment with the appropriate compound of formula $R^b$—Br or $R^b$—Cl in the presence of a base, such as diisopropylethylamine, suitably at elevated temperature.

A compound of formula (I) wherein $R^1$ or $R^2$ represents —$NH_2$ may be converted into the corresponding compound wherein $R^1$ or $R^2$ represents —$NHCH_2R^{bb}$, in which $CH_2R^{bb}$ corresponds to the group $R^b$ as defined above, by a reductive amination procedure which comprises reaction with an aldehyde derivative of formula OHC—$R^{bb}$ under reducing conditions. The reducing conditions may typically be generated by a mixture of phenylsilane and dibutyltin dichloride, in which case the reaction will suitably be effected at an elevated temperature in an inert solvent, e.g. a cyclic ether such as tetrahydrofuran.

A compound of formula (I) wherein $R^1$ or $R^2$ represents —$NHR^b$ may be converted into the corresponding compound wherein $R^1$ or $R^2$ represents —$N(CH_2R^{aa})R^b$, in which $R^{aa}$ represents hydrogen or $C_{1-5}$ alkyl, by a reductive amination procedure which comprises reaction with an aldehyde derivative of formula OHC—$R^{aa}$ in the presence of a reducing agent such as sodium triacetoxyborohydride.

A compound of formula (I) wherein $R^1$ or $R^2$ represents —$NH_2$ may be converted into the corresponding compound wherein $R^1$ or $R^2$ represents —$NHCOR^c$ or —$N(COR^c)_2$ by treatment with a compound of formula $R^c$—COCl. Similarly, a compound of formula (I) wherein $R^1$ or $R^2$ represents —$NH_2$ may be converted into the corresponding compound wherein $R^1$ or $R^2$ represents —$NHSO_2R^c$ by treatment with a compound of formula $R^c$—$SO_2Cl$. The reaction is conveniently accomplished in an inert solvent, e.g. dichloromethane, in the presence of an organic base such as pyridine.

A compound of formula (I) wherein $R^1$ or $R^2$ represents —$CO_2R^d$ may be converted into the corresponding compound wherein $R^1$ or $R^2$ represents —$CONR^aR^b$ by a two-step procedure which comprises: (i) saponification of the ester moiety with a base such as sodium hydroxide; and (ii) reaction of the carboxy derivative thereby obtained with the appropriate amine of formula H—$NR^aR^b$, ideally in the presence of a condensing agent such as 1-[3-(dimethylamino)propyl]-3-ethylcarbodiimide (EDC) and 1-hydroxybenzotriazole (HOBT).

A compound of formula (I) wherein $R^1$ or $R^2$ represents —OH may be converted into the corresponding compound wherein $R^1$ or $R^2$ represents —$OR^e$ by treatment with the appropriate compound of formula $R^e$—Br or $R^e$—Cl in the presence of a base, such as potassium carbonate or cesium carbonate. The reaction may suitably be performed in an appropriate solvent, such as N,N-dimethylformamide, typically at elevated temperature.

A compound of formula (I) that contains a dihydroxyalkyl substitutent, in which the hydroxy groups are adjacent, may be prepared by oxidation of the corresponding alkylene derivative using reagents known to those skilled in the art, for example osmium tetroxide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (β, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 µM or better.

EXAMPLES

Compounds were named with the aid of Beilstein Autonom. All reactions involving air- or moisture-sensitive reagents were performed under a nitrogen atmosphere using dried solvents and glassware. All NMRs were obtained either at 300 MHz or 400 MHz.

ABBREVIATIONS

EtOAc—ethyl acetate DCM—dichloromethane
DMF—N,N-dimethylformamide DME—ethylene glycol dimethyl ether
DMSO—dimethylsulphoxide $^i$Pr—isopropyl
Et$_2$O—diethyl ether THF—tetrahydrofuran
r.t.—room temperature sat.—saturated
MeOH—methanol AcOH—acetic acid
EtOH—ethanol IPA—isopropyl alcohol
RT—retention time Me—methyl
h—hour conc.—concentrated
obsc.—obscured MeCN—acetonitrile
SiO$_2$—silica br.—broad
prep—preparative M—mass
brine—saturated aqueous sodium chloride solution
HPLC—High Performance Liquid Chromatography
LCMS—Liquid Chromatography Mass Spectrometry
DIPEA—N,N-diisopropylethylamine
EDC—1-[3-(dimethylamino)propyl]-3-ethylcarbodiimide hydrochloride
(Bu$^t$)$_3$PBF$_4$—tri-tert-butylphosphine tetrafluoroborate
HOBT—1-hydroxybenzotriazole hydrate
LDA—lithium diisopropylamide Compound purities and retention times were determined by LCMS using the following
HPLC methods:
Luna C18(2) 100×4.6 mm, 5 μm column.
  Eluted with
Mobile Phase A: 99.92% water, 0.08% formic acid
Mobile Phase B: 99.92% MeCN, 0.08% formic acid.
  Or
Mobile Phase A: 5 mM NH$_4$OAc, pH 5.8
Mobile Phase B: 95:5 MeCN:100 mM NH$_4$OAc, pH 5.8.
Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Preparative HPLC was performed using the following HPLC methods:
Gemini C18 30×3.0 mm, 3 μm column.
  Eluted with
Mobile Phase A: 99.9% 10 mM ammonium formate, 0.1% formic acid
Mobile Phase B: 94.9% MeCN, 0.1% formic acid, 5% Mobile Phase A.
  Or
Mobile Phase A: 99.9% 10 mM ammonium formate, 0.1% ammonia solution
Mobile Phase B: 94.9% MeCN, 0.1% ammonia solution, 5% mobile phase A.

Gradient program (flow rate 1.2 mL/min, column temperature 40° C.):

| Time | A % | B % |
|---|---|---|
| 0.00 | 95.0 | 5.0 |
| 4.00 | 5.0 | 95.0 |
| 5.50 | 5.0 | 95.0 |

Intermediate 1

2-Bromo-5,5-dimethylcyclohexane-1,3-dione

Bromine (0.51 mL, 10 mmol) was added dropwise to a solution of 5,5-dimethylcyclohexane-1,3-dione (1.4 g, 10 mmol) in AcOH (20 mL) at r.t. The reaction mixture was stirred for 2 h and then the product was isolated by filtration. The precipitate was washed with Et$_2$O (2×100 mL) and then dried in vacuo give the title compound in quantitative yield as a light brown solid, which was used without further purification. LCMS (ES+) 218.9 (M+H)$^+$.

Intermediate 2

2-Amino-5,5-dimethyl-5,6-dihydro-1,3-benzothiazol-7(4H)-one

Thiourea (6.9 g, 91 mmol) and DIPEA (18 mL, 91 mmol) were added to a solution of Intermediate 1 (20 g, 91 mmol) in THF (300 mL), The mixture was heated to reflux for 2 h, then cooled to r.t., concentrated in vacuo and the crude product poured into saturated aqueous sodium bicarbonate solution (300 mL). The precipitate produced was filtered off under reduced pressure to give the title compound as a white solid (10.3 g, 58%). $\delta_H$ (DMSO-d$_6$) 1.03 (6H, s), 2.27 (2H, s), 2.58 (2H, s), 8.11 (2H, s). LCMS (ES+) 197 (M+H)$^+$.

Intermediate 3

2-Bromo-5,5-dimethyl-5,6-dihydro-1,3-benzothiazol-7(4H)-one

Copper(II) bromide (8.7 g, 39 mmol) and tert-butyl nitrite (5.1 g, 49 mmol) were added to a stirred solution of Intermediate 2 (7 g, 36 mmol) in MeCN (150 mL). After stirring at r.t. for 2 h, the reaction mixture was poured into 10% HCl (100 mL) and extracted with DCM (2×150 mL). The organics were dried (MgSO$_4$) and concentrated in vacuo to give the title compound as an orange solid (7.0 g, 74%). $\delta_H$ (CDCl$_3$) 1.07 (6H, s), 2.41 (2H, s), 2.84 (2H, s). LCMS (ES+) 260.0 (M+H)$^+$.

Intermediate 4

2-Amino-7,7-dimethyl-5,6,7,8-tetrahydro-4H-[1,3]thiazolo[5,4-c]azepin-4-one

Concentrated sulfuric acid (86 mL) was added to a stirred solution of Intermediate 2 (26.7 g, 100 mmol) in chloroform (900 mL). Sodium azide (9.8 g, 200 mmol) was added portionwise over 2 h and the apparatus fitted with a bubbler to monitor the evolution of gas. The reaction mixture was then stirred for 48 h at r.t., after which the solvent was decanted off. Ice was added to the resulting oil. A solution of saturated aqueous sodium carbonate solution was added slowly until a pH of 9 was reached. The resulting brown solid was filtered and washed several times with water and $Et_2O$ to give the title compound as a light brown solid (18.5 g, 63%). $\delta_H$ (DMSO-$d_6$) 0.96 (6H, s), 2.91 (2H, d, J 5.1 Hz), 7.34 (2H, s), 7.55 (1H, t, J 4.9 Hz). LCMS (ES+) 211.0 (M+H)$^+$.

Intermediate 5

2-Bromo-7,7-dimethyl-5,6,7,8-tetrahydro-4H-[1,3]thiazolo[5,4-c]azepin-4-one

Prepared following the procedure for Intermediate 3 using Intermediate 4 (4.54 g, 21.5 mmol), copper(II) bromide (5.18 g, 23.2 mmol) and tert-butyl nitrite (3.6 mL, 30 mmol) in MeCN (80 mL) The crude material was purified by flash chromatography ($SiO_2$, 1:1 heptane-EtOAc) to give the title compound as a yellow solid (4.01 g, 68%). $\delta_H$ (DMSO-$d_6$) 0.99 (6H, s), 2.89 (2H, s), 2.98 (2H, d, J 5.2 Hz), 8.29 (1H, br s). LCMS (ES+) 277.0 and 275.0 (M+H)$^+$.

Intermediate 6

6-Bromo-4H-benzo[1,4]oxazin-3-one

Triethylamine (2.4 mL, 17 mmol) was added to 2-amino-4-bromophenol (2.5 g, 13 mmol) in THF (80 mL). The reaction was cooled in ice and chloroacetyl chloride (1.12 mL, 14 mmol) added portionwise. It was stirred with cooling for 10 min then allowed to warm to r.t. and stirred for a further 2 h. The reaction mixture was cooled in ice and sodium hydride (1.05 g of a 60% suspension in oil, 26 mmol) was added portionwise. The mixture was stirred with ice-bath cooling for 20 min then at r.t. for 2 h before being quenched with water (20 mL). The THF was removed in vacuo and the resulting mixture diluted with water (100 mL). The precipitate was filtered off, washed with water (3×50 mL) and dried in vacuo to yield the title compound as a beige solid (2.14 g, 70%). $\delta_H$ (DMSO-$d_6$) 4.60 (2H, s), 6.92 (1H, d, J 8.5 Hz), 7.02 (1H, d, J 2.3 Hz), 7.08 (1H, dd, J 8.5, 2.3 Hz), 10.81 (1H, br s).

Intermediates 7 to 10

Prepared in the same manner as Intermediate 6.

Intermediate 7

6-Nitro-4H-benzo[1,4]oxazin-3-one

Using 2-amino-4-nitrophenol (10 g, 65 mmol), triethylamine (11.7 mL, 84 mmol) and chloroacetyl chloride (5.4 mL, 68 mmol) in THF (150 mL) followed by sodium hydride (5.2 g of a 60% suspension in oil, 130 mmol) to yield the title compound as a grey solid (5 g, 33%). $\delta_H$ (DMSO-$d_6$) 4.78 (2H, s), 7.15 (1H, d, J 8.9 Hz), 7.74 (1H, d, J 2.4 Hz), 7.84 (1H, dd, J 8.9, 2.6 Hz), 11.09 (1H, s).

Intermediate 8

6-Phenyl-4H-benzo[1,4]oxazin-3-one

Using 2-amino-4-phenylphenol (1 g, 5.4 mmol), triethylamine (0.97 mL, 7.0 mmol) and chloroacetyl chloride (0.72 g, 5.9 mmol) in THF (35 mL) followed by sodium hydride (0.27 g of a 60% suspension in oil, 6 mmol) to yield the title compound as a pale yellow solid (1.2 g, 91%). $\delta_H$ (DMSO-$d_6$) 4.62 (2H, s), 7.29-7.56 (8H, m), 10.81 (1H, s).

Intermediate 9

3-Oxo-3,4-dihydro-2H-benzo[1,4]oxazine-7-carboxylic acid methyl ester

Using methyl 4-amino-3-hydroxybenzoate (2 g, 12 mmol), triethylamine (2.17 mL, 16 mmol) and chloroacetyl chloride (1.13 mL, 13 mmol) in THF (70 mL) followed by sodium hydride (1.0 g of a 60% suspension in oil, 24 mmol) to yield the title compound as a brown solid (2.33 g, 94%). $\delta_H$ (DMSO-$d_6$) 3.81 (3H, s), 4.65 (2H, s), 6.99 (1H, d, J 8.3 Hz), 7.43 (1H, d, J 1.5 Hz), 7.59 (1H, dd, J 8.5, 1.9 Hz), 11.10 (1H, br s). LCMS (ES+) 208 (M+H)$^+$.

Intermediate 10

6-Chloro-7-nitro-4H-benzo[1,4]oxazin-3-one

Using 2-amino-4-chloro-5-nitrophenol (3.0 g, 15 mmol), triethylamine (2.7 mL, mmol) and chloroacetyl chloride (2.0 g, 17 mmol) in THF (100 mL) followed by sodium hydride (1.3 g of a 60% suspension in oil, 30 mmol) to yield the title compound as an orange solid (1.8 g, 54%). $\delta_H$ (DMSO-$d_6$) 4.74 (2H, s), 7.07 (1H, s), 7.77 (1H, s), 11.29 (1H, br s).

Intermediate 11

7-Amino-4H-benzo[1,4]oxazin-3-one

7-Nitro-4H-benzo[1,4]oxazin-3-one (0.65 g, 3.3 mmol) and 10% palladium on carbon (0.13 g) were combined in EtOAc (15 mL) and MeOH (15 mL) and hydrogenated for 2 h at atmospheric pressure. The catalyst was removed by filtration through celite and the filtrate reduced in vacuo to yield the title compound as a colourless oil (0.50 g, 91%). $\delta_H$ (DMSO-$d_6$) 4.42 (2H, s), 4.89 (2H, br s), 6.13-6.20 (2H, m), 6.56 (1H, d, J 8.1 Hz), 10.27 (1H, br s).

Intermediate 12

7-Bromo-4H-benzo[1,4]oxazin-3-one

Intermediate 11 (0.5 g, 3.0 mmol), copper(II) bromide (0.67 g, 3.3 mmol) and tert-butyl nitrite (0.52 mL, 4.3 mmol) were combined in acetonitrile (30 mL) and stirred for 3 h. The mixture was partitioned between EtOAc (100 mL) and water (100 mL). The organics were dried ($MgSO_4$), filtered and concentrated in vacuo to give a crude product which was purified by prep HPLC to yield the title compound as a beige solid (65 mg, 9%). $\delta_H$ (DMSO-$d_6$) 4.60 (2H, br s), 6.83 (1H, d, J 8.3 Hz), 7.10-7.20 (2H, m), 10.83 (1H, br s).

Intermediate 13

6-Bromo-3,4-dihydro-2H-benzo[1,4]oxazine

Borane-THF (13.2 mL of a 1M solution in THF, 13.2 mmol) was added portionwise to Intermediate 6 (2.0 g, 8.0 mmol) in THF (50 mL) at r.t. The resulting solution was stirred at r.t. for 10 min, heated to reflux for 1 h and then allowed to cool to r.t. The reaction was cooled in an ice bath and quenched with water (20 mL) and 2N aqueous sodium hydroxide solution (20 mL). The solvent was removed in vacuo and the resulting mixture diluted with water (100 mL). It was extracted with EtOAc (100 mL), washed with brine (100 mL), dried ($MgSO_4$), filtered and concentrated in vacuo to yield the title compound as a brown oil (2 g, quant). $\delta_H$ (DMSO-d$_6$) 3.36-3.44 (2H, m), 3.81 (1H, br s), 4.18-4.25 (2H, m), 6.68 (3H, m).

Intermediates 14 to 22

Prepared in the same manner as Intermediate 13.

Intermediate 14

6-Nitro-3,4-dihydro-2H-benzo[1,4]oxazine

Using Intermediate 7 (4.33 g, 22.5 mmol) and borane-THF (40 mL of a 1M solution in THF, 40 mmol) in THF (60 mL) to yield the title compound as a red solid (2.0 g, 49%). $\delta_H$ (DMSO-d$_6$) 3.30-3.37 (3H, m), 4.21-4.28 (2H, m), 6.83 (1H, d, J 8.9 Hz), 7.36-7.49 (2H, m).

Intermediate 15

6-Chloro-3,4-dihydro-2H-benzo[1,4]oxazine

Using 6-chloro-4H-benzo[1,4]oxazin-3-one (0.6 g, 3.3 mmol) and borane-THF (16.4 mL of a 1M solution in THF, 16.4 mmol) in THF (15 mL) to yield the title compound as a clear oil (0.16 g, 55%). $\delta_H$ (CDCl$_3$) 3.35-3.47 (2H, m), 3.81 (1H, br s), 4.17-4.29 (2H, m), 6.54-6.62 (2H, m), 6.64-6.72 (1H, m).

Intermediate 16

6-Phenyl-3,4-dihydro-2H-benzo[1,4]oxazine

Using Intermediate 8 (1.6 g, 7.1 mmol) and borane-THF (17 mL of a 1M solution in THF, 17 mmol) in THF (25 mL) to yield the title compound as a light brown solid (340 mg, 23%). $\delta_H$ (MeOD-d$_4$) 3.28-3.40 (2H, m), 4.17-4.29 (2H, m), 7.29-7.56 (8H, m). LCMS (ES+) 213 (M+H)$^+$.

Intermediate 17

7-Nitro-3,4-dihydro-2H-benzo[1,4]oxazine

Using 7-nitro-4H-benzo[1,4]oxazin-3-one (2.9 g, 15 mmol) and borane-THF (45 ml of a 1M solution in THF, 45 mmol) in THF (40 mL) to yield the title compound as an orange solid (2.2 g, 83%). $\delta_H$ (CDCl$_3$) 3.48-3.60 (2H, m), 4.20-4.32 (2H, m), 6.52 (1H, d, J 8.9 Hz), 7.69 (1H, d, J 2.4 Hz), 7.74 (1H, dd, J 8.9, 2.4 Hz). LCMS (ES+) 181 (M+H)$^+$.

Intermediate 18

7-Chloro-3,4-dihydro-2H-benzo[1,4]oxazine

Using 7-chloro-4H-benzo[1,4]oxazin-3-one (2.3 g, 13.5 mmol) and borane-THF (40 mL of a 1M solution in THF, 40 mmol) in THF (40 mL) to yield the title compound as a cream solid (2.2 g, 96%). $\delta_H$ (CDCl$_3$) 3.34-3.40 (2H, m), 4.16-4.28 (2H, m), 6.51-6.55 (1H, m), 6.59 (1H, d, J 2.4 Hz), 6.68 (1H, dd, J 8.1, 0.4 Hz). LCMS (ES+) 170 (M+H)$^+$.

Intermediate 19

7-Bromo-3,4-dihydro-2H-benzo[1,4]oxazine

Using Intermediate 12 (0.9 g, 3.9 mmol) and borane-THF (8 mL of a 1M solution in THF, 8 mmol) in THF (20 mL) to yield the title compound as a brown oil (0.8 g, 95%). $\delta_H$ (CDCl$_3$) 3.30-3.47 (2H, m), 4.16-4.29 (2H, m), 6.45 (1H, d, J 8.3 Hz), 6.84 (1H, m), 6.91 (1H, d, J 2.1 Hz).

Intermediate 20

3,4-Dihydro-2H-benzo[1,4]oxazine-7-carboxylic acid methyl ester

Using Intermediate 9 (2.62 g, 16 mmol) and borane-THF (31 mL of a 1M solution in THF, 31 mmol) in THF (31 mL) to yield the title compound as a cream solid (0.76 g, 25%). $\delta_H$ (DMSO-d$_6$) 3.73 (3H, s), 3.28-3.40 (2H, m), 4.04-4.18 (2H, m), 6.57 (1H, d, J 8.3 Hz), 6.72 (1H, s), 7.18 (1H, d, J 1.7 Hz), 7.33 (1H, d, J 8.5, 1.9 Hz). LCMS (ES+) 194 (M+H)$^+$.

Intermediate 21

6-Chloro-7-nitro-3,4-dihydro-2H-benzo[1,4]oxazine

Using Intermediate 10 (1.9 g, 8.3 mmol) and borane-THF (21 mL of a 1M solution in THF, 21 mmol) in THF (30 mL) to yield the title compound as a green solid (0.66 g, 37%). $\delta_H$ (DMSO-d$_6$) 3.42-3.57 (2H, m), 4.15-4.30 (2H, m), 7.51 (1H, s), 7.58 (1H, s). LCMS (ES+) 215 (M+H)$^+$.

Intermediate 22

2,3-Dihydro-1H-pyrido[2,3-b][1,4]oxazine

Using 1H-pyrido[2,3-b][1,4]oxazin-2-one (0.3 g, 2 mmol) and borane-THF (8 mL of a 1M solution in THF, 8 mmol) in THF (20 mL) to yield the title compound as a yellow solid (180 mg, 66%). $\delta_H$ (CDCl$_3$) 3.38-3.46 (2H, m), 3.85 (1H, br s), 4.38-4.45 (2H, m), 6.74 (1H, dd, J 7.7, 4.9 Hz), 6.83-6.88 (1H, m), 7.61 (1H, dd, J 4.7, 1.5 Hz).

Intermediate 23

2-(6-Chloro-7-nitro-2,3-dihydrobenzo[1,4]oxazin-4-yl)-5,5-dimethyl-5,6-dihydro-4H-benzothiazol-7-one Following Method B, using Intermediate 3 (100 mg, 0.38 mmol), Intermediate 21 (81 mg, 0.38 mmol), sodium tert-butoxide (91 mg, 0.96 mmol), (Bu$^t$)$_3$PBF$_4$ (21 mg, 0.076 mmol) and palladium(II) acetate (9 mg, 0.038 mmol) in THF (3 mL) heated to 120° C. under microwave irradiation for 40 min. The crude material was purified by prep HPLC to give the title compound as a light green solid (11 mg, 7%). $\delta_H$ (CDCl$_3$) 1.19 (6H, s), 2.49 (2H, s), 2.90 (2H, s), 4.09-4.17 (2H, m), 4.42-4.49 (2H, m), 7.66 (1H, s), 8.81 (1H, s). LCMS (ES+) 394 (M+H)$^+$.

Intermediate 24

4-(5,5-Dimethyl-7-oxo-4,5,6,7-tetrahydrobenzothiazol-2-yl)-3,4-dihydro-2H-benzo[1,4]oxazine-7-carboxylic acid NaOH (0.5 mL of a 2N solution in water, 1.0 mmol) was added to Example 5 (50 mg, 0.13 mmol) in MeOH (4 mL) and the mixture heated to 60° C. for 90 min. The solid material was filtered under reduced pressure, washed with water (3×20 mL) and purified by prep HPLC to give the title compound as an off-white solid (7 mg, 14%). $\delta_H$ (MeOD-d$_4$) 1.17 (6H, s), 2.45 (2H, s), 2.83 (2H, s), 4.17-4.27 (2H, m), 4.35-4.44 (2H, m), 7.60-7.65 (1H, m), 8.13 (1H, d, J 8.48 Hz), 8.50 (1H, s). LCMS (ES+) 359 (M+H)+.

Intermediate 25

6-Bromo-2,3-dihydrobenzo[1,4]oxazine-4-carboxylic acid tert-butyl ester

A mixture of Intermediate 13 (4.0 g, 18.6 mmol), di-tert-butyl dicarbonate (4.9 g, 22.4 mmol), 4-(dimethylamino)pyridine (50 mg, catalytic) and triethylamine (2.6 mL, 18.6 mmol) in THF (50 mL) was heated to reflux overnight. After cooling to r.t. the reaction mixture was concentrated in vacuo. The crude material was purified by column chromatography (SiO$_2$, linear gradient elution: 0-100% EtOAc in heptane) to give the title compound as an off-white solid (3.5 g, 60%). $\delta_H$ (DMSO-d$_6$) 1.56 (9H, s), 3.80-3.89 (2H, m), 4.19-4.26 (2H, m), 6.77 (1H, d, J 8.9 Hz), 7.08 (1H, dd, J 8.7, 2.4 Hz), 8.02 (1H, s).

Intermediate 26

6-(6-Methylpyridin-3-yl)-2,3-dihydrobenzo[1,4] oxazine-4-carboxylic acid tert-butyl ester A mixture of Intermediate 25 (220 mg, 0.73 mmol), 2-methylpyridine-5-boronic acid hydrate (100 mg, 0.73 mmol), potassium phosphate (465 mg, 2.19 mmol), tetrakis(triphenylphosphine)palladium(0) (10 mg, catalytic) and water (1 mL) in DME (8 mL) was heated to 120° C. under microwave irradiation for 1 h. After cooling to r.t. the reaction mixture was concentrated in vacuo. The crude material was purified by column chromatography (SiO$_2$, linear gradient elution: 0-50% EtOAc in heptane) to give the title compound as an off-white solid (155 mg, 65%). $\delta_H$ (CDCl$_3$) 1.59 (9H, s), 2.60 (3H, s), 3.87-3.97 (2H, m), 4.25-4.35 (2H, m), 6.97 (1H, d, J 8.3 Hz), 7.16-7.24 (2H, m), 7.74 (1H, dd, J 8.1, 2.4 Hz), 8.04 (1H, br s), 8.70 (1H, d, J 2.6 Hz).

Intermediate 27

6-(1-Methyl-1H-pyrazol-4-yl)-2,3-dihydrobenzo[1, 4]oxazine-4-carboxylic acid tert-butyl ester A mixture of Intermediate 25 (0.9 g, 2.8 mmol), 1-methyl-4-(4,4,5,5-tetramethyl-[1,3,2]dioxaborolan-2-yl)-1H-pyrazole (1.19 g, 5.7 mmol), potassium phosphate (1.2 g, 5.7 mmol), tetrakis(triphenylphosphine)palladium(0) (10 mg, catalytic) and water (2 mL) in DME (15 mL) was heated to 120° C. under microwave irradiation for 1 h. After cooling to r.t. the reaction mixture was concentrated in vacuo. The crude material was purified by column chromatography (SiO$_2$, linear gradient elution: 0-50% EtOAc in heptane) to give the title compound as an off-white solid (240 mg, 27%). $\delta_H$ (MeOD-d$_4$) 1.45 (9H, s), 3.69-3.76 (2H, m), 3.77 (3H, s), 4.06-4.13 (2H, m), 6.71 (1H, d, J 8.5 Hz), 6.98 (1H, dd, J 8.5, 2.1 Hz), 7.55 (1H, s), 7.58 (1H, s), 7.83 (1H, br s).

Intermediate 28

6-(6-Methylpyridin-3-yl)-3,4-dihydro-2H-benzo[1,4] oxazine

Intermediate 26 (150 mg, 0.46 mmol) was dissolved in trifluoroacetic acid (10 mL) and the mixture stirred for 3 h at r.t. The reaction mixture was concentrated in vacuo and the residue partitioned between DCM (50 mL) and aqueous sodium bicarbonate (50 mL). The organics were dried (MgSO$_4$) and concentrated in vacuo to give the title compound as an off-white solid (110 mg, 97%). $\delta_H$ (CDCl$_3$) 2.59 (3H, s), 3.41-3.51 (2H, m), 4.25-4.33 (2H, m), 6.76-6.90 (3H, m), 7.17 (1H, d, J 8.1 Hz), 7.69 (1H, dd, J 8.1, 2.4 Hz), 8.67 (1H, d, J 2.1 Hz).

Intermediate 29

6-(1-Methyl-1H-pyrazol-4-yl)-3,4-dihydro-2H-benzo [1,4]oxazine

Intermediate 27 (240 mg, 0.76 mmol) was dissolved in trifluoroacetic acid (5 mL) and the mixture stirred for 1 h at r.t. The reaction mixture was concentrated in vacuo and the residue partitioned between DCM (50 mL) and aqueous sodium bicarbonate (50 mL). The organics were washed with brine (50 mL), dried (MgSO$_4$) and concentrated in vacuo to give the title compound as an off-white solid (160 mg, 97%). $\delta_H$ (MeOD-d$_4$) 3.36-3.42 (2H, m), 3.90 (3H, s), 4.19-4.26 (2H, m), 6.70-6.82 (3H, m), 7.64 (1H, s), 7.69 (1H, s).

Intermediate 30

6-Bromo-2,3-dihydro-benzo[1,4]oxazine-4-carbothioic acid amide

A solution of Intermediate 13 (11.68 g, 54.6 mmol) in THF (120 mL) was added to thiocarbonyldiimidazole (19.45 g, 109.12 mmol) and the mixture divided between 8 microwave vials. The reactions were each heated to 120° C. under microwave irradiation for 15 minutes, then cooled to r.t., combined and poured into methanolic ammonia (100 mL of a 7M solution, 0.7 mol) and stirred at r.t. overnight. The mixture was concentrated in vacuo, and the residue partitioned between water (200 mL), 2M HCl (50 mL) and then hexane and ether. The resulting solid was collected by filtration and washed with methanol/water to give the title compound (8.72 g, 58%) as a brown solid. $\delta_H$ (CDCl$_3$) 4.33-4.40 (2H, m), 4.45-4.52 (2H, m), 6.41 (2H, br.s), 6.88 (1H, d, J 8.7 Hz), 7.25 (1H, dd, J 8.7, 2.1 Hz), 7.51 (1H, d, J 2.1 Hz). LCMS (ES+) 275 (M+H)+.

Intermediate 31

7-Bromo-2,3-dihydro-benzo[1,4]oxazine-4-carbothioic acid amide

A solution of Intermediate 19 (1.0 g, 4.7 mmol) in THF (10 mL) was added to thiocarbonyldiimidazole (1.2 g, 5.8 mmol) and the mixture heated to 120° C. under microwave irradiation for 20 minutes. After cooling to r.t., it was poured into methanolic ammonia (10 mL of a 7M solution, 70 mmol) and stirred at r.t. over the weekend. It was concentrated in vacuo, and the residue triturated with water and Et$_2$O followed by 1M hydrochloric acid and Et$_2$O to give the title compound (0.75 g, 58%) as a cream solid. $\delta_H$ (DMSO-d$_6$) 4.16-4.35 (4H, m), 7.07 (1H, dd, J 8.9, 2.3 Hz), 7.15 (1H, d, J 2.3 Hz), 7.39 (1H, d, J 8.9 Hz). LCMS (ES+) 275 (M+H)+.

Intermediate 32

3-Bromo-6,6-dimethyl-azepane-2,4-dione

To a solution of 6,6-dimethylazepan-2,4-dione (10.0 g, 64.5 mmol) in glacial acetic acid (160 mL) was added bromine (3.3 mL, 64.5 mmol) dropwise. The reaction mixture was stirred at r.t. for 1 h. The resulting precipitate was collected by filtration to give the title compound (16.83 g, quantitative) as a white solid. $\delta_H$ (DMSO-$d_6$) 0.86 (3H, s), 0.99 (3H, s), 2.31 (1H, d, J 11.7 Hz), 2.73 (1H, d, J 11.7 Hz), 2.75 (1H, dd, J 15.2, 6.6 Hz), 3.31 (1H, dd, J 15.2, 6.6 Hz), 5.77 (1H, s), 8.40 (1H, t, J 6.2 Hz). LCMS (ES+) 234/236 (M+H)$^+$.

Intermediate 33

2-Methyl-1-[4-(4,4,5,5-tetramethyl-[1,3,2]dioxaborolan-2-yl)-pyrazol-1-yl]-propan-2-ol A mixture of 4-(4,4,5,5-tetramethyl-1,3,2-dioxaborolan-2-yl)-1H-pyrazole (1.5 g, 7.73 mmol) and cesium carbonate (0.499 g, 1.34 mmol) in isobutylene oxide (15 mL) was heated to 120° C. under microwave irradiation for 30 minutes. It was cooled to r.t., filtered and concentrated in vacuo to give the title compound (1.79 g, 87%) as a cream solid. $\delta_H$ (CDCl$_3$) 1.15 (6H, s), 1.33 (12H, s), 3.97 (1H, s), 4.07 (2H, s), 7.69 (1H, s), 7.82 (1H, s). LCMS (ES+) 269/269 (M+H)$^+$.

Intermediate 34

2-[4-(4,4,5,5-Tetramethyl-[1,3,2]dioxaborolan-2-yl)-pyrazol-1-yl]-ethanol

4-Pyrazoleboronic acid pinacol ester (0.25 g, 1.29 mmol), ethylene carbonate (0.125 g, 1.42 mmol) and sodium hydroxide (5 mg, 0.13 mmol) were dissolved in DMF (1 mL) and the reaction mixture was heated to reflux for 2½ h. It was cooled to r.t. before addition of activated charcoal (25 mg). The resulting suspension was stirred at r.t. for 1 h and then filtered through celite, washed with DMF (6 mL) and concentrated in vacuo to give the title compound (0.26 g, 85%) as a yellow oil. LCMS (ES+) 239.18 (M+H)$^+$.

Intermediate 35

1-Methoxy-3-[4-(4,4,5,5-tetramethyl-[1,3,2]dioxaborolan-2-yl)-pyrazol-1-yl]-propan-2-ol A mixture of 4-pyrazoleboronic acid pinacol ester (4.24 g, 21.9 mmol) and glycidyl methyl ether (7.94 g, 76.6 mmol) was heated to 98° C. for 4 h. It was cooled to r.t. and concentrated in vacuo to give the title compound (6.7 g, quantitative) as a yellow oil. $\delta_H$ (CDCl$_3$) 1.32 (12H, s), 3.37 (3H, s), 3.12-3.54 (3H, m), 4.08-4.37 (3H, m), 7.73 (1H, s), 7.80 (1H, s).

Intermediate 36

1-Allyl-4-(4,4,5,5-tetramethyl-[1,3,2]dioxaborolan-2-yl)-1H-pyrazole

A mixture of 4-pyrazoleboronic acid pinacol ester (3.0 g, 15.6 mmol), allyl bromide (6.9 g, 77 mmol) and sodium bis(trimethylsilyl)amide (20.5 mL of a 1.5N solution in THF, 30.7 mmol) in THF (20 mL) was heated to 70° C. overnight. After cooling to r.t. the reaction was quenched with water (15 mL) and extracted with EtOAc (2×30 mL). The combined organic fractions were washed with brine (50 mL), dried (MgSO$_4$) and concentrated in vacuo to give the title compound (3.4 g, 94%) as a yellow oil. $\delta_H$ (CDCl$_3$) 1.20 (12H, s), 4.61-4.67 (2H, m), 5.06-5.24 (2H, m), 5.79-6.01 (1H, m), 7.60 (1H, s), 7.69 (1H, s).

Intermediate 37

1-(4-Bromo-1H-pyrazol-1-yl)-3-methoxypropan-2-ol

A solution of 4-bromopyrazole (200 mg, 1.36 mmol) in methyl glycidyl ether (510 mg, 5.79 mmol) was heated at 100° C. for 70 minutes. After cooling to r.t., the excess methyl glycidyl ether was removed in vacuo to give the title compound (165 mg, 52%) as a clear yellow liquid. $\delta_H$ (CDCl$_3$) 3.21-3.24 (1H, m), 3.31-3.35 (2H, m), 3.38 (3H, s), 4.08-4.30 (3H, m), 7.47-7.50 (2H, m). LCMS (ES+) 235, 237 (M+H)$^+$.

Intermediate 38 and Intermediate 39

2-Bromo-6-[(Z)-2-methoxyvinyl]pyridine and 2-Bromo-6-[(E)-2-methoxyvinyl]pyridine To a suspension of (methoxymethyl)triphenylphosphonium chloride (0.345 g, 1.08 mmol) in THF (5 mL) at −10° C. was added LDA (0.6 mL of a 1.8M solution in heptane, 1.08 mmol). The mixture was stirred at −10° C. for 1 h before addition of a solution of 6-bromo-2-pyridine carboxaldehyde (0.10 g, 0.54 mmol) in THF (3 mL), and was then allowed to warm to r.t. It was partitioned between water and Et$_2$O. The aqueous fraction was separated and extracted twice more with Et$_2$O. The combined organic fractions were dried (MgSO$_4$), concentrated in vacuo and purified by chromatography (SiO$_2$, heptane, followed by heptane:EtOAc 20:1, followed by heptane:EtOAc 10:1) to give the title compounds as colourless oils.

Intermediate 37

(0.39 g, 34%) $\delta_H$ (CDCl$_3$) 3.85 (3H, s), 5.49 (1H, d, J 7.2 Hz), 6.38 (1H, d, J 7.2 Hz), 7.20 (1H, d, J 7.9 Hz), 7.45 (1H, t, J 8.1 Hz), 7.88 (1H, d, J 7.9 Hz). LCMS (ES+) 214/216 (M+H)$^+$.

Intermediate 38

(0.33 g, 29%) $\delta_H$ (CDCl$_3$) 3.73 (3H, s), 5.78 (1H, d, J 12.6 Hz), 6.98 (1H, d, J 7.5 Hz), 7.16 (1H, d, J 7.2 Hz), 7.37 (1H, t, J 7.7 Hz), 7.61 (1H, d, J 12.6 Hz). LCMS (ES+) 214/216 (M+H)$^+$.

Intermediate 40

6-Bromo-7-methyl-4H-benzo[1,4]oxazin-3-one

Prepared following the procedure for Intermediate 6 using 2-amino-4-bromo-5-methylphenol (4.73 g, 23.4 mmol), triethylamine (3.6 mL, 25.8 mmol) and chloroacetyl chloride (1.8 mL, 23.4 mmol) in THF (120 mL) followed by sodium hydride (1.9 g of a 60% suspension in oil, 49.2 mmol) to give the title compound (4.12 g, 73%) as a beige solid. $\delta_H$ (DMSO-$d_6$) 2.23 (3H, s), 4.57 (2H, s), 6.97 (1H, s), 7.04 (1H, s), 10.72 (1H, s).

Intermediate 41

6-Bromo-7-methyl-3,4-dihydro-2H-benzo[1,4]oxazine

Prepared following the procedure for Intermediate 13 using Intermediate 40 (4.12 g, 17.04 mmol) and borane-THF (22 mL of a 1M solution in THF, 22 mmol) in THF (100 mL) to give the title compound (4.1 g, quantitative) as an orange solid. $\delta_H$ (DMSO-d$_6$) 2.13 (3H, s), 3.18-3.29 (2H, m), 4.04-4.14 (2H m), 5.82 (1H, br.s), 6.62 (1H, s), 6.73 (1H, s).

Intermediates 42 and 43 were prepared following the procedure for Example 56.

Intermediate 42

7-Methyl-6-(1-methyl-1H-pyrazol-4-yl)-3,4-dihydro-2H-benzo[1,4]oxazine

Using Intermediate 41 (0.2 g, 0.88 mmol), 1-methyl-4-(4,4,5,5-tetramethyl-1,3,2-dioxaboralan-2-yl)-1H-pyrazole (0.365 g, 1.75 mmol), potassium phosphate (0.466 g, 2.2 mmol) and tetrakis(triphenylphosphine)palladium(0) (catalytic amount) in THF (3.7 mL) and water (1.3 mL) heated to 100° C. under microwave irradiation for 30 minutes. Purification by prep HPLC gave the title compound (87 mg, 38%) as a cream solid. $\delta_H$ (CDCl$_3$) 2.24 (3H, s), 3.39-3.43 (2H, m), 3.65 (1H, s), 3.93 (3H, s), 4.23-4.27 (2H, m), 6.58 (1H, s), 6.67 (1H, s), 7.36 (1H, s), 7.52 (1H, s). LCMS (ES+) 230.13 (M+H)$^+$.

Intermediate 43

6-(6-Methoxy-pyridin-3-yl)-7-methyl-3,4-dihydro-2H-benzo[1,4]oxazine

Using Intermediate 41 (0.228 g, 1 mmol), 2-methoxy-5-pyridineboronic acid (0.306 g, 2 mmol), potassium phosphate (0.53 g, 2.5 mmol) and tetrakis(triphenylphosphine)palladium(0) (catalytic amount) in THF (3.7 mL) and water (1.3 mL) heated to 100° C. under microwave irradiation for 30 minutes. Purification by prep HPLC gave the title compound as a yellow oil (0.104 g, 41%). $\delta_H$ (CDCl$_3$) 2.12 (3H, s), 3.41-3.45 (2H, m), 3.97 (3H, s), 4.25-4.29 (2H, m), 6.47 (1H, s), 6.70 (1H, s), 6.76 (1H, dd, J 8.5, 0.6 Hz), 7.51 (1H, dd, J 8.5, 2.4 Hz), 8.08 (1H, dd, J 2.4, 0.8 Hz). LCMS (ES+) 255.14 (M+H)$^+$.

Intermediate 44

2-[4-(7-Methyl-3,4-dihydro-2H-benzo[1,4]oxazin-6-yl)-pyrazol-1-yl]-ethanol

A mixture of Intermediate 41 (0.304 g, 1.33 mmol), Intermediate 34 (0.476 g, 2 mmol), potassium acetate (0.157 g, 1.6 mmol) and bis(tris-tert-butylphosphino)palladium(0) (0.041 g, 0.08 mmol) in DMF (3 mL) was heated to 140° C. for 1 h. After cooling to r.t. activated charcoal (47 mg) was added, and the resulting suspension stirred at r.t. for 2 h. It was filtered through celite, washed with DMF (5 mL) and then concentrated in vacuo. The residue was purified by prep HPLC then dissolved in DCM (15 mL), washed with aqueous potassium carbonate and the organic fraction concentrated in vacuo to give the title compound (73 mg, 21%) as a yellow oil. $\delta_H$ (CDCl$_3$) 2.24 (3H, s), 3.39-3.43 (2H, m), 3.91-3.95 (1H, m), 4.01-4.06 (2H, m), 4.22-4.30 (4H, m), 6.58 (1H, s), 6.68 (1H, s), 7.44 (1H, s), 7.57 (1H, d, J 0.4 Hz). LCMS (ES+) 260.16 (M+H)$^+$.

Intermediate 45

7,7-Dimethyl-2-[6-(4,4,5,5-tetramethyl-[1,3,2]dioxaborolan-2-yl)-2,3-dihydrobenzo[1,4]oxazin-4-yl]-5,6,7,8-tetrahydro-thiazolo[5,4-c]azepin-4-one A mixture of Example 67 (0.15 g, 0.37 mmol), bis(pinacolato)diboron (130 mg, 0.55 mmol), 1,2'-[bis(diphenylphosphino)ferrocene]dichloropalladium(II) dichloromethane complex (60 mg, 0.07 mmol) and potassium acetate (54 mg, 0.55 mmol) in THF (4 mL) was heated to 110° C. under microwave irradiation for 20 minutes. After cooling to r.t. it was concentrated in vacuo and the residue was triturated with Et$_2$O (5 mL) and water (5 mL). The resulting solid was washed with Et$_2$O (2×30 mL). The combined organics were washed with water (50 mL) and brine (50 mL), dried (MgSO$_4$), concentrated in vacuo, triturated with heptane (2×20 mL) and dried in vacuo to give the title compound (90 mg, 53%) as a beige solid. LCMS (ES+) 456 (M+H)$^+$.

Intermediate 46

5,5-Dimethyl-2-[6-(4,4,5,5-tetramethyl-[1,3,2]dioxaborolan-2-yl)-2,3-dihydrobenzo[1,4]oxazin-4-yl]-5,6-dihydro-4H-benzothiazol-7-one A mixture of Example 1 (1.0 g, 2.54 mmol), bis(pinacolato)diboron (969 mg, 3.81 mmol), 1,2'-[bis(diphenylphosphino)ferrocene]dichloropalladium(II) dichloromethane complex (415 mg, 0.51 mmol) and potassium acetate (374 mg, 3.81 mmol) in THF (15 mL) was heated to 125° C. under microwave irradiation for 30 minutes. A second portion of catalyst (415 mg, 0.51 mmol) was added and heating continued for a further 40 minutes. After cooling to r.t. it was concentrated in vacuo, suspended in tert-butyl methyl ether (40 mL) and filtered through celite. The filtrate was washed with water (40 mL) and concentrated in vacuo. The residue was suspended in heptane, sonicated, removed by filtration and dried in vacuo to give the title compound (0.66 g, 59%) as a red/brown solid. LCMS (ES+) 441 (M+H)$^+$.

Intermediate 47

2-[6-(1-Allyl-1H-pyrazol-4-yl)-2,3-dihydro-benzo[1,4]oxazin-4-yl]-7,7-dimethyl-5,6,7,8-tetrahydro-thiazolo[5,4-c]azepin-4-one Using Example 67 (0.95 g, 2.32 mmol), Intermediate 36 (1.08 g, 4.64 mmol), tetrakis(triphenylphosphine)palladium(0) (549 mg, 0.46 mmol), potassium phosphate (1.47 g, 6.9 mmol) and tetra-n-butylammonium bromide (749 mg, 2.32 mmol) in THF (10 mL) and water (3 mL) heated to 140° C. under microwave irradiation for 20 minutes. Purification by column chromatography (SiO$_2$, gradient elution 10% EtOAc in DCM increasing to 100% EtOAc) gave the title compound (410 mg, 41%) as a yellow oil. $\delta_H$ (CDCl$_3$) 1.12 (6H, s), 2.86 (2H, s), 3.13 (2H, d, J 5.3 Hz), 4.08-4.19 (2H, m), 4.27-4.35 (2H, m), 4.73-4.81 (2H, m), 5.23-5.35 (2H, m), 5.83 (1H, br.s), 5.97-6.16 (1H, m), 6.93 (1H, d, J 8.3 Hz), 7.15 (1H, dd, J 8.5, 2.1 Hz), 7.59 (1H, s), 7.73 (1H, s), 8.03 (1H, d, J 2.1 Hz).

Intermediate 48

2-[6-(1-Allyl-1H-pyrazol-4-yl)-2,3-dihydro-benzo[1,4]oxazin-4-yl]-5,5-dimethyl-5,6-dihydro-4H-benzothiazol-7-one Using Example 1 (1.1 g, 2.76 mmol), Intermediate 36 (1.29 g, 5.53 mmol), tetrakis(triphenylphosphine)palladium(0) (661 mg, 0.55 mmol), potassium phosphate (1.76 g, 8.3 mmol) and tetra-n-butylammonium bromide (894 mg, 2.76 mmol) in THF (10 mL) and water (5 mL) heated to 140° C. under microwave irradiation for 20 minutes. Purification by column chromatography (SiO$_2$, gradient elution 10% EtOAc in heptane increasing to 100% EtOAc) gave the title compound (400 mg, 34%) as a yellow oil. δ$_H$ (CDCl$_3$) 1.16 (6H, s), 2.43 (2H, s), 2.77 (2H, s), 4.21-4.27 (2H, m), 4.31-4.38 (2H, m), 4.74-4.82 (2H, m), 5.23-5.36 (2H, m), 5.98-6.16 (1H, m), 6.96 (1H, d, J 8.5 Hz), 7.20 (1H, dd, J 8.5, 2.1 Hz), 7.60 (1H, s), 7.73 (1H, s), 7.99 (1H, d, J 1.9 Hz).

Example 1

Method A 2-(6-Bromo-2,3-dihydrobenzo[1,4]oxazin-4-yl)-5,5-dimethyl-5,6-dihydro-4H-benzothiazol-7-one Intermediate 13 (2 g, 9.4 mmol) and 1,1'-thiocarbonyldiimidazole (3.3 g, 18.8 mmol) were combined in THF (16 ml) and heated to 125° C. under microwave irradiation for 15 min. The mixture was cooled to r.t., reduced in vacuo, and ammonia (50 ml of a 7N solution in methanol, 0.35 mol) was added. It was stirred for 2 h, then concentrated in vacuo. The residue was partitioned between EtOAc (100 ml) and 2N HCl (100 ml). The organics were washed with brine (100 ml), dried (MgSO$_4$), filtered and concentrated in vacuo. The residue was triturated with Et$_2$O and heptane to give a yellow solid. Of this material, 0.5 g (1.8 mmol) was combined with Intermediate 1 (0.69 g, 3.1 mmol) and DIPEA (0.6 mL, 3.4 mmol) in THF (18 mL) and heated to 140° C. under microwave irradiation for 30 min. After cooling to r.t. the mixture was partitioned between EtOAc (130 mL) and water (130 mL). The organics were washed with water (150 mL) and brine (100 mL), dried (MgSO$_4$), filtered and concentrated in vacuo. The resulting crude material was purified by prep HPLC to yield the title compound as an off-white solid (166 mg, 23%). δ$_H$ (CDCl$_3$) 1.16 (6H, s), 2.44 (2H, s), 2.79 (2H, s), 4.07-4.17 (2H, m), 4.27-4.38 (2H, m), 6.84 (1H, d, J 8.7 Hz), 7.17 (1H, dd, J 8.7, 2.3 Hz), 8.22 (1H, d, J 2.3 Hz). LCMS (ES+) 393 (M+H)$^+$.

Example 2

2-(7-Bromo-2,3-dihydrobenzo[1,4]oxazin-4-yl)-5,5-dimethyl-5,6-dihydro-4H-benzothiazol-7-one Following Method A using Intermediate 19 (0.8 g, 3.7 mmol) and 1,1'-thiocarbonyldiimidazole (1.0 g, 5.6 mmol) in THF (20 ml) followed by ammonia (20 ml of a 7N solution in methanol, 0.14 mol), then Intermediate 1 (0.45 g, 2.1 mmol) and DIPEA (0.5 mL, 2.8 mmol) in THF (16 mL). The crude material was purified by prep HPLC to yield the title compound as an off-white solid (160 mg, 29%). δ$_H$ (CDCl$_3$) 1.15 (6H, s), 2.43 (2H, s), 2.76 (2H, s), 4.15 (2H, m), 4.30-4.38 (2H, m), 7.04-7.15 (2H, m), 7.89 (1H, d, J 8.7 Hz). LCMS (ES+) 393 (M+H)$^+$.

Example 3

Method B 5,5-Dimethyl-2-(6-nitro-2,3-dihydrobenzo[1,4]oxazin-4-yl)-5,6-dihydro-4H-benzothiazol-7-one Intermediate 14 (1.08 g, 6 mmol), Intermediate 3 (1.0 g, 4 mmol), sodium tert-butoxide (0.96 g, 10 mmol), (Bu$^t$)$_3$PBF$_4$ (0.23 g, 0.8 mmol) and palladium(II) acetate (90 mg, 0.4 mmol) in THF (18 mL) were heated to 100° C. under microwave irradiation for 50 min. After cooling to r.t. the mixture was partitioned between EtOAc (100 mL) and water (100 mL). The organics were washed with 2N aqueous sodium hydroxide (50 mL), water (150 mL) and brine (100 mL), dried (MgSO$_4$), filtered and concentrated in vacuo. The resulting crude material was purified by prep HPLC to yield the title compound as a yellow solid (45 mg, 3%). δ$_H$ (CDCl$_3$) 1.17 (6H, s), 2.46 (2H, s), 2.84 (2H, s), 4.08-4.16 (2H, m), 4.43-4.50 (2H, m), 7.05 (1H, d, J 9.0 Hz), 7.97 (1H, dd, J 8.9, 2.6 Hz), 9.28 (1H, d, J 2.6 Hz). LCMS (ES+) 360 (M+H)$^+$.

Example 4

5,5-Dimethyl-2-(7-nitro-2,3-dihydrobenzo[1,4]oxazin-4-yl)-5,6-dihydro-4H-benzothiazol-7-one Following Method B, using Intermediate 17 (0.8 g, 4.4 mmol), Intermediate 3 (1.16 g, 4.4 mmol), sodium tert-butoxide (1.02 g, 10.7 mmol), (Bu$^t$)$_3$PBF$_4$ (0.13 g, 4.4 mmol) and palladium(II) acetate (50 mg, 0.2 mmol) in DME (15 mL) heated to 140° C. under microwave irradiation for 70 min. The crude material was purified by prep HPLC to yield the title compound as a pale orange solid (18 mg, 1%). δ$_H$ (CDCl$_3$) 1.17 (6H, s), 2.47 (2H, s), 2.83 (2H, s), 4.11-4.20 (2H, m), 4.40-4.48 (2H, m), 7.82-7.92 (2H, m), 8.46 (1H, d, J 8.9 Hz). LCMS (ES+) 360 (M+H)$^+$.

Example 5

4-(5,5-Dimethyl-7-oxo-4,5,6,7-tetrahydrobenzothiazol-2-yl)-3,4-dihydro-2H-benzo[1,4]oxazine-7-carboxylic acid methyl ester Following Method B, using Intermediate 20 (100 mg, 0.52 mmol), Intermediate 3 (136 mg, 0.52 mmol), sodium tert-butoxide (120 mg, 1.26 mmol), (Bu$^t$)$_3$PBF$_4$ (15 mg, 0.05 mmol) and palladium(II) acetate (6 mg, 0.03 mmol) in DME (3.5 mL) heated to 140° C. under microwave irradiation for 150 min. The crude material was purified by prep HPLC to yield the title compound as an off-white solid (14 mg, 7%). δ$_H$ (CDCl$_3$) 1.16 (6H, s), 2.44 (2H, s), 2.80 (2H, s), 3.91 (3H, s), 4.14-4.23 (2H, m), 4.34-4.43 (2H, m), 7.61-7.69 (2H, m), 8.16 (1H, d, J 9.4 Hz). LCMS (ES+) 373 (M+H)$^+$.

Example 6

2-(6-Hydroxy-2,3-dihydrobenzo[1,4]oxazin-4-yl)-5,5-dimethyl-5,6-dihydro-4H-benzothiazol-7-one Following Method B, using 3,4-dihydro-2H-benzo[1,4]oxazin-6-ol hydrobromide (130 mg, 0.86 mmol), sodium tert-butoxide (188 mg, 1.9 mmol), Intermediate 3 (150 mg, 0.57 mmol), (Bu$^t$)$_3$PBF$_4$ (17 mg, 0.05 mmol) and palladium(II) acetate (7 mg, 0.028 mmol) in DME (3.5 mL) heated to 140° C. under microwave irradiation for 20 min. The crude material was purified by prep HPLC to give the title compound as a yellow solid (30 mg, 16%). δ$_H$ (CDCl$_3$) 1.13 (6H, s), 2.46 (2H, s), 2.76 (2H, s), 4.19-4.24 (2H, m), 4.25-4.30 (2H, m), 6.63 (1H, dd, J 8.7, 2.8 Hz), 6.81-6.86 (1H, m), 7.50 (1H, d, J 2.6 Hz). LCMS (ES+) 331 (M+H)$^+$.

Example 7

2-(6-Chloro-2,3-dihydrobenzo[1,4]oxazin-4-yl)-5,5-dimethyl-5,6-dihydro-4H-benzothiazol-7-one Following Method B, using Intermediate 15 (0.7 g, 0.4 mmol), Intermediate 3 (0.11 g, 0.4 mmol), sodium tert-butoxide (0.97 g, 1.0 mmol), (Bu$^t$)$_3$PBF$_4$ (12 mg, 0.04 mmol) and palladium(II) acetate (5 mg, 0.02 mmol) in DME (4 ml) heated to 140° C. under microwave irradiation for 15 min.

The crude material was purified by prep HPLC to yield the title compound as a light brown solid (14 mg, 1%). $\delta_H$ (CDCl$_3$) 1.16 (6H, s), 2.44 (2H, s), 2.79 (2H, s), 4.07-4.17 (2H, m), 4.30-4.38 (2H, m), 6.84-6.93 (1H, m), 7.03 (1H, dd, J 8.7, 2.3 Hz), 8.12 (1H, d, J 2.6 Hz). LCMS (ES+) 349 (M+H)$^+$.

Example 8

5,5-Dimethyl-2-(6-phenyl-2,3-dihydrobenzo[1,4] oxazin-4-yl)-5,6-dihydro-4H-benzothiazol-7-one Following Method B, using Intermediate 3 (199 mg, 0.728 mmol), Intermediate 16 (120 mg, 0.56 mmol), sodium tert-butoxide (134 mg, 14 mmol), (Bu$^t$)$_3$PBF$_4$ (32 mg, 0.11 mmol) and palladium(II) acetate (13 mg, 0.056 mmol) in DME (10 mL) heated to 120° C. under microwave irradiation for 40 min. The crude material was purified by prep HPLC to give the title compound as a brown solid (8 mg, 3%). $\delta_H$ (MeOD-d$_4$) 1.08 (6H, s), 2.35 (2H, s), 2.71 (2H, s), 4.15-4.21 (2H, m), 4.27-4.33 (2H, m), 6.95 (1H, d, J 8.7 Hz), 7.22-7.53 (6H, m), 8.01 (1H, d, J 2.1 Hz). LCMS (ES+) 391 (M+H)$^+$.

Example 9

2-(2,3-Dihydropyrido[2,3-b][1,4]oxazin-1-yl)-5,5-dimethyl-5,6-dihydro-4H-benzothiazol-7-one Following Method B, using Intermediate 3 (100 mg, 0.35 mmol), Intermediate 22 (68 mg, 0.5 mmol), sodium tert-butoxide (92 mg, 0.96 mmol), (Bu$^t$)$_3$PBF$_4$ (11 mg, 0.35 mmol) and palladium(II) acetate (5 mg, 0.02 mmol) in DME (4 mL) heated to 120° C. under microwave irradiation for 20 min. The crude material was purified by prep HPLC to give the title compound as a pale yellow solid (11 mg, 7%). $\delta_H$ (CDCl$_3$) 1.16 (6H, s), 2.45 (2H, s), 2.79 (2H, s), 4.08-4.18 (2H, m), 4.47-4.59 (2H, m), 7.02 (1H, dd, J 8.1, 4.7 Hz), 8.02 (1H, dd, J 4.9, 1.7 Hz), 8.58 (1H, dd, J 8.1, 1.5 Hz). LCMS (ES+) 316 (M+H)$^+$.

Example 10

7,7-Dimethyl-2-(7-nitro-2,3-dihydrobenzo[1,4]oxazin-4-yl)-5,6,7,8-tetrahydro-thiazolo[5,4-c]azepin-4-one Following Method B, using Intermediate 5 (152 mg, 0.55 mmol), sodium tert-butoxide (74 mg, 0.77 mmol), Intermediate 17 (100 mg, 0.55 mmol), (Bu$^t$)$_3$PBF$_4$ (31 mg, 0.11 mmol) and palladium(II) acetate (12 mg, 0.055 mmol) in DME (2 mL) heated under microwave irradiation to 130° C. for 20 min followed by 140° C. for 20 min. The crude material was purified by prep HPLC to give the title compound as a deep yellow solid (21 mg, 10%). $\delta_H$ (CDCl$_3$) 1.13 (6H, s), 2.91 (2H, s), 3.16 (2H, d, J 5.3 Hz), 4.06-4.13 (2H, m), 4.37-4.43 (2H, m), 7.82-7.84 (1H, m), 7.85-7.88 (1H, m), 8.42 (1H, dd, J 8.7, 0.9 Hz). LCMS (ES+) 375 (M+H)$^+$.

Example 11

7,7-Dimethyl-2-(6-hydroxy-2,3-dihydrobenzo[1,4] oxazin-4-yl)-5,6,7,8-tetrahydro-thiazolo[5,4-c] azepin-4-one Following Method B, using 3,4-dihydro-2H-benzo[1,4] oxazin-6-ol hydrobromide (84 mg, 3.6 mmol), sodium tert-butoxide (125 mg, 1.3 mmol), Intermediate 5 (100 mg, 3.6 mmol), (Bu$^t$)$_3$PBF$_4$ (31 mg, 0.11 mmol) and palladium(II) acetate (12 mg, 0.055 mmol) in DME (2 mL) heated to 140° C. for 20 min under microwave irradiation. The crude material was purified by prep HPLC to give the title compound as a white solid (5 mg, 0.4%). $\delta_H$ (CDCl$_3$) 1.11 (6H, s), 2.85 (2H, s), 3.12 (2H, s), 4.07-4.19 (2H, m), 4.20-4.30 (2H, m), 6.53-6.62 (1H, m), 6.80 (1H, d, J 8.85 Hz), 7.34-7.40 (1H, m). LCMS (ES+) 346 (M+H)$^+$.

Example 12

2-(6-Amino-2,3-dihydrobenzo[1,4]oxazin-4-yl)-5,5-dimethyl-5,6-dihydro-4H-benzothiazol-7-one Example 3 (40 mg, 0.1 mmol) and 5% palladium on carbon (6 mg, catalytic) were combined in EtOAc (10 mL) and hydrogenated at atmospheric pressure overnight. The catalyst was removed by filtration and the filtrate evaporated to yield the title compound as a yellow solid (31 mg, 84%). $\delta_H$ (CDCl$_3$) 1.15 (6H, s), 2.42 (2H, s), 2.76 (2H, s), 3.54 (2H, br s), 4.13-4.20 (2H, m), 4.23-4.29 (2H, m), 6.45 (1H, dd, J 8.7, 2.6 Hz), 6.77 (1H, d, J 8.7 Hz), 7.31 (1H, d, J 2.4 Hz). LCMS (ES+) 330 (M+H)$^+$.

Example 13

2-(7-Amino-2,3-dihydrobenzo[1,4]oxazin-4-yl)-5,5-dimethyl-5,6-dihydro-4H-benzothiazol-7-one Using Example 4 (140 mg, 0.4 mmol) and 10% palladium on carbon (28 mg, catalytic) in MeOH (20 mL) and DCM (5 mL) to yield the title compound as a brown solid (103 mg, 80%). $\delta_H$ (CDCl$_3$) 1.14 (6H, s), 2.40 (2H, s), 2.73 (2H, s), 4.13-4.21 (2H, m), 4.26-4.33 (2H, m), 6.23-6.34 (2H, m), 7.57 (1H, d, J 8.5 Hz). LCMS (ES+) 330 (M+H)$^+$.

Example 14

2-(7-Amino-6-chloro-2,3-dihydrobenzo[1,4]oxazin-4-yl)-5,5-dimethyl-5,6-dihydro-4H-benzothiazol-7-one Using Intermediate 23 (50 mg, 0.127 mmol) and 10% palladium on carbon (10 mg, catalytic) in EtOH (25 mL) and MeOH (25 mL). The crude material was purified by prep HPLC to give the title compound as a pale yellow solid (4 mg, 8%). $\delta_H$ (CDCl$_3$) 1.06 (6H, s), 2.33 (2H, s), 2.69 (2H, s), 4.00-4.07 (2H, m), 4.18-4.24 (2H, m), 6.34 (1H, s), 7.71 (1H, s). LCMS (ES+) 364 (M+H)$^+$.

Example 15

4-(5,5-Dimethyl-7-oxo-4,5,6,7-tetrahydrobenzothiazol-2-yl)-3,4-dihydro-2H-benzo[1,4]oxazine-7-carboxylic acid dimethylamide EDC (34 mg, 0.18 mmol), HOBT (3 mg, 0.019 mmol) and dimethylamine (0.21 mL of a 2M solution in THF, 0.42 mmol) were added to a solution of Intermediate 24 (50 mg, 0.14 mmol) in DCM (3 mL). The solution was stirred overnight at r.t. then concentrated in vacuo. The residue was partitioned between EtOAc (10 mL) and water (10 mL), washed with brine, dried (MgSO$_4$) and concentrated in vacuo. The crude material was purified by prep HPLC to give the title compound as a white solid (8 mg, 15%). $\delta_H$ (MeOD-d$_4$) 1.15 (6H, s), 2.45 (2H, s), 2.82 (2H, s), 3.06 (3H, s), 3.10 (3H, s), 4.15-4.24 (2H, m), 4.36-4.43 (2H, m), 7.00-7.14 (2H, m), 8.23 (1H, d, J 12.30 Hz). LCMS (ES+) 386 (M+H)+.

Examples 16 to 19

Prepared in the same manner as Example 15.

Example 16

5,5-Dimethyl-2-[7-(4-methylpiperazin-1-ylcarbonyl)-2,3-dihydrobenzo[1,4]oxazin-4-yl]-5,6-dihydro-4H-benzothiazol-7-one di-acetic acid salt Using Intermediate 24 (50 mg, 0.14 mmol), EDC (34 mg, 0.18 mmol), HOBT (3 mg, 0.019 mmol), 1-methylpiperazine (0.02 mL, 0.18 mmol) and DCM (3 mL). The crude material was purified by prep HPLC to give the title compound as a yellow solid (14 mg, 23%). $\delta_H$ (MeOD-$d_4$) 1.16 (6H, s), 1.95 (6H, s), 2.38 (2H, s), 2.46 (2H, s), 2.48-2.64 (4H, br m), 3.47-3.88 (4H, br m), 4.16-4.23 (2H, m), 4.36-4.43 (2H, m), 7.02-7.11 (2H, m), 8.25 (1H, d, J 9.0 Hz). LCMS (ES+) 441 (M+H)+.

Example 17

4-(5,5-Dimethyl-7-oxo-4,5,6,7-tetrahydrobenzothiazol-2-yl)-3,4-dihydro-2H-benzo[1,4]oxazine-7-carboxylic acid [2-(dimethylamino)ethyl]amide monoacetic acid salt Using Intermediate 24 (50 mg, 0.14 mmol), EDC (34 mg, 0.18 mmol), HOBT (3 mg, 0.019 mmol), N,N-dimethylethylenediamine (0.013 mL, 0.18 mmol) and DCM (3 mL). The crude material was purified by prep HPLC to give the title compound as a white solid (8.2 mg, 14%). $\delta_H$ (MeOD-$d_4$) 1.16 (6H, s), 1.95 (3H, s), 2.46 (2H, s), 2.64 (6H, s), 2.86 (2H, s), 2.96 (2H, t, J 6.2 Hz), 3.65 (2H, t, J 6.2 Hz), 4.16-4.26 (2H, m), 4.35-4.46 (2H, m) 7.45-7.56 (2H, m), 8.28 (1H, d, J 9.2 Hz). LCMS (ES+) 429 (M+H)+.

Example 18

5,5-Dimethyl-2-[7-(pyrrolidin-1-ylcarbonyl)-2,3-dihydrobenzo[1,4]oxazin-4-yl]-5,6-dihydro-4H-benzothiazol-7-one di-acetic acid salt Using Intermediate 24 (50 mg, 0.14 mmol), EDC (34 mg, 0.18 mmol), HOBT (3 mg, 0.019 mmol), pyrrolidine (0.015 mL, 0.182 mmol) and DCM (3 mL). The crude material was purified by prep HPLC to give the title compound as a colourless solid (9.6 mg, 17%). $\delta_H$ (MeOD-$d_4$) 1.16 (6H, s), 1.92 (6H, s), 1.85-2.08 (2H, m), 2.46 (2H, s), 2.83 (2H, s), 3.57 (4H, dt, J 18.8, 6.8 Hz), 4.17-4.24 (2H, m), 4.37-4.43 (2H, m), 7.15-7.22 (2H, m), 8.23 (1H, d, J 8.1 Hz). LCMS (ES+) 412 (M+H)+.

Example 19

4-(5,5-Dimethyl-7-oxo-4,5,6,7-tetrahydrobenzothiazol-2-yl)-3,4-dihydro-2H-benzo[1,4]oxazine-7-carboxylic acid (1-methyl-1H-pyrazol-4-ylmethyl) amide Using Intermediate 24 (50 mg, 0.14 mmol), EDC (34 mg, 0.18 mmol), HOBT (3 mg, 0.019 mmol), C-(1-methyl-1H-pyrazol-4-yl)methylamine (20 mg, 0.18 mmol) and DCM (3 mL). The crude material was purified by prep HPLC to give the title compound as a yellow solid (7 mg, 11%). $\delta_H$ (MeOD-$d_4$) 1.06 (6H, s), 2.34 (2H, s), 2.72 (2H, s), 3.76 (3H, s), 4.00-4.18 (2H, m), 4.25-4.36 (2H, m), 4.31 (2H, s), 7.30-7.48 (4H, m), 8.03 (1H, d, J 9.2 Hz). LCMS (ES+) 452 (M+H)+.

Example 20

N-[4-(5,5-Dimethyl-7-oxo-4,5,6,7-tetrahydro-1,3-benzothiazol-2-yl)-3,4-dihydro-2H-benzo[1,4]oxazin-7-yl]benzenesulfonamide A mixture of Example 13 (46 mg, 0.14 mmol), benzenesulfonyl chloride (0.023 mL, 0.182 mmol) and pyridine (0.022 mL, 0.28 mmol) in DCM (4 mL) was stirred at r.t. for 5 h. The reaction mixture was concentrated in vacuo. Purification by prep HPLC gave the title compound as an off-white solid (23 mg, 35%). $\delta_H$ (CDCl$_3$) 1.14 (6H, s), 2.43 (2H, s), 2.74 (2H, s), 4.08-4.16 (2H, m), 4.26-4.33 (2H, m), 6.64 (1H, dd, J 8.9, 2.4 Hz), 6.80 (1H, d, J 2.4 Hz), 7.02 (1H, s), 7.42-7.61 (3H, m), 7.77-7.87 (3H, m). LCMS (ES+) 470.1 (M+H)+.

Examples 21 to 24

Prepared following the same procedure as Example 20.

Example 21

N-[4-(5,5-Dimethyl-7-oxo-4,5,6,7-tetrahydro-1,3-benzothiazol-2-yl)-3,4-dihydro-2H-benzo[1,4]oxazin-7-yl]methanesulfonamide Using Example 13 (40 mg, 0.122 mmol), methanesulfonyl chloride (0.02 ml, 0.24 mmol) and pyridine (0.05 mL, 0.486 mmol) in DCM (4 mL) stirred at r.t. for 1 day. The crude material was purified by prep HPLC to give the title compound as an off-white solid (20 mg, 40%). $\delta_H$ (CDCl$_3$) 1.15 (6H, s), 2.43 (2H, s), 2.76 (2H, s), 3.04 (3H, s), 4.14-4.19 (2H, m), 4.32-4.39 (2H, m), 6.63 (1H, s), 6.80 (1H, dd, J 8.9, 2.6 Hz), 6.92 (1H, dd, J 2.6 Hz), 7.95 (1H, d, J 8.9 Hz). LCMS (ES+) 408.1 (M+H)+.

Example 22

N-[4-(5,5-Dimethyl-7-oxo-4,5,6,7-tetrahydro-1,3-benzothiazol-2-yl)-3,4-dihydro-2H-benzo[1,4]oxazin-7-yl]benzamide Using Example 13 (46 mg, 0.14 mmol), benzoyl chloride (0.021 mL, 0.182 mmol) and pyridine (0.022 mL, 0.28 mmol) in DCM (4 mL) stirred at r.t. for 5 h. The crude material was purified by prep HPLC to give the title compound as a yellow solid (20 mg, 33%). $\delta_H$ (CDCl$_3$) 1.15 (6H, s), 2.41 (2H, s), 2.76 (2H, s), 4.16-4.22 (2H, m), 4.32-4.38 (2H, m), 7.11 (1H, dd, J 8.9, 2.4 Hz), 7.44-7.61 (4H, m), 7.84-7.93 (3H, m), 7.96 (1H, br s). LCMS (ES+) 434.3 (M+H)+.

Example 23

N-[4-(5,5-Dimethyl-7-oxo-4,5,6,7-tetrahydro-1,3-benzothiazol-2-yl)-3,4-dihydro-2H-benzo[1,4]oxazin-7-yl]nicotinamide Using Example 13 (40 mg, 0.122 mmol), nicotinoyl chloride hydrochloride (32 mg, 0.182 mmol) and pyridine (0.05 mL, 0.486 mmol) in DCM (4 mL) stirred at r.t. for 1 day. The crude material was purified by prep HPLC to give the title compound as a yellow solid (15 mg, 28%). $\delta_H$ (CDCl$_3$) 1.14 (6H, s), 2.40 (2H, s), 2.76 (2H, s), 4.16-4.23 (2H, m), 4.33-4.39 (2H, m), 7.14 (1H, dd, J 8.9, 2.4 Hz), 7.44 (1H, dd, J 7.9, 4.9 Hz), 7.54 (1H, d, J 2.3 Hz), 7.90 (1H, d, J 8.9 Hz), 8.22 (1H, d, J 8.1 Hz), 8.36 (1H, s), 8.77 (1H, d, J 3.8 Hz), 9.11 (1H, s). LCMS (ES+) 435.3 (M+H)+.

Example 24

N-Acetyl-N-[4-(5,5-dimethyl-7-oxo-4,5,6,7-tetrahydro-1,3-benzothiazol-2-yl)-3,4-dihydro-2H-benzo[1,4]oxazin-7-yl]acetamide Using Example 13 (40 mg, 0.122 mmol), acetyl chloride (0.02 mL, 0.24 mmol) and pyridine (0.05 mL, 0.486 mmol) in DCM (4 mL) with stirring at r.t. for 1 day. The crude material was purified by prep HPLC to give the title compound as an off-white solid (12 mg, 24%). $\delta_H$ (CDCl$_3$) 1.16 (6H, s), 2.23 (6H, s), 2.44 (2H, s), 2.78 (2H, s), 4.16-4.22 (2H, m), 4.36-4.42 (2H, m), 6.76 (1H, d obsc.), 6.78 (1H, s obsc.), 8.16 (1H, d, J 9.0 Hz). LCMS (ES+) 414.0 (M+H)+.

Example 25

5,5-Dimethyl-2-[6-(pyridin-3-ylamino)-2,3-dihydrobenzo[1,4]oxazin-4-yl]-5,6-dihydro-4H-benzothiazol-7-one A mixture of Example 7 (50 mg, 0.14 mmol), 3-aminopyridine (0.171 g, 1.8 mmol), sodium tert-butoxide (0.041 g, 0.43 mmol), palladium(II) acetate (0.158 g, 0.70 mmol) and (Bu$^t$)$_3$PBF$_4$ (0.225 g, 0.78 mmol) in THF (3 mL) was heated to 140° C. under microwave irradiation for 80 min. After cooling to r.t., the mixture was concentrated in vacuo. The crude material was purified by prep HPLC to give the title compound as an off-white solid (5 mg, 8.7%). $\delta_H$ (CDCl$_3$) 1.16 (6H, s), 2.44 (2H, s), 2.78 (2H, s), 4.12-4.22 (2H, m), 4.31-4.41 (2H, m), 5.75 (1H, br s), 6.84-6.89 (1H, m), 6.92-6.96 (1H, m), 7.20 (1H, dd, J 8.7, 5.1 Hz), 7.37-7.44 (1H, m), 7.87 (1H, d, J 2.6 Hz), 8.14 (1H, d, J 4.7 Hz), 8.33 (1H, d, J 2.8 Hz). LCMS (ES+) 407.0 (M+H)+.

Examples 26 to 41

Prepared following the same procedure as Example 25.

Example 26

5,5-Dimethyl-2-(6-phenylamino-2,3-dihydrobenzo[1,4]oxazin-4-yl)-5,6-dihydro-4H-benzothiazol-7-one Using Example 7 (40 mg, 0.11 mmol), aniline (0.040 mL, 0.460 mmol), sodium tert-butoxide (28 mg, 028 mmol), palladium(II) acetate (4 mg, 0.010 mmol) and (Bu$^t$)$_3$PBF$_4$ (8 mg, 0.022 mmol) in DMF (3 mL) heated to 140° C. under microwave irradiation, for 40 min. The crude material was purified by prep HPLC to give the title compound as an off-white solid (7 mg, 15%). $\delta_H$ (CDCl$_3$) 1.14 (6H, s), 2.42 (2H, s), 2.75 (2H, s) 4.13-4.20 (2H, m), 4.29-4.35 (2H, m), 5.61 (1H, br s), 6.80-6.93 (3H, m), 7.00-7.05 (2H, m), 7.23-7.31 (2H, m), 7.77 (1H, d, J 2.3 Hz). LCMS (ES+) 406 (M+H)+.

Example 27

5,5-Dimethyl-2-[6-(morpholin-4-yl)-2,3-dihydrobenzo[1,4]oxazin-4-yl]-5,6-dihydro-4H-benzothiazol-7-one Using Example 7 (50 mg, 0.14 mmol), morpholine (1.2 mL, 1.15 mmol), sodium tert-butoxide (41 mg, 0.43 mmol), palladium(II) acetate (2 mg, 0.007 mmol) and (Bu$^t$)$_3$PBF$_4$ (0.004 g, 0.014 mmol) in THF (3 mL) heated to 140° C. under microwave irradiation, for 60 min. The crude material was purified by prep HPLC to give the title compound as an off-white solid (5 mg, 11%). $\delta_H$ (CDCl$_3$) 1.15 (6H, s), 2.43 (2H, s), 2.75 (2H, s), 3.04-3.12 (4H, m), 3.83-3.91 (4H, m), 4.20-4.25 (2H, m), 4.26-4.31 (2H, m), 6.70 (1H, dd, J 9.0, 2.8 Hz), 6.89 (1H, d, J 9.0 Hz), 7.41 (1H, d, J 2.6 Hz). LCMS (ES+) 400 (M+H)+.

Example 28

5,5-Dimethyl-2-[6-(4-methylpiperazin-1-yl)-2,3-dihydrobenzo[1,4]oxazin-4-yl]-5,6-dihydro-4H-benzothiazol-7-one Using Example 7 (50 mg, 0.14 mmol), 1-methylpiperazine (0.12 mL, 1.15 mmol), sodium tert-butoxide (41 mg, 0.43 mmol), palladium(II) acetate (2 mg, 0.007 mmol) and (Bu$^t$)$_3$PBF$_4$ (4 mg, 0.014 mmol) in THF (3 mL) heated to 140° C. under microwave irradiation for 20 min. The crude material was purified by prep HPLC to give the title compound as an off-white solid (6 mg, 8%). $\delta_H$ (CDCl$_3$) 1.15 (6H, s), 2.37 (3H, s), 2.42 (2H, s), 2.56-2.65 (4H, m), 2.75 (2H, s), 3.09-3.18 (4H, m), 4.25-4.31 (2H, m), 4.18-4.25 (2H, m), 6.72 (1H, dd, J 8.9, 2.6 Hz), 6.87 (1H, d, J 8.9 Hz), 7.41 (1H, d, J 2.8 Hz). LCMS (ES+) 413 (M+H)+.

Examples 29 and 30

5,5-Dimethyl-2-[6-(pyrazin-2-ylamino)-2,3-dihydrobenzo[1,4]oxazin-4-yl]-5,6-dihydro-4H-benzothiazol-7-one (29)

2-{6-[Di(pyrazin-2-yl)amino]-2,3-dihydrobenzo[1,4]oxazin-4-yl}-5,5-dimethyl-5,6-dihydro-4H-benzothiazol-7-one (30)

Using Example 12 (40 mg, 0.12 mmol), 2-chloropyrazine (14 mg, 0.14 mmol), sodium tert-butoxide (2.9 mg, 0.3 mmol), (Bu$^t$)$_3$PBF$_4$ (7 mg, 0.02 mmol) and palladium(II) acetate (3 mg, 0.01 mmol) in THF (3 mL) heated to 110° C. under microwave irradiation for 20 min. The crude material was purified by prep HPLC, to give the title compounds as off-white solids. Example 29: (1.5 mg, 3%). $\delta_H$ (CDCl$_3$) 1.09 (6H, s), 2.36 (2H, s), 2.71 (2H, s), 4.06-4.19 (2H, m), 4.23-4.36 (2H, m), 6.40 (1H, br s), 6.87-6.92 (1H, m), 7.02 (1H, dd, J 8.7, 2.4 Hz), 7.87-7.96 (1H, m), 8.04 (1H, d, J 1.3 Hz), 8.13 (1H, s), 8.24 (1H, d, J 2.3 Hz). LCMS (ES+) 407 (M+H)+. Example 30: (2.5 mg, 4%). $\delta_H$ (CDCl$_3$) 1.12 (6H, s), 2.40 (2H, s), 2.68 (2H, s), 4.14-4.24 (2H, m), 4.37-4.48 (2H, m), 6.96-7.02 (1H, m), 7.06-7.12 (1H, m), 8.04 (1H, d, J 2.4 Hz), 8.23-8.32 (2H, m), 8.28 (2H, dd, J 2.6, 1.5 Hz), 8.52 (2H, s). LCMS (ES+) 485 (M+H)+.

Example 31

2-{6-[6-(Dimethylamino)pyridin-3-ylamino]-2,3-dihydrobenzo[1,4]oxazin-4-yl}-5,5-dimethyl-5,6-dihydro-4H-benzothiazol-7-one Using Example 12 (40 mg, 0.12 mmol), 5-bromo-2-(dimethylamino)pyridine (32 mg, 0.17 mmol), sodium tert-butoxide (35 mg, 0.36 mmol), (Bu$^r$)$_3$PBF$_4$ (7 mg, 0.02 mmol) and palladium(II) acetate (6 mg, 0.02 mmol) in THF (4 mL) heated to 140° C. under microwave irradiation for 20 min. After cooling to r.t. the reaction mixture was filtered under reduced pressure and concentrated in vacuo. The crude material was purified by prep HPLC to give the title compound as a green solid (8 mg, 15%). δ$_H$ (CDCl$_3$) 1.09 (6H, s), 2.36 (2H, s), 2.70 (2H, s), 3.06 (6H, s), 4.14-4.20 (2H, m), 4.26-4.32 (2H, m), 6.53 (1H, d, J 8.9 Hz), 6.94 (1H, d, J 8.5 Hz), 7.17 (1H, dd, J 8.5, 2.1 Hz), 7.59 (1H, dd, J 8.9, 2.6 Hz), 7.96 (1H, d, J 2.1 Hz), 8.33 (1H, d, J 2.6 Hz). LCMS (ES+) 450 (M+H)$^+$.

Example 32

5,5-Dimethyl-2-[6-(6-fluoropyridin-2-ylamino)-2,3-dihydrobenzo[1,4]oxazin-4-yl]-5,6-dihydro-4H-benzothiazol-7-one Using Example 12 (65 mg, 0.2 mmol), 2-bromo-5-fluoropyridine (135 mg, 0.76 mmol), sodium tert-butoxide (40 mg, 0.4 mmol), (Bu$^r$)$_3$PBF$_4$ (9 mg, 0.03 mmol) and palladium(II) acetate (4 mg, 0.02 mmol) in THF (4 mL) heated to 130° C. under microwave irradiation for 50 min. The crude material was purified by preparative HPLC to give the title compound as an off-white solid (11 mg, 13%). δ$_H$ (CDCl$_3$) 1.08 (6H, s), 2.36 (2H, s), 2.69 (2H, s), 4.07-4.14 (2H, m), 4.22-4.30 (2H, m), 6.36 (1H, br s), 6.71 (1H, dd, J 9.4, 4.0 Hz), 6.83-6.95 (2H, m), 7.15-7.26 (2H, m), 8.00 (2H, dd, J 8.3, 2.4 Hz). LCMS (ES+) 425 (M+H)$^+$.

Example 33

5,5-Dimethyl-2-[6-(pyridin-2-ylamino)-2,3-dihydrobenzo[1,4]oxazin-4-yl]-5,6-dihydro-4H-benzothiazol-7-one Using Example 1 (40 mg, 0.1 mmol), sodium tert-butoxide (30 mg, 0.3 mmol), (Bu$^r$)$_3$PBF$_4$ (6 mg, 0.02 mmol), palladium (II) acetate (3 mg, 0.01 mmol) and 2-aminopyridine (40 mg, 0.4 mmol) in THF (4 mL) was heated to 140° C. under microwave irradiation for 20 min. The crude material was purified by prep HPLC, then partitioned between EtOAc (50 mL) and saturated sodium hydrogencarbonate solution (50 mL). The organics were dried (MgSO$_4$), filtered and concentrated in vacuo to give the title compound as a yellow solid (5 mg, 12%). δ$_H$ (CDCl$_3$) 1.10 (6H, s), 2.76 (2H, s), 2.42 (2H, s), 4.14-4.21 (2H, m), 4.31-4.38 (2H, m), 6.50 (1H, s), 6.74 (1H, t, J 6.4 Hz), 6.87 (1H, d, J 8.5 Hz), 6.90 (1H, d, J 8.7 Hz), 7.00 (1H, dd, J 8.9, 2.4 Hz), 7.50-7.60 (1H, m), 8.07-8.18 (2H, m). LCMS (ES+) 407.2 (M+H)$^+$.

Example 34

2-[6-(Dimethylamino)-2,3-dihydrobenzo[1,4]oxazin-4-yl]-5,5-dimethyl-5,6-dihydro-4H-benzothiazol-7-one Using Example 1 (40 mg, 0.1 mmol), sodium tert-butoxide (30 mg, 0.3 mmol), (Bu$^r$)$_3$PBF$_4$ (6 mg, 0.02 mmol), palladium (II) acetate (3 mg, 0.01 mmol) and dimethylamine (0.4 mL of a 1M solution in THF, 0.4 mmol) in THF (4 mL) heated to 140° C. under microwave irradiation for 20 minutes. The crude material was purified by prep HPLC, then partitioned between EtOAc (50 mL) and saturated sodium hydrogencarbonate solution (50 mL). The organic portion was dried (MgSO$_4$), filtered and concentrated in vacuo to give the title compound as a yellow solid (6 mg, 17%). δ$_H$ (CDCl$_3$) 1.15 (6H, s), 2.42 (2H, s), 2.76 (2H, s), 3.02 (6H, s), 4.20-4.29 (2H, m), 4.33-4.42 (2H, m), 6.73 (1H, dd, J 8.3, 2.4 Hz), 6.87-6.94 (2H, m), 7.01 (1H, d, J 8.5 Hz), 7.27-7.36 (2H, m), 8.13 (1H, d, J 2.1 Hz). LCMS (ES+) 358 (M+H)$^+$.

Example 35

2-[6-(5-Chloropyridin-2-ylamino)-2,3-dihydrobenzo[1,4]oxazin-4-yl]-5,5-dimethyl-5,6-dihydro-4H-benzothiazol-7-one Using Example 1 (40 mg, 0.1 mmol), sodium tert-butoxide (25 mg, 0.25 mmol), (Bu$^r$)$_3$PBF$_4$ (5.8 mg, 0.02 mmol), palladium(II) acetate (2.4 mg, 0.01 mmol) and 2-amino-5-chloropyridine (53 mg, 0.4 mmol) in THF (4 mL) heated to 140° C. under microwave irradiation for 20 min. The crude material was purified by prep HPLC to give the title compound as an off-white solid (11 mg, 25%). δ$_H$ (CDCl$_3$) 1.15 (6H, s) 2.43 (2H, s), 2.76 (2H, s), 4.13-4.22 (2H, m), 4.30-4.39 (2H, m), 6.50 (1H, br s), 6.76 (1H, d, J 8.9 Hz), 6.91-7.03 (2H, m), 7.45 (1H, dd, J 8.9, 2.4 Hz), 8.10 (1H, d, J 2.3 Hz), 8.13 (1H, d, J 2.4 Hz). LCMS (ES+) 441 (M+H)$^+$.

Example 36

5,5-Dimethyl-2-[7-(pyridin-2-ylamino)-2,3-dihydrobenzo[1,4]oxazin-4-yl]-5,6-dihydro-4H-benzothiazol-7-one Using Example 2 (35 mg, 0.09 mmol), sodium tert-butoxide (28 mg, 0.29 mmol), palladium(II) acetate (2 mg, 0.0049 mmol), (Bu$^r$)$_3$PBF$_4$ (4 mg, 0.009 mmol) and 2-aminopyridine (23 mg, 0.24 mmol) in THF (3 mL) heated to 140° C. under microwave irradiation for 20 min. The crude material was purified by prep HPLC to give the title compound as a yellow solid (6 mg, 16%). δ$_H$ (CDCl$_3$) 1.15 (6H, s), 2.43 (2H, s), 2.76 (2H, s), 4.16-4.22 (2H, m), 4.31-4.37 (2H, m), 6.65 (1H, br s), 6.72-6.82 (1H, m), 6.83-6.93 (2H, m), 7.13 (1H, br s), 7.48-7.58 (1H, m), 7.82 (1H, d, J 8.7 Hz), 8.22 (1H, br s). LCMS (ES+) 407 (M+H)$^+$.

Example 37

5,5-Dimethyl-2-[7-(pyridin-3-ylamino)-2,3-dihydrobenzo[1,4]oxazin-4-yl]-5,6-dihydro-4H-benzothiazol-7-one Using Example 2 (35 mg, 0.09 mmol), sodium tert-butoxide (28 mg, 0.29 mmol), palladium(II) acetate (2 mg, 0.0049 mmol), (Bu$^r$)$_3$PBF$_4$ (4 mg, 0.009 mmol) and 3-aminopyridine (23 mg, 0.24 mmol) in THF (3 mL) heated to 140° C. under microwave irradiation for 20 min. The crude material was purified by prep HPLC to give the title compound as a yellow solid (8 mg, 20%). δ$_H$ (CDCl$_3$) 1.15 (6H, s), 2.19 (1H, br s), 2.42 (2H, s), 2.75 (2H, s), 4.12-4.24 (2H, m), 4.28-4.40 (2H, m), 5.88 (1H, br s), 6.62-6.72 (2H, m), 7.49 (1H, br s), 7.80 (1H, d, J 8.5 Hz), 8.39 (1H, br s). LCMS (ES+) 407 (M+H)$^+$.

Example 38

2-[7-(Dimethylamino)-2,3-dihydrobenzo[1,4]oxazin-4-yl]-5,5-dimethyl-5,6-dihydro-4H-benzothiazol-7-one Using Example 2 (40 mg, 0.1 mmol), sodium tert-butoxide (30 mg, 0.3 mmol), (Bu$^r$)$_3$PBF$_4$ (6 mg, 0.02 mmol), palladium (II) acetate (3 mg, 0.01 mmol) and dimethylamine (0.4 mL of a 1M solution in THF, 0.4 mmol) in THF (4 mL) heated to 140° C. under microwave irradiation for 20 min. The crude material was purified by prep HPLC to give the title compound as a yellow solid (2 mg, 5%). $\delta_H$ (CDCl$_3$) 1.14 (6H, s), 2.41 (2H, s), 2.73 (2H, s), 2.95 (6H, s), 4.14-4.23 (2H, m), 4.26-4.36 (2H, m), 6.33 (2H, br s), 7.67 (1H, br s). LCMS (ES+) 358 (M+H)$^+$.

Example 39

5,5-Dimethyl-2-{7-[(2-methoxyethyl)amino]-2,3-dihydrobenzo[1,4]oxazin-4-yl}-5,6-dihydro-4H-benzothiazol-7-one Using Example 2 (80 mg, 0.2 mmol), sodium tert-butoxide (50 mg, 0.5 mmol), (Bu$^t$)$_3$PBF$_4$ (12 mg, 0.04 mmol), palladium(II) acetate (6 mg, 0.02 mmol) and 2-methoxyethylamine (0.05 mL, 0.6 mmol) in THF (4 mL) heated to 140° C. under microwave irradiation for 20 min. The crude material was purified by prep HPLC to give the title compound as a yellow solid (30 mg, 39%). $\delta_H$ (CDCl$_3$) 1.14 (6H, s), 2.40 (2H, s), 2.72 (2H, s), 3.23-3.30 (2H, m), 3.39 (3H, s), 3.57-3.64 (2H, m), 4.12-4.24 (2H, m), 4.25-4.36 (2H, m), 6.19 (1H, d, J 2.4 Hz), 6.25 (1H, dd, J 8.7, 2.4 Hz), 7.58 (1H, d, J 8.9 Hz). LCMS (ES+) 388.0 (M+H)$^+$.

Example 40

5,5-Dimethyl-2'-{7-[2-(morpholin-4-yl)ethylamino]-2,3-dihydrobenzo[1,4]oxazin-4-yl}-5,6-dihydro-4H-benzothiazol-7-one Using Example 2 (80 mg, 0.2 mmol), sodium tert-butoxide (50 mg, 0.5 mmol), (Bu$^t$)$_3$PBF$_4$ (12 mg, 0.04 mmol), palladium(II) acetate (6 mg, 0.02 mmol) and 4-(2-aminoethyl)morpholine (80 mg, 0.6 mmol) in THF (4 mL) heated to 140° C. under microwave irradiation for 20 min. The crude material was purified by preparative HPLC to give the title compound as a yellow solid (30 mg, 34%). $\delta_H$ (CDCl$_3$) 1.14 (6H, s) 2.40 (2H, s), 2.45-2.54 (4H, m), 2.64 (2H, t, J 6.0 Hz), 2.72 (2H, s), 3.15 (2H, t, J 5.7 Hz), 3.68-3.81 (4H, m), 4.13-4.23 (2H, m), 4.25-4.34 (2H, m), 6.19 (1H, d, J 2.4 Hz), 6.26 (1H, dd, J 8.9, 2.4 Hz), 7.57 (1H, d, J 8.9 Hz). LCMS (ES+) 443 (M+H)$^+$.

Example 41

2-(7-{N-[2-(Dimethylamino)ethyl]-N-methylamino}-2,3-dihydrobenzo[1,4]oxazin-4-yl)-5,5-dimethyl-5,6-dihydro-4H-benzothiazol-7-one Using Example 2 (40 mg, 0.1 mmol), sodium tert-butoxide (25 mg, 0.25 mmol), (Bu$^t$)$_3$PBF$_4$ (6 mg, 0.02 mmol), palladium(II) acetate (3 mg, 0.01 mmol) and N,N,N'-trimethylethylenediamine (0.04 mL, 0.3 mmol) in THF (3 mL) heated to 140° C. under microwave irradiation for 20 min. The crude material was purified by prep HPLC to give the title compound as a yellow solid (12 mg, 29%). $\delta_H$ (CDCl$_3$) 1.14 (6H, s), 2.30 (6H, s), 2.40 (2H, s), 2.44-2.52 (2H, m), 2.73 (2H, s), 2.94 (3H, s), 3.39-3.48 (2H, m), 4.13-4.23 (2H, m), 4.25-4.35 (2H, m), 6.24 (1H, d, J 2.8 Hz), 6.20 (1H, dd, J 9.2, 2.8 Hz), 7.63 (1H, d, J 9.0 Hz). LCMS (ES+) 415 (M+H)$^+$.

Example 42

5,5-Dimethyl-2-{7-[N-(2-methoxyethyl)-N-methylamino]-2,3-dihydrobenzo[1,4]oxazin-4-yl}-5,6-dihydro-4H-benzothiazol-7-one Example 39 (25 mg, 0.06 mmol), sodium triacetoxyborohydride (41 mg, 0.19 mmol) and formaldehyde (1.5 mL of a 37% solution in water, 12.8 mmol) in THF (8 mL) were stirred at r.t. for 5 h. The mixture was concentrated in vacuo and partitioned between EtOAc (50 mL) and saturated sodium hydrogencarbonate solution (50 mL). The combined organic portions were washed with water (50 mL) and brine (50 mL), dried (MgSO$_4$), filtered and concentrated in vacuo to give the title compound as a yellow oil (4 mg, 17%). $\delta_H$ (CDCl$_3$) 1.07 (6H, s), 2.33 (2H, s), 2.66 (2H, s), 2.90 (3H, s), 3.29 (3H, s), 3.38-3.55 (4H, m), 4.06-4.16 (2H, m), 4.19-4.29 (2H, m), 6.20 (1H, d, J 2.6 Hz), 6.27 (1H, dd, J 9.0, 2.8 Hz), 7.55 (1H, d, J 9.0 Hz). LCMS (ES+) 402 (M+H)$^+$.

Example 43

5,5-Dimethyl-2-[6-(1H-pyrazol-4-yl)-2,3-dihydrobenzo[1,4]oxazin-4-yl]-5,6-dihydro-4H-benzothiazol-7-one Example 1 (40 mg, 0.10 mmol), 4,4,5,5-tetramethyl-2-(1H-pyrazol-4-yl)-1,3,2-dioxaborolane (39 mg, 0.2 mmol), sodium carbonate (22 mg, 0.2 mmol) and tetrakis-(triphenylphosphine)palladium(0) (11 mg, 0.009 mmol) in a mixture of THF (3 mL) and water (1 mL) were heated to 140° C. under microwave irradiation for 15 min. After cooling to r.t. the reaction mixture was concentrated in vacuo. The crude material was purified by prep HPLC to give the title compound as an off-white solid (4 mg, 10%). $\delta_H$ (CDCl$_3$/MeOD-d$_4$) 1.09 (6H, s), 2.37 (2H, s), 2.71 (2H, s), 4.12-4.21 (2H, m), 4.24-4.34 (2H, m), 6.91 (1H, d, J 8.5 Hz), 7.16 (1H, dd, J 8.5, 2.1 Hz), 7.75 (2H, br s), 8.02 (1H, d, J 1.9 Hz). LCMS (ES+) 381 (M+H)$^+$.

Examples 44 to 50

Prepared following the same procedure as Example 43.

Example 44

5,5-Dimethyl-2-[6-(pyridin-3-yl)-2,3-dihydrobenzo[1,4]oxazin-4-yl]-5,6-dihydro-4H-benzothiazol-7-one Using Example 1 (40 mg, 0.10 mmol), 3-pyridylboronic acid (41 mg, 0.2 mmol), sodium carbonate (22 mg, 0.2 mmol) and tetrakis(triphenylphosphine)palladium(0) (11 mg, 0.009 mmol) in a mixture of THF (3 mL) and water (1 mL) heated to 140° C. under microwave irradiation for 15 min. The crude material was purified by prep HPLC to give the title compound as an off white solid (5 mg, 13%). $\delta_H$ (CDCl$_3$) 1.09 (6H, s) 2.37 (2H, s), 2.71 (2H, s), 4.12-4.21 (2H, m), 4.27-4.38 (2H, m), 7.01 (1H, 4, J 8.5 Hz), 7.25 (1H, dd, J 8.5, 2.1 Hz), 7.28-7.35 (1H, m), 7.76-7.82 (1H, br d, J 7.9 Hz), 8.14 (1H, d, J 2.1 Hz), 8.52 (1H, br s), 8.77 (1H, br s). LCMS (ES+) 392 (M+H)$^+$.

Example 45

2-{6-[3-(Dimethylamino)phenyl]-2,3-dihydrobenzo[1,4]oxazin-4-yl}-5,5-dimethyl-5,6-dihydro-4H-benzothiazol-7-one Using Example 1 (40 mg, 0.10 mmol), 3-(dimethylamino)phenylboronic acid (34 mg, 0.2 mmol), sodium carbonate (22 mg, 0.2 mmol) and tetrakis(triphenylphosphine)-palladium (0) (11 mg, 0.009 mmol) in a mixture of THF (3 mL) and water (1 mL) heated to 140° C. under microwave irradiation for 15 min. The crude material was purified by prep HPLC to give the title compound as an off-white solid (11 mg, 26%). $\delta_H$ (CDCl$_3$) 1.15 (6H, s), 2.42 (2H, s), 2.76 (2H, s), 3.02 (6H, s), 4.22-4.28 (2H, m), 4.34-4.41 (2H, m), 6.73 (1H, dd, J 8.3, 2.4 Hz), 6.87-6.94 (2H, m), 7.01 (1H, d, J 8.5 Hz), 7.28-7.36 (2H, m), 8.13 (1H, d, J 2.1 Hz). LCMS (ES+) 434 (M+H)$^+$.

Example 46

2-{6-[6-(Dimethylamino)pyridin-3-yl]-2,3-dihydrobenzo[1,4]oxazin-4-yl}-5,5-dimethyl-5,6-dihydro-4H-benzothiazol-7-one Using Example 1 (60 mg, 0.15 mmol), 2-(dimethylamino)pyridin-5-ylboronic acid (75 mg, 0.45 mmol), sodium carbonate (48 mg, 0.45 mmol), tetrakis(triphenylphosphine)-palladium(0) (17 mg, 0.015 mmol) and tetrabutylammonium bromide (145 mg, 0.45 mmol) in a mixture of THF (3 mL) and water (1 mL) heated to 140° C. under microwave irradiation for 15 min. The crude material was purified by prep HPLC to give the title compound as an off-white solid (5 mg, 11%). $\delta_H$ (CDCl$_3$) 1.17 (6H, s), 2.45 (2H, s), 2.79 (2H, s), 3.15 (6H, s), 4.21-4.31 (2H, m), 4.34-4.43 (2H, m), 6.61 (1H, d, J 8.9 Hz), 7.02 (1H, d, J 8.5 Hz), 7.25 (1H, dd, J 8.5, 2.3 Hz), 7.67 (1H, dd, J 8.7, 2.4 Hz), 8.05 (1H, d, J 2.1 Hz), 8.42 (1H, d, J 2.3 Hz). LCMS (ES+) 435 (M+H)$^+$.

Example 47

5,5-Dimethyl-2-(7-phenyl-2,3-dihydrobenzo[1,4]oxazin-4-yl)-5,6-dihydro-4H-benzothiazol-7-one Using Example 2 (40 mg, 0.10 mmol), phenylboronic acid (28 mg, 0.2 mmol), sodium carbonate (22 mg, 0.2 mmol) and tetrakis(triphenylphosphine)palladium(0) (11 mg, 0.009 mmol) in a mixture of THF (3 mL) and water (1 mL) heated to 140° C. under microwave irradiation for 15 min. Purification by prep HPLC gave the title compound as an off-white solid (18 mg, 46%). $\delta_H$ (CDCl$_3$) 1.16 (6H, s), 2.43 (2H, s), 2.78 (2H, s), 4.17-4.27 (2H, m), 4.34-4.43 (2H, m), 7.16-7.24 (2H, m), 7.31-7.39 (1H, m), 7.44 (1H, t, J 7.2 Hz), 7.54-7.62 (2H, m), 8.02 (1H, d, J 9.0 Hz). LCMS (ES+) 391 (M+H)$^+$.

Example 48

5,5-Dimethyl-2-[7-(pyridin-3-yl)-2,3-dihydrobenzo[1,4]oxazin-4-yl]-5,6-dihydro-4H-benzothiazol-7-one Using Example 2 (40 mg, 0.10 mmol), 3-pyridylboronic acid (41 mg, 0.2 mmol), sodium carbonate (22 mg, 0.2 mmol) and tetrakis(triphenylphosphine)palladium(0) (11 mg, 0.009 mmol) in a mixture of THF (3 mL) and water (1 mL) heated to 140° C. under microwave irradiation for 15 min. The crude material was purified by prep HPLC to give the title compound as an off-white solid (17 mg, 44%). $\delta_H$ (CDCl$_3$) 1.09 (6H, s), 2.37 (2H, s), 2.72 (2H, s), 4.08-4.21 (2H, m), 4.26-4.40 (2H, m), 7.09-7.17 (2H, m), 7.24-7.36 (1H, m), 7.79 (1H, d, J 7.9 Hz), 8.04 (1H, d, J 9.0 Hz), 8.53 (1H, br s), 8.77 (1H, br s). LCMS (ES+) 392 (M+H)$^+$.

Example 49

5,5-Dimethyl-2-[7-(1H-pyrazol-4-yl)-2,3-dihydrobenzo[1,4]oxazin-4-yl]-5,6-dihydro-4H-benzothiazol-7-one Using Example 2 (40 mg, 0.10 mmol), 4,4,5,5-tetramethyl-2-(1H-pyrazol-4-yl)-1,3,2-dioxaborolane (41 mg, 0.2 mmol), sodium carbonate (22 mg, 0.2 mmol) and tetrakis(triphenylphosphine)palladium(0) (11 mg, 0.009 mmol) in a mixture of THF (3 mL) and water (1 mL) heated to 140° C. under microwave irradiation for 15 min. Purification by preparative HPLC gave the title compound as an off-white solid (12 mg, 31%). $\delta_H$ (CDCl$_3$) 1.08 (6H, s), 2.36 (2H, s), 2.70 (2H, s), 4.09-4.18 (2H, m), 4.25-4.35 (2H, m), 7.01-7.09 (2H, m), 7.77 (2H, s), 7.86 (1H, d, J 9.2 Hz). LCMS (ES+) 381 (M+H)$^+$.

Example 50

5,5-Dimethyl-2-[7-(1-methyl-1H-pyrazol-4-yl)-2,3-dihydrobenzo[1,4]oxazin-4-yl]-5,6-dihydro-4H-benzothiazol-7-one Using Example 2 (90 mg, 0.5 mmol), 1-methyl-4-(4,4,5,5-tetramethyl-[1,3,2]dioxaborolan-2-yl)-1H-pyrazole (142 mg, 0.7 mmol), sodium carbonate (73 mg, 0.7 mmol) and tetrakis(triphenylphosphine)palladium(0) (26 mg, 0.03 mmol) in a mixture of THF (3 mL) and water (1 mL) heated to 140° C. under microwave irradiation for 15 min. The crude material was purified by prep HPLC to give the title compound as a pale yellow solid (20 mg, 10%). $\delta_H$ (CDCl$_3$) 1.08 (6H, s), 2.35 (2H, s), 2.69 (2H, s), 3.88 (3H, s), 4.11-4.17 (2H, m), 4.25-4.32 (2H, m), 6.95-7.05 (2H, m), 7.53 (1H, br s), 7.66 (1H, br s), 7.83 (1H, d, J 9.0 Hz). LCMS (ES+) 394 (M+H)$^+$.

Example 51

5,5-Dimethyl-2-{6-[(tetrahydrofuran-3-ylmethyl)amino]-2,3-dihydrobenzo[1,4]oxazin-4-yl}-5,6-dihydro-4H-benzothiazol-7-one A mixture of Example 12 (50 mg, 0.15 mmol), tetrahydrofuran-3-carboxaldehyde (30 mg, 0.15 mmol), phenylsilane (0.04 mL, 0.3 mmol) and dibutyltin dichloride (5 mg, 0.015 mmol) in THF (3 mL) was heated to 100° C. under microwave irradiation for 40 min. After cooling to r.t., the mixture was partitioned between EtOAc (50 mL) and water (50 mL). The organics were washed with brine (50 mL), dried (MgSO$_4$) and concentrated in vacuo. The crude material was purified by prep HPLC to give the title compound as a yellow solid (14 mg, 22%). $\delta_H$ (CDCl$_3$) 1.08 (6H, s), 1.56-1.71 (2H, m), 1.98-2.13 (1H; m), 2.35 (2H, s), 2.43-2.57 (1H, m), 2.68 (2H, s), 3.03 (1H, d, J 6.8 Hz), 3.52-3.59 (1H, m), 3.65-3.76 (1H, m), 3.78-3.91 (1H, m), 4.08-4.15 (2H, m), 4.16-4.22 (2H, m), 6.32 (1H, dd, J 8.7, 2.4 Hz), 6.73 (1H, d, J 8.7 Hz), 7.10 (1H, d, J 2.6 Hz). LCMS (ES+) 414 (M+H)$^+$.

Examples 52 to 55

Prepared following the same procedure as Example 51.

Example 52

5,5-Dimethyl-2-{6-[(pyridin-3-ylmethyl)amino]-2,3-dihydrobenzo[1,4]oxazin-4-yl}-5,6-dihydro-4H-benzothiazol-7-one Using Example 12 (50 mg, 0.15 mmol), 3-pyridinecarboxaldehyde (0.02 mL, 0.15 mmol), phenylsilane (0.04 mL, 0.3 mmol) and dibutyltin dichloride (5 mg, 0.015 mmol) in THF (3 mL) heated to 100° C. under microwave irradiation for 40 min. The crude material was purified by prep HPLC to give the title compound as a yellow solid (10 mg, 16%). $\delta_H$ (CDCl$_3$) 1.07 (6H, s), 2.34 (2H, s), 2.65 (2H, s), 4.05-4.12 (2H, m), 4.15-4.22 (2H, m), 4.27 (2H, s), 6.34 (1H, dd, J 8.7, 2.6 Hz), 6.73 (1H, d, J 8.7 Hz), 7.10-7.17 (1H, m), 7.25 (1H, br s), 7.66 (1H, d, J 7.5 Hz), 8.54 (2H, br s). LCMS (ES+) 421 (M+H)$^+$.

Example 53

5,5-Dimethyl-2-{6-[(6-methoxypyridin-3-ylmethyl)amino]-2,3-dihydrobenzo[1,4]oxazin-4-yl}-5,6-dihydro-4H-benzothiazol-7-one Using Example 12 (50 mg, 0.15 mmol), 6-methoxy-3-pyridinecarboxaldehyde (21 mg, 0.15 mmol), phenylsilane (0.04 mL, 0.3 mmol) and dibutyltin dichloride (5 mg, 0.015 mmol) in THF (3 mL) heated to 100° C. under microwave irradiation for 30 min. Purification by prep HPLC gave the title compound as a brown solid (20 mg, 29%). $\delta_H$ (CDCl$_3$) 1.07 (6H, s), 2.34 (2H, s), 2.67 (2H, s), 3.85 (3H, s), 4.05-4.11 (2H, m), 4.15-4.22 (2H, m), 4.17 (2H, s), 6.41 (1H, dd, J 8.9, 2.6 Hz), 6.67 (1H, d, J 8.5 Hz), 6.73 (1H, d, J 8.9 Hz), 7.29 (1H, d, J 2.3 Hz), 7.58 (1H, dd, J 8.5, 2.4 Hz), 8.07 (1H, d, J 1.9 Hz). LCMS (ES+) 451 (M+H)$^+$.

Example 54

5,5-Dimethyl-2-{6-[(3-methyl-3H-imidazol-4-ylmethyl)amino]-2,3-dihydrobenzo[1,4]oxazin-4-yl}-5,6-dihydro-4H-benzothiazol-7-one Using Example 12 (50 mg, 0.15 mmol), 1-methyl-1H-imidazole-5-carboxaldehyde (17 mg, 0.15 mmol), phenylsilane (0.04 mL, 0.3 mmol) and dibutyltin dichloride (5 mg, 0.015 mmol) in THF (3 mL) heated to 100° C. under microwave irradiation for 30 min. The crude material was purified by prep HPLC to give the title compound as a yellow solid (12 mg, 19%). $\delta_H$ (CDCl$_3$) 1.07 (6H, s), 2.33 (2H, s), 2.67 (2H, s), 3.83 (2H, s), 4.09-4.15 (2H, m), 4.16-4.22 (2H, m), 4.27 (2H, s), 6.43 (1H, dd, J 8.9, 2.3 Hz), 6.73 (1H, d, J 8.7 Hz), 7.16 (1H, d, J 2.3 Hz), 7.18-7.22 (1H, m), 8.51 (1H, br s). LCMS (ES+) 424 (M+H)$^+$.

Example 55

4-{[4-(5,5-Dimethyl-7-oxo-4,5,6,7-tetrahydrobenzothiazol-2-yl)-3,4-dihydro-2H-benzo[1,4]oxazin-6-ylamino]methyl}piperidine-1-carboxylic acid tert-butyl ester Using Example 12 (50 mg, 0.15 mmol), 4-formylpiperidine-1-carboxylic acid tert-butyl ester (32 mg, 0.15 mmol), phenylsilane (0.04 mL, 0.3 mmol) and dibutyltin dichloride (5 mg, 0.015 mmol) in THF (3 mL) heated to 100° C. under microwave irradiation for 30 min. The crude material was purified by prep HPLC to give the title compound as a yellow solid (25 mg, 32%). $\delta_H$ (CDCl$_3$) 1.17 (6H, s), 1.20-1.29 (2H, m), 1.47 (9H, s), 1.76-1.96 (3H, m), 2.44 (2H, s), 2.62-2.76 (2H, m), 2.79 (2H, s), 3.07 (2H, d, J 6.0 Hz), 4.06-4.22 (4H, m), 4.26-4.38 (2H, m), 6.76 (1H, br s), 6.84-6.91 (1H, m), 7.42 (1H, br s), 7.71 (1H, br s). LCMS (ES+) 527 (M+H)$^+$.

Example 56

5,5-Dimethyl-2-[6-(1-methyl-1H-pyrazol-4-yl)-2,3-dihydrobenzo[1,4]oxazin-4-yl]-5,6-dihydro-4H-benzothiazol-7-one Example 1 (114 mg, 0.29 mmol), 1-methyl-4-(4,4,5,5-tetramethyl-[1,3,2]dioxaborolan-2-yl)-1H-pyrazole (120 mg, 0.58 mmol), potassium phosphate (190 mg, 0.87 mmol), tetrakis(triphenylphosphine)palladium(0) (10 mg, catalytic) and water (1 mL) in DME (3 mL) were heated to 140° C. under microwave irradiation for 90 min. After cooling to r.t. the reaction mixture was concentrated in vacuo. The crude material was purified by prep HPLC to give the title compound as an off-white solid (17 mg, 15%). $\delta_H$ (CDCl$_3$) 1.16 (6H, s), 2.43 (2H, s), 2.77 (2H, s), 3.95 (3H, s), 4.21-4.28 (2H, m), 4.31-4.39 (2H, m), 6.95 (1H, d, J 8.5 Hz), 7.19 (1H, dd, J 8.5, 2.1 Hz), 7.56 (1H, s), 7.69 (1H, s), 7.98 (1H, d, J 1.9 Hz). LCMS (ES+) 395 (M+H)$^+$.

Example 57

5,5-Dimethyl-2-[6-(pyridin-4-yl)-2,3-dihydrobenzo[1,4]oxazin-4-yl)-5,6-dihydro-4H-benzothiazol-7-one Example 1 (50 mg, 0.13 mmol), pyridine-4-boronic acid (32 mg, 0.25 mmol), sodium carbonate (41 mg, 0.38 mmol), tetrabutylammonium bromide (41 mg, 0.13 mmol), tetrakis(triphenylphosphine)palladium(0) (10 mg, catalytic) and water (2 mL) in DME (3 mL) were heated to 140° C. under microwave irradiation for 20 min. After cooling to r.t. the reaction mixture was concentrated in vacuo. The crude material was purified by prep HPLC to give the title compound as an off-white solid (12 mg, 24%). $\delta_H$ (CDCl$_3$) 1.17 (6H, s), 2.44 (2H, s), 2.79 (2H, s), 4.21-4.28 (2H, m), 4.36-4.45 (2H, m), 7.08 (1H, d, J 8.5 Hz), 7.39 (1H, dd, J 8.5, 2.1 Hz), 7.46-7.50 (2H, m), 8.26 (1H, d, J 2.1 Hz), 8.66 (2H, d, J 6.2 Hz). LCMS (ES+) 392 (M+H)$^+$.

Example 58

2-[6-(3,5-Dimethylisoxazol-4-yl)-2,3-dihydrobenzo[1,4]oxazin-4-yl]-5,5-dimethyl-5,6-dihydro-4H-benzothiazol-7-one Example 1 (50 mg, 0.13 mmol), 3,5-dimethylisoxazole-4-boronic acid (36 mg, 0.25 mmol), sodium carbonate (41 mg, 0.38 mmol), tetrabutylammonium bromide (41 mg, 0.13 mmol), tetrakis(triphenylphosphine)palladium(0) (10 mg, catalytic) and water (2 mL) in DME (3 mL) were heated to 140° C. under microwave irradiation for 20 min. After cooling to r.t. the reaction mixture was concentrated in vacuo. The crude material was purified by prep HPLC to give the title compound as an off-white solid (12 mg, 23%). $\delta_H$ (CDCl$_3$) 1.15 (6H, s), 2.32 (3H, s), 2.43 (2H, s), 2.46 (3H, s), 2.75 (2H, s), 4.12-4.22 (2H, m), 4.35-4.44 (2H, m), 6.94-7.06 (2H, m), 7.99 (1H, d, J 1.9 Hz). LCMS (ES+) 410 (M+H)+.

Example 59

5,5-Dimethyl-2-[6-(pyridin-2-yl)-2,3-dihydrobenzo[1,4]oxazin-4-yl]-5,6-dihydro-4H-benzothiazol-7-one Example 1 (100 mg, 0.25 mmol), 6-chloropyridine-2-boronic acid pinacol ester (122 mg, 0.51 mmol), tetrakis(triphenylphosphine)palladium(0) (13 mg, catalytic), potassium phosphate (160 mg, 0.75 mmol) and water (1 mL) in DME (3 mL) were heated to 140° C. under microwave irradiation for 90 min. After cooling to r.t. the reaction mixture was concentrated in vacuo. The crude material was purified by prep HPLC to give a solid which was dissolved in ethanol (3 mL). Cyclohexene (2 mL) and 10% palladium on carbon (10 mg) were added, and the mixture heated to 120° C. under microwave irradiation for 30 min. After cooling to r.t. the reaction mixture was concentrated in vacuo. The crude material was purified by prep HPLC to give the title compound as an off-white solid (15 mg, 15%). $\delta_H$ (CDCl$_3$) 1.16 (6H, s), 2.43 (2H, s), 2.78 (2H, s), 4.24-4.32 (2H, m), 4.36-4.44 (2H, m), 7.06 (1H, d, J 8.5 Hz), 7.18-7.25 (1H, m), 7.64-7.80 (3H, m), 8.53 (1H, d, J 2.1 Hz), 8.66 (1H, d, J 4.5 Hz). LCMS (ES+) 392 (M+H)+.

Example 60

5,5-Dimethyl-2-[7-(6-methylpyridin-3-yl)-2,3-dihydrobenzo[1,4]oxazin-4-yl]-5,6-dihydro-4H-benzothiazol-7-one Example 2 (90 mg, 0.23 mmol), 2-methylpyridine-5-boronic acid (94 mg, 0.68 mmol), sodium carbonate (74 mg, 0.68 mmol) and tetrakis(triphenylphosphine)-palladium(0) (26 mg, 0.02 mmol) in water (1 mL) and THF (4 mL) were heated to 150° C. under microwave irradiation for 30 min. Additional portions of the boronic acid (94 mg, 0.68 mmol) and tetrakis(triphenylphosphine)palladium(0) (26 mg, 0.02 mmol) were added, and heating continued for a further 50 min. After cooling to r.t. the reaction mixture was partitioned between EtOAc (50 mL) and saturated aqueous sodium bicarbonate (50 mL). The organics were washed with brine (50 mL), dried (MgSO$_4$) and concentrated in vacuo. The crude material was purified by prep HPLC to give the title compound as an off-white solid (17 mg, 18%). $\delta_H$ (CDCl$_3$) 1.09 (6H, s), 2.37 (2H, s), 2.54 (3H, s), 2.71 (2H, s), 4.12-4.18 (2H, m), 4.29-4.35 (2H, m), 7.08-7.18 (3H, m), 7.69 (1H, dd, J 7.9, 2.3 Hz), 8.00 (1H, d, J 9.0 Hz), 8.65 (1H, s). LCMS (ES+) 406 (M+H)+.

Example 61

5,5-Dimethyl-2-[6-(imidazol-1-yl)-2,3-dihydrobenzo[1,4]oxazin-4-yl]-5,6-dihydro-4H-benzothiazol-7-one Example 1 (100 mg, 0.25 mmol), imidazole (26 mg, 0.37 mmol), caesium carbonate (162 mg, 0.5 mmol), copper(I) oxide (2 mg, catalytic) and salicylaldehyde hydrazine (7 mg, 0.05 mmol) in acetonitrile (1 mL) were heated to 80° C. for 6 days. The mixture was cooled to r.t. and concentrated in vacuo. The crude material was purified by prep HPLC to give the title compound as an off-white solid (21 mg, 22%). $\delta_H$ (CDCl$_3$) 1.09 (6H, s), 2.38 (2H, s), 2.72 (2H, s), 4.02-4.08 (2H, m), 4.31-4.37 (2H, m), 6.98-7.03 (2H, m), 7.84 (1H, br s), 8.34 (1H, s). LCMS (ES+) 381 (M+H)+.

Example 62

5,5-Dimethyl-2-[6-(thiazol-5-yl)-2,3-dihydrobenzo[1,4]oxazin-4-yl]-5,6-dihydro-4H-benzothiazol-7-one Example 1 (50 mg, 0.13 mmol) and 5-(tributylstannyl)thiazole (48 mg, 0.13 mmol) in DME (3 mL) were heated to 140° C. under microwave irradiation for 30 min. After cooling to r.t. the reaction mixture was concentrated in vacuo. The crude material was purified by prep HPLC to give the title compound as an off-white solid (11 mg, 22%). $\delta_H$ (CDCl$_3$) 1.16 (6H, s), 2.44 (2H, s), 2.79 (2H, s), 4.15-4.24 (2H, m), 4.35-4.44 (2H, m), 7.01 (1H, d, J 8.5 Hz), 7.24-7.32 (1H, m), 8.01 (1H, s), 8.33 (1H, d, J 2.1 Hz), 8.74 (1H, s). LCMS (ES+) 398 (M+H)+.

Examples 63 and 64

Prepared following the procedure for Example 62.

Example 63

5,5-Dimethyl-2-[6-(thiazol-2-yl)-2,3-dihydrobenzo[1,4]oxazin-4-yl]-5,6-dihydro-4H-benzothiazol-7-one Using Example 1 (50 mg, 0.13 mmol) and 2-(tributylstannyl)thiazole (71 mg, 0.19 mmol) in THF (4 mL) heated to 130° C. under microwave irradiation for 15 min. The crude material was purified by prep HPLC to give the title compound as an off-white solid (9 mg, 17%). $\delta_H$ (CDCl$_3$) 1.16 (6H, s), 2.44 (2H, s), 2.79 (2H, s), 4.19-4.27 (2H, m), 4.35-4.44 (2H, m), 7.03 (1H, d, J 8.7 Hz), 7.30 (1H, d, J 3.2 Hz), 7.69 (1H, dd, J 8.7, 2.3 Hz), 7.83 (1H, d, J 3.4 Hz), 8.64 (1H, d, J 2.1 Hz). LCMS (ES+) 398 (M+H)+.

Example 64

5,5-Dimethyl-2-[6-(2-methoxythiazol-4-yl)-2,3-dihydrobenzo[1,4]oxazin-4-yl]-5,6-dihydro-4H-benzothiazol-7-one Using Example 1 (50 mg, 0.13 mmol) and 2-methoxy-4-(tributylstannyl)thiazole (77 mg, 0.19 mmol) in DME (3 mL) heated to 140° C. under microwave irradiation for 30 min. The crude material was purified by prep HPLC to give the title compound as an off-white solid (17 mg, 31%). $\delta_H$ (CDCl$_3$) 1.09 (6H, s), 2.36 (2H, s), 2.71 (2H, s), 4.17-4.23 (2H, m), 4.26-4.33 (2H, m), 6.70 (1H, s), 6.91 (1H, d, J 8.5 Hz), 7.48 (1H, dd, J 8.7, 2.1 Hz), 8.31 (1H, d, J 2.1 Hz). LCMS (ES+) 428 (M+H)+.

Example 65

7,7-Dimethyl-2-[6-(6-methylpyridin-3-yl)-2,3-dihydrobenzo[1,4]oxazin-4-yl]-5,6,7,8-tetrahydrothiazolo[5,4-c]azepin-4-one Intermediate 5 (150 mg, 0.54 mmol), Intermediate 28 (101 mg, 0.45 mmol), sodium tert-butoxide (130 mg, 1.3 mmol) dicyclohexylphosphinonaphthalene (39 mg) and palladium (II) acetate (13 mg, catalytic) in toluene (15 mL) were heated to 120° C. under microwave irradiation for 3 h. After cooling to r.t. the reaction mixture was concentrated in vacuo. The crude material was purified by prep HPLC to give the title compound as an off-white solid (35 mg, 18%). $\delta_H$ (CDCl$_3$) 1.13 (6H, s), 2.64 (3H, s), 2.88 (2H, s), 3.15 (2H, d, J 5.3 Hz), 4.10-4.20 (2H, m), 4.31-4.41 (2H, m), 7.05 (H, d, J 8.5 Hz), 7.22-7.30 (2H, m), 7.80 (1H, dd, J 7.9, 2.3 Hz), 8.22 (1H, d, J 2.1 Hz), 8.73 (1H, d, J 2.1 Hz). LCMS (ES+) 421 (M+H)$^+$.

Example 66

7,7-Dimethyl-2-[6-(1-methyl-1H-pyrazol-4-yl)-2,3-dihydrobenzo[1,4]oxazin-4-yl]-5,6,7,8-tetrahydrothiazolo[5,4-c]azepin-4-one Intermediate 5 (260 mg, 0.94 mmol), Intermediate 29 (200 mg, 0.93 mmol), sodium tert-butoxide (270 mg, 2.8 mmol) dicyclohexylphosphinonaphthalene (60 mg) and palladium (II) acetate (5 mg, catalytic) in toluene (10 mL) were heated to 120° C. under microwave irradiation for 3 h. After cooling to r.t. the reaction mixture was concentrated in vacuo. The crude material was purified by prep HPLC to give the title compound as an off-white solid (45 mg, 12%). $\delta_H$ (CDCl$_3$) 1.13 (6H, s), 2.88 (2H, s), 3.15 (2H, d, J 5.3 Hz), 3.96 (3H, s), 4.12-4.20 (2H, m), 4.29-4.37 (2H, m), 6.12 (1H, br s), 6.95 (1H, d, J 8.5 Hz), 7.16 (1H, dd, J 8.3, 2.1 Hz), 7.57 (1H, s), 7.71 (1H, s), 8.02 (1H, d, J 2.1 Hz). LCMS (ES+) 410 (M+H)$^+$.

Example 67

2-(6-Bromo-2,3-dihydro-4H-1,4-benzoxazin-4-yl)-7,7-dimethyl-5,6,7,8-tetrahydro-4H-[1,3]thiazolo[5,4-c]azepin-4-one A mixture of Intermediate 30 (1.0 g, 3.6 mmol), Intermediate 32 (1.03 g, 4.4 mmol) and DIPEA (0.96 mL, 5.4 mmol) in THF (15 mL) was heated to 120° C. under microwave irradiation for 20 minutes. Further portions of Intermediate 32 (0.5 g, 2.2 mmol) and DIPEA (0.38 mL, 2.2 mmol) were added and heating continued for a further 20 minutes. The mixture was cooled to r.t., concentrated in vacuo and partitioned between water and DCM. The aqueous fraction was extracted with DCM. The combined organic fractions were washed with water and brine, dried (MgSO$_4$) and concentrated in vacuo. The residue was triturated with ether to give the title compound (1.0 g, 67%) as a brown solid. $\delta_H$ (CDCl$_3$) 1.12 (6H, s), 1.57 (2H, s), 3.10-3.17 (2H, m), 4.02-4.08 (2H, m), 4.27-4.33 (2H, m), 5.92 (1H, br.s), 6.81 (1H, d, J 8.7 Hz), 7.12 (1H, dd, J 8.7, 2.3 Hz), 8.22 (1H, d, J 2.3 Hz). LCMS (ES+) 410/411 (M+H)$^+$.

Example 68

2-(7-Bromo-2,3-dihydro-4H-1,4-benzoxazin-4-yl)-7,7-dimethyl-5,6,7,8-tetrahydro-4H-[1,3]thiazolo[5,4-c]azepin-4-one Prepared following the procedure for Example 67 using Intermediate 31 (820 mg, 3.0 mmol), Intermediate 32 (1.19 g, 5.1 mmol) and DIPEA (774 mg, 6.0 mmol) in THF (5 mL) heated to 120° C. under microwave irradiation for 20 minutes. The mixture was cooled to r.t., concentrated in vacuo and purified by column chromatography (SiO$_2$, 20% EtOAc in heptane increasing to 100% EtOAc followed by SiO$_2$, DCM increasing to 10% MeOH in DCM) to give the title compound (186 mg, 15%) as an orange solid. $\delta_H$ (CDCl$_3$) 1.05 (6H, s), 2.85 (2H, s), 7.86 (H, d, J 8.7 Hz), 3.12 (2H, d, J 6.6 Hz), 4.04-4.11 (2H, m), 4.27-4.33 (2H, m), 6.67 (H, br.s), 7.02-7.07 (H, m), 7.10 (H, d, J 2.3 Hz). LCMS (ES+) 410/411 (M+H)$^+$.

Example 69

2-(6-Amino-2,3-dihydro-4H-1,4-benzoxazin-4-yl)-7,7-dimethyl-5,6,7,8-tetrahydro-4H-[1,3]thiazolo[5,4-c]azepin-4-one A mixture of Example 67 (0.48 g, 0.98 mmol), benzophenone imine (0.356 g, 1.96 mmol), rac-2,2'-bis(diphenylphosphino)-1,1'-binaphthyl (40 mg, 0.06 mmol), sodium tert-butoxide (0.192 g, 2.0 mmol) and tris(dibenzylidineacetone)dipalladium(0) (29 mg, catalytic) in THF (10 mL) was heated to 120° C. for 2 h. The reaction mixture was cooled to r.t., concentrated in vacuo, and the residue dissolved in methanol (2 mL). 2N Hydrochloric acid (10 mL) was added and the mixture stirred overnight. It was basified with aqueous sodium carbonate and extracted with DCM (3×25 mL). The combined organic fractions were dried (MgSO$_4$) and concentrated in vacuo. The residue was triturated with Et$_2$O to give the title compound (0.30 g, 89%) as a beige solid. $\delta_H$ (CDCl$_3$) 1.11 (6H, s), 2.85 (2H, s), 3.12 (2H, d, J 5.3 Hz), 3.52 (2H, br.s), 4.07-4.13 (2H, m), 4.19-4.26 (2H, m), 5.93 (1H, br.s), 6.40 (1H, dd, J 8.5, 2.6 Hz), 6.75 (1H, d, J 8.7 Hz), 7.29 (1H, d, J 2.6 Hz). LCMS (ES+) 345 (M+H)$^+$.

Example 70

7,7-Dimethyl-2-(6-pyridazin-3-yl-2,3-dihydro-4H-1,4-benzoxazin-4-yl)-5,6,7,8-tetrahydro-4H-[1,3]thiazolo[5,4-c]azepin-4-one Prepared following the procedure for Example 62 using Example 67 (0.05 g, 0.12 mmol) and 3-(tributylstannyl)pyridazine (0.089 mg, 0.24 mmol) heated to 150° C. under microwave irradiation for 20 minutes. Purification by prep HPLC gave the title compound (19.3 mg, 40%) as an off-white solid. $\delta_H$ (CD$_3$OD) 2.05 (6H, s), 2.90 (2H, s), 3.13 (2H, s), 4.09-4.18 (2H, m), 4.37-4.44 (2H, m), 7.15 (1H, d, J 8.5 Hz), 7.60 (1H, dd, J 8.5, 2.1 Hz), 7.96 (1H, dd, J 5.5, 2.6 Hz), 8.65 (1H, d, J 2.3 Hz), 9.15-9.20 (1H, m), 9.49-9.53 (1H, m). LCMS (ES+) 408 (M+H)$^+$.

Example 71

2-{6-[1-(2-Hydroxy-2-methyl-propyl)-1H-pyrazol-4-yl]-2,3-dihydro-benzo[1,4]oxazin-4-yl}-7,7-dimethyl-5,6,7,8-tetrahydro-thiazolo[5,4-c]azepin-4-one A mixture of Example 67 (0.30 g, 0.73 mmol), Intermediate 33 (0.19 g, 0.73 mmol), tetrakis(triphenylphosphine)palladium(0) (174 mg, 0.15 mmol) and potassium acetate (72 mg, 0.739 mmol) in DME (7 mL) and water (3 mL) was heated to 140° C. under microwave irradiation for 15 minutes. After cooling to r.t. it was concentrated in vacuo, and purified by prep HPLC to give the title compound (22 mg, 6%) as a brown glass. $\delta_H$ (CDCl$_3$) 1.12 (6H, s), 1.21 (6H, s), 2.87 (2H, s), 3.14 (2H, d, J 5.3 Hz), 4.10-4.19 (3H, m), 4.28-4.37 (2H, m), 6.57 (1H, br.s), 6.95 (1H, d, J 8.5 Hz), 7.16 (1H, dd, J 8.5, 2.1 Hz), 7.61 (1H, s), 7.76 (1H, s), 8.01 (1H, d, J 1.9 Hz), 8.03 (1H, br.s). LCMS (ES+) 468 (M+H)$^+$.

Example 72

2-{6-[1-(2-Hydroxy-3-methoxypropyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one A mixture of Example 67 (0.10 g, 0.24 mmol), Intermediate 35 (0.207 g, 0.73 mmol), tetrakis(triphenylphosphine)palladium(0) (15 mg, 0.01 mmol), potassium phosphate (104 mg, 0.49 mmol) and tetra-n-butylammonium bromide (79 mg, 0.24 mmol) in THF (3 mL) and water (1 mL) was heated to 120° C. under microwave irradiation for 20 minutes. After cooling to r.t. the mixture was filtered through celite. The filtrate was partitioned between water (5 mL) and EtOAc (10 mL). The aqueous fraction was extracted with EtOAc (3×10 mL). The combined organic fractions were concentrated in vacuo and purified by prep HPLC to give the title compound (31 mg, 25%) as a pale brown solid. $\delta_H$(CDCl$_3$) 1.12 (6H, s), 2.86 (2H, s), 3.13 (2H, d, J 5.3 Hz), 3.30-3.40 (2H, m), 3.39 (3H, s), 3.52 (1H, br.s), 4.09-4.35 (7H, m), 6.94 (1H, d, J 8.5 Hz), 7.15 (1H, dd, J 8:5, 2.1 Hz), 7.64 (1H, s), 7.73 (1H, s), 8.03 (1H, d, J 2.3 Hz). LCMS (ES+) 484 (M+H)$^+$.

Examples 73-76 and Intermediates 47 and 48 were prepared following the procedure for Example 72.

Example 73

5,5-Dimethyl-2-[6-(6-methyl-1-oxidopyridin-3-yl)-2,3-dihydro-4H-1,4-benzoxazin-4-yl]-5,6-dihydro-1,3-benzothiazol-7(4H)-one Using Intermediate 46 (90 mg, 0.204 mmol), 5-bromo-2-methylpyridine-N-oxide (39 mg, 0.206 mmol), tetra-n-butylammonium bromide (51 mg, 0.158 mmol), tetrakis(triphenylphosphine)palladium(0) (9 mg, 0.008 mmol), potassium phosphate (67 mg, 0.316 mmol) in THF (3 mL) and water (1 mL) and heated to 80° C. under microwave irradiation for 10 minutes, then to 120° C. under microwave irradiation for a further 15 minutes. Purification by prep HPLC gave the title compound (27 mg, 40%) as an off-white solid $\delta_H$ (CDCl$_3$) 1.16 (6H, s), 2.44 (2H, s), 2.57 (3H, s), 2.79 (2H, s), 4.17-4.23 (2H, m), 4.38-4.42 (2H, m), 7.04-7.09 (1H, m), 7.22-7.39 (3H, m), 8.23 (1H, d, J 2.1 Hz), 8.51 (1H, d, J 1.3 Hz). LCMS (ES+) 422 (M+H)$^+$.

Example 74

2-(6-{6-[(2-Hydroxyethyl)amino]-2-methylpyrimidin-4-yl}-2,3-dihydro-4H-1,4-benzoxazin-4-yl)-5,5-dimethyl-5,6-dihydro-1,3-benzothiazol-7(4H)-one Using Intermediate 46 (90 mg, 0.204 mmol), 2-(6-chloro-2-methylpyrimidin-4-ylamino)-ethanol (57 mg, 0.305 mmol), tetra-n-butylammonium bromide (66 mg, 0.205 mmol), tetrakis(triphenylphosphine)palladium(0) (12 mg, 0.104 mmol), potassium phosphate (82 mg, 0.387 mmol) in THF (3 mL) and water (1 mL) and heated to 120° C. under microwave irradiation for 20 minutes. Purification by prep HPLC gave the title compound (29 mg, 31%) as an off-white solid. $\delta_H$(CDCl$_3$) 1.16 (6H, s), 2.43 (2H, s), 2.56 (3H, s), 2.77 (2H, s), 3.56-3.64 (2H, m), 3.82-3.90 (2H, m), 4.24-4.30 (2H, m), 4.34-4.41 (2H, m), 5.55 (1H, br.s), 6.52 (1H, s), 7.02 (1H, d, J 8.7 Hz), 7.73 (1H, dd, J 8.7, 2.1 Hz), 8.43 (1H, d, J 1.7 Hz). LCMS (ES+) 466 (M+H)$^+$.

Example 75

7,7-Dimethyl-2-[6-(6-methyl-1-oxidopyridin-3-yl)-2,3-dihydro-4H-1,4-benzoxazin-4-yl]-5,6,7,8-tetrahydro-4H-[1,3]thiazolo[5,4-c]azepin-4-one Using Intermediate 45 (90 mg, 0.20 mmol), 5-bromo-2-methylpyridine-N-oxide (45 mg, 0.24 mmol), tetra-n-butylammonium bromide (64 mg, 0.20 mmol), tetrakis(triphenylphosphine)palladium(0) (11 mg, 0.009 mmol), potassium phosphate (63 mg, 0.3 mmol) heated to 100° C. under microwave irradiation for 10 minutes. The crude material was purified by prep HPLC to give the title compound (46 mg, 53%) as an off-white solid. $\delta_H$(CDCl$_3$) 1.12 (6H, s), 2.56 (3H, s), 2.87 (2H, s), 3.13 (2H, d, J 5.1 Hz), 4.05-4.17 (2H, m), 4.31-4.42 (2H, m), 5.96 (1H, br.s), 7.04 (1H, d, J 8.5 Hz), 7.20 (1H, dd, J 8.3, 1.9 Hz), 7.24-7.40 (2H, m), 8.21 (1H, d, J 2.1 Hz), 8.50 (1H, s). LCMS (ES+) 437 (M+H)$^+$.

Example 76

5,5-Dimethyl-2-[6-(6-methylpyridin-3-yl)-2,3-dihydro-4H-1,4-benzoxazin-4-yl]-5,6-dihydro-1,3-benzothiazol-7(4H)-one Using Intermediate 46 (86 mg, 0.195 mmol), 5-bromo-2-methylpyridine (50 mg, 0.293 mmol), tetra-n-butylammonium bromide (51 mg, 0.158 mmol), tetrakis(triphenylphosphine)palladium(0) (catalytic amount) and potassium phosphate (166 mg, 0.781 mmol) in THF (4.0 mL) and water (0.8 mL) and heated to 110° C. under microwave irradiation for 1 h. Purification by prep HPLC gave the title compound (36 mg, 46%) as a brown solid. $\delta_H$(CDCl$_3$) 1.16 (6H, s), 2.43 (2H, s), 2.61 (3H, s), 2.78 (2H, s), 4.20-4.25 (2H, m), 4.36-4.42 (2H, m), 7.03-7.09 (1H, m), 7.22-7.33 (2H, m), 7.76 (1H, dd, J 8.1, 2.4 Hz), 8.20 (1H, d, J 2.1 Hz), 8.72 (1H, d, J 2.1 Hz). LCMS (ES+) 406 (M+H)$^+$.

Example 77

2-{6-[1-(2,3-Dihydroxypropyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one A mixture of Intermediate 47 (0.41 g, 0.94 mmol), osmium tetroxide (11 mg, 0.05 mmol), 4-methylmorpholine N-oxide (132 mg, 1.13 mmol), acetone (10 mg, 0.2 mmol), tert-butanol (0.035 mL, 0.4 mmol) and water (1 mL) was stirred overnight at r.t. Purification by prep HPLC gave the title compound (164 mg, 37%) as a beige foam. $\delta_H$ (CDCl$_3$) 1.12 (6H, s), 2.86 (2H, s), 3.13 (2H, d, J 5.1 Hz), 3.63-3.69 (2H, m), 4.10-4.19 (3H, m), 4.27-4.35 (4H, m), 5.94 (1H, br.s), 6.94 (1H, d, J 8.5 Hz), 7.15 (1H, dd, J 8.7, 2.3 Hz), 7.65 (1H, s), 7.74 (1H, s), 8.00 (1H, d, J 2.1 Hz). LCMS (ES+) 470 (M+H)$^+$.

Example 78

2-{6-[1-(2,3-Dihydroxypropyl)-1H-pyrazol-4-yl]-2,3-dihydro-4H-1,4-benzoxazin-4-yl}-5,5-dimethyl-5,6-dihydro-1,3-benzothiazol-7(4H)-one Prepared following the procedure for Example 77 using Intermediate 48 (0.40 g, 0.95 mmol), osmium tetroxide (12 mg, 0.05 mmol), 4-methylmorpholine N-oxide (134 mg, 1.14 mmol), acetone (10 mg, 0.2 mmol), tert-butanol (0.035 mL, 0.4 mmol) and water (1 mL). Purification by prep HPLC gave the title compound (116 mg, 22%) as a beige foam. $\delta_H$ (CDCl$_3$) 1.16 (6H, s), 2.44 (2H, s), 2.77 (2H, s), 3.64-3.70 (2H, m), 4.09-4.39 (7H, m), 6.97 (1H, d, J 8.5 Hz), 7.19 (1H, dd, J 8.5, 2.1 Hz), 7.65 (1H, s), 7.75 (1H, s), 8.00 (1H, d, J 2.1 Hz). LCMS (ES+) 455 (M+H)$^+$.

Examples 79 to 84 were prepared following the procedure for Example 56.

Example 79

2-[6-(1,2-Dimethyl-1H-imidazol-5-yl)-2,3-dihydro-4H-1,4-benzoxazin-4-yl]-7,7-dimethyl-5,6,7,8-tetrahydro-4H-[1,3]thiazolo[5,4-c]azepin-4-one Using Intermediate 45 (0.074 g, 0.16 mmol) and 5-bromo-1,2-dimethyl-1H-imidazole (0.057 g, 0.32 mmol), tetrakis(triphenylphosphine)palladium(0) (10 mg, 0.009 mmol) and potassium phosphate (102 mg, 0.48 mmol) in DME (4 mL) and water (1 mL) heated to 120° C. under microwave irradiation for 20 minutes. The crude material was purified by prep HPLC to give the title compound (4.5 mg, 6%) as an off-white solid. $\delta_H$ (CDCl$_3$) 1.11 (6H, s), 2.45 (3H, s), 2.84 (2H, s), 3.12 (2H, d, J 5.3 Hz), 3.58 (3H, s), 4.07-4.16 (2H, m), 4.31-4.39 (2H, m), 5.93 (1H, br.s), 6.90-7.07 (3H, m), 7.98 (1H, d, J 1.9 Hz). LCMS (ES+) 424 (M+H)$^+$.

Example 80

2-{6-[1-(2-Hydroxyethyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one Using Intermediate 45 (0.10 g, 0.22 mmol), 2-(4-bromopyrazol-1-yl)-ethanol (42 mg, 0.22 mmol), tetrakis(triphenylphosphine)palladium(0) (52 mg, 0.04 mmol) and potassium phosphate (93 mg, 0.43 mmol) in DME (3 mL) and water (1 mL) heated to 140° C. under microwave irradiation for 20 mins. The crude material was purified by prep HPLC to give the title compound (32 mg, 33%) as an off-white solid. $\delta_H$ (CDCl$_3$) 1.11 (6H, s), 2.85 (2H, s), 3.12 (2H, d, J 5.1 Hz), 4.00-4.07 (2H, m), 4.10-4.17 (2H, m), 4.23-4.36 (4H, m), 6.93 (1H, d, J 8.5 Hz), 7.14 (1H, dd, J 8.3, 1.9 Hz), 7.64 (1H, s), 7.72 (1H, s), 7.99 (1H, d, J 1.9 Hz). LCMS (ES+) 440 (M+H)$^+$.

Example 81

2-{6-[5-(2-Hydroxyethyl)pyridin-2-yl]-2,3-dihydro-4H-1,4-benzoxazin-4-yl}-5,5-dimethyl-5,6-dihydro-1,3-benzothiazol-7(4H-one Using Intermediate 46 (100 mg, 0.227 mmol), 2-(6-chloropyridin-3-yl)-ethanol (155 mg, 0.978 mmol), tetrakis(triphenylphosphine)palladium(0) (39 mg, 0.033 mmol), potassium phosphate (120 mg, 0.566 mmol) in THF (3 mL) and water (1 mL) and heating at 125° C. for 2 h. Purification by prep HPLC gave the title compound (5 mg, 5%) as an off-white solid. $\delta_H$ (CDCl$_3$) 1.16 (6H, s), 2.43 (2H, s), 2.77 (2H, s), 2.91 (2H, t, J 6.6 Hz), 3.92 (2H, t, J 6.4 Hz), 4.25-4.31 (2H, m), 4.35-4.41 (2H, m), 7.05 (1H, d, J 8.5 Hz), 7.61-7.64 (2H, m), 7.73 (1H, dd, J 8.7, 2.1 Hz), 8.51 (1H, d, J 1.9 Hz), 8.53 (1H, s). LCMS (ES+) 436 (M+H)$^+$.

Example 82

2-{6-[1-(2-Hydroxy-3-methoxypropyl)-1H-pyrazol-4-yl]-2,3-dihydro-4H-1,4-benzoxazin-4-yl}-5,5-dimethyl-5,6-dihydro-1,3-benzothiazol-7(4H)-one Using Intermediate 46 (90 mg, 0.204 mmol), Intermediate 37 (53 mg, 0.225 mmol), tetrakis(triphenylphosphine)palladium(0) (12 mg, 0.010 mmol), potassium phosphate (87 mg, 0.410 mmol) in THF (1.5 mL) and water (0.5 mL) and heated to 100° C. under microwave irradiation for 2 h. Purification by prep HPLC gave the title compound (39 mg, 41%) as a yellow oil. $\delta_H$ (CDCl$_3$) 1.16 (6H, s), 2.43 (2H, s), 2.77 (2H, s), 3.32-3.44 (5H, m), 3.53 (1H, d, J 4.3 Hz), 4.17-4.38 (7H, m), 6.96 (1H, d, J 8.5 Hz), 7.19 (1H, dd, J 8.5, 2.1 Hz), 7.64 (1H, s), 7.73 (1H, s), 8.01 (1H, d, J 1.9 Hz). LCMS (ES+) 469 (M+H)$^+$.

Example 83

2-(6-Imidazo[1,2-a]pyrazin-3-yl-2,3-dihydro-4H-1,4-benzoxazin-4-yl)-5,5-dimethyl-5,6-dihydro-1,3-benzothiazol-7(4H-one Using Intermediate 46 (120 mg, 0.272 mmol), 3-bromoimidazo[1,2-a]pyrazine (81 mg, 0.409 mmol), potassium phosphate (231 mg, 1.09 mmol) and tetrakis(triphenylphosphine)palladium(0) (10 mg, 0.009 mmol) in THF (3.6 mL) and water (1.4 mL) heated to 100° C. under microwave irradiation for 30 minutes. Purification by prep HPLC followed by dissolution in DCM (15 mL), washing with aqueous potassium carbonate solution (0.7 M) and concentration of the organic fraction in vacuo gave the title compound (11 mg, 10%) as a pale yellow solid. $\delta_H$ (CD$_3$OD) 1.16 (6H, s), 2.47 (2H, s), 2.85 (2H, s), 4.17-4.22 (2H, m), 4.44-4.49 (2H, m), 7.20 (1H, d, J 8.9 Hz) 7.43 (1H, d, J 8.1 Hz), 7.95-8.02 (2H, m), 8.61 (1H, d, J 0.9 Hz), 8.69-8.70 (1H, m), 9.08 (1H, dd, J 1.9, 0.9 Hz). LCMS (ES+) 432.13 (M+H)$^+$.

Example 84

2-(6-Imidazo[1,2-a]pyrimidin-3-yl-2,3-dihydro-4H-1,4-benzoxazin-4-yl)-5,5-dimethyl-5,6-dihydro-1,3-benzothiazol-7(4H)-one Using Intermediate 46 (150 mg, 0.34 mmol), 3-bromoimidazo[1,2-a]pyrimidine (135 mg, 0.68 mmol), potassium phosphate (289 mg, 1.36 mmol) and tetrakis(triphenylphosphine)palladium(0) (10 mg, catalytic) in THF (3.7 mL) and water (1.3 mL) heated to 100° C. under microwave irradiation for 30 minutes. Purification by prep HPLC gave the title compound (18 mg, 13%) as a white solid. $\delta_H$ (CDCl$_3$) 1.16 (6H, s), 2.44 (2H, s), 2.77 (2H, s), 4.12-4.17 (2H, m), 4.41-4.46 (2H, m), 6.94 (1H, dd, J 6.8, 4.0 Hz), 7.10-7.14 (1H, m), 7.24-7.27 (1H, m), 7.90 (1H, s), 8.39 (1H, d, J 2.1 Hz), 8.60 (1H, dd, J 4.1, 2.1 Hz), 8.81 (1H, dd, J 7.0, 2.1 Hz). LCMS (ES+) 432.4 (M+H)$^+$.

Example 85

2-{6-[1-(2-Hydroxyethyl)-1H-pyrazol-4-yl]-2,3-dihydro-4H-1,4-benzoxazin-4-yl}-5,5-dimethyl-5,6-dihydro-1,3-benzothiazol-7(4H)-one A mixture of Example 1 (0.275 g, 0.7 mmol), Intermediate 34 (0.25 g, 1.049 mmol), potassium acetate (82 mg, 0.84 mmol) and bis(tris-tert-butylphosphino)palladium(0) (32 mg, 0.063 mmol) in DMF (2 mL) was heated to 140° C. under microwave irradiation for 1 h. After cooling to r.t. activated charcoal (25 mg) was added and the resulting suspension stirred for 2 h. It was filtered through celite, washed with DMF (3 mL) and concentrated in vacuo. The residue was purified by prep HPLC then dissolved in DCM (15 mL), washed with aqueous potassium carbonate solution (0.7 M) and the organic fraction was concentrated in vacuo to give the title compound (113 mg, 38%) as a pale yellow solid. $\delta_H$ (CDCl$_3$) 1.16 (6H, s), 2.43 (2H, s), 2.77 (2H, s), 3.06 (1H, t, J 6.0 Hz), 4.02-4.08 (2H, m), 4.22-4.36 (6H, m), 6.96 (1H, d, J 8.3 Hz), 7.19 (1H, dd, J 8.5, 2.1 Hz), 7.64 (1H, s), 7.74 (1H, d, J 0.6 Hz), 7.99 (1H, d, J 1.9 Hz). LCMS (ES+) 425.17 (M+H)$^+$.

Example 86

7,7-Dimethyl-2-{6-[(6-methylpyridazin-3-yl)amino]-2,3-dihydro-4H-1,4-benzoxazin-4-yl}-5,6,7,8-tetrahydro-4H-[1,3]thiazolo[5,4-c]azepin-4-one acetate salt A mixture of Example 69 (100 mg, 0.29 mmol), chloromethylpyridazine (20 mg, 0.29 mmol), sodium tert-butoxide (80 mg, 0.8 mmol) and dichloro(1,1'-bis(di-tert-butylphosphino)ferrocene)palladium (10 mg, catalytic) in toluene (5 mL) was heated to 120° C. under microwave irradiation for 2 h. It was cooled to r.t., concentrated in vacuo and purified by prep HPLC to give the title compound (14 mg, 9%) as an off-white solid. $\delta_H$ (CD$_3$OD/CDCl$_3$) 1.11 (6H, s), 2.02 (3H, s), 2.54 (3H, s), 2.85 (2H, s), 3.12 (2H, s), 4.09-4.17 (2H, m), 4.29-4.35 (2H, m), 6.94 (1H, d, J 8.9 Hz), 7.10-7.30 (3H, m), 7.99 (1H, s). LCMS (ES+) 437 (M+H)$^+$.
Examples 87 and 88 were prepared in the same manner as Example 86.

Example 87

2-[6-({6-[(E)-2-Methoxyvinyl]pyridin-2-yl}amino)-2,3-dihydro-4H-1,4-benzoxazin-4-yl]-7,7-dimethyl-5,6,7,8-tetrahydro-4H-[1,3]thiazolo[5,4-c]azepin-4-one Using Example 69 (0.15 g, 0.44 mmol), Intermediate 39 (93 mg, 0.44 mmol) sodium tert-butoxide (84 mg, 0.87 mmol) and dichloro(1,1'-bis(di-tert-butylphosphino)ferrocene)palladium (20 mg, 0.037 mmol in toluene (5 mL) heated to 120° C. under microwave irradiation for 1 h. The crude material was purified by prep HPLC to give the title compound (16 mg, 7%) as a beige solid. $\delta_H$ (CDCl$_3$) 1.11 (6H, s), 2.85 (2H, s), 3.12 (2H, d, 5.3 Hz), 3.70 (3H, s), 4.04-4.12 (2H, m), 4.26-4.35 (2H, m), 5.75 (1H, d, J 12.8 Hz), 5.81 (1H, s), 6.37 (1H, s), 6.50 (1H, d, J 7.5 Hz), 6.62 (1H, d, J 7.9 Hz), 6.87-6.93 (1H, m), 7.00-7.07 (1H, m), 7.34-7.42 (1H, m), 7.56 (1H, d, J 12.6 Hz), 8.02 (1H, d, J 2.4 Hz). LCMS (ES+) 478 (M+H)$^+$.

Example 88

7,7-Dimethyl-2-(7-pyrrolidin-1-yl-2,3-dihydro-4H-1,4-benzoxazin-4-yl)-5,6,7,8-tetrahydro-4H-[1,3]thiazolo[5,4-c]azepin-4-one Using Example 68 (50 mg, 0.12 mmol), pyrrolidine (25 mg, 0.24 mmol) sodium tert-butoxide (28 mg, 0.29 mmol) and dichloro(1,1'-bis(di-tert-butylphosphino)ferrocene)palladium (9 mg, 0.018 mmol) in toluene (2 mL) heated to 130° C. under microwave irradiation for 1 h. The crude material was purified by prep HPLC to give the title compound (4 mg, 8%) as a beige solid. $\delta_H$ (CDCl$_3$) 1.10 (6H, s), 1.92-2.07 (4H, m), 2.82 (2H, s), 3.10 (2H, d, J 5.3 Hz), 3.19-3.32 (4H, m), 4.07-4.14 (2H, m), 4.23-4.29 (2H, m), 5.85 (1H, br.s), 6.11 (1H, d, J 2.6 Hz), 6.17 (1H, dd, J 9.0, 2.8 Hz), 7.58 (1H, d, J 8.9 Hz). LCMS (ES+) 399 (M+H)$^+$.

Example 89

5,5-Dimethyl-2-{6-[(6-methylpyridazin-3-yl)amino]-2,3-dihydro-4H-1,4-benzoxazin-4-yl}-5,6-dihydro-1,3-benzothiazol-7(4H)-one A mixture of Example 12 (44 mg, 0.134 mmol), 3-chloro-6-methylpyridazine (15 mg, 0.116 mmol) and DIPEA (0.5 mL, 67.0 mmol) was heated to 180° C. under microwave irradiation for 2 h. A further portion of 3-chloro-6-methylpyridazine (15 mg, 0.116 mmol) was added and heating continued for a further 20 h. The solvent was removed in vacuo and the residue purified by prep HPLC to give the title compound (13 mg, 23%) as a yellow solid. $\delta_H$ (CDCl$_3$) 1.15 (6H, s), 2.42 (2H, s), 2.58 (3H, s), 2.76 (2H, s), 4.13-4.18 (2H, m), 4.32-4.38 (2H, m), 6.93-7.20 (5H, m), 8.03 (1H, d, J 2.4 Hz). LCMS (ES+) 422 (M+H)$^+$.

Example 90

5,5-Dimethyl-2-{6-[(5-methyl-1,3,4-thiadiazol-2-yl)oxy]-2,3-dihydro-4H-1,4-benzoxazin-4-yl}-5,6-dihydro-1,3-benzothiazol-7(4H)-one A mixture of Example 6 (75 mg, 0.23 mmol), 2-bromo-5-methyl-1,3,4-thiadiazole (42 mg, 0.23 mmol) and potassium carbonate (64 mg, 0.46 mmol) in DMF (7 mL) was heated to 150° C. for 10 h. The solvent was removed in vacuo and the residue was purified by prep HPLC to give the title compound (12 mg, 12%) as an off-white solid. $\delta_H$ (CDCl$_3$) 1.14 (6H, s), 2.43 (2H, s), 2.67 (3H, s), 2.77 (2H, s), 4.09-4.15 (2H, m), 4.33-4.40 (2H, m), 6.96-7.06 (2H, m), 8.22-8.24 (1H, m). LCMS (ES+) 429 (M+H)$^+$.

Example 91

5,5-Dimethyl-2-{6-[(6-methylpyridazin-3-yl)oxy]-2,3-dihydro-4H-1,4-benzoxazin-4-yl}-5,6-dihydro-1,3-benzothiazol-7(4H)-one Prepared following the procedure for Example 90 using Example 6 (44 mg, 0.133 mmol), 3-chloro-6-methylpyridazine (20 mg, 0.156 mmol) and potassium carbonate (37 mg, 0.27 mmol) in DMF (4 mL) heated to 150° C. for 12 h. Purification by prep HPLC gave the title compound (16 mg, 29%) as an off-white solid. $\delta_H$ (CDCl$_3$) 1.13 (6H, s), 2.41 (2H, s), 2.64 (3H, s), 2.74 (2H, s), 4.16-4.20 (2H, m), 4.33-4.38 (2H, m), 6.90-7.01 (2H, m), 7.07-7.12 (1H, m), 7.32-7.37 (1H, m), 7.96 (1H, d, J 2.4 Hz). LCMS (ES+) 423 (M+H)$^+$.

Example 92

5,5-Dimethyl-2-{6-[(6-piperazin-1-ylpyridazin-3-yl)oxy]-2,3-dihydro-4H-1,4-benzoxazin-4-yl}-5,6-dihydro-1,3-benzothiazol-7(4H)-one A mixture of 3,6-dichloropyridazine (0.60 g, 3.24 mmol), 1-BOC-piperazine (0.48 g, 3.24 mmol) and DIPEA (0.60 mL, 3.24 mmol) in THF (20 mL) was heated to 140° C. under microwave irradiation for 3 h. After cooling to r.t. it was concentrated in vacuo and purified by column chromatography (SiO$_2$, 0-50% EtOAc in heptane) to give a white solid. A mixture of this material (crude pyridazinyl piperazine, 45 mg, 0.15 mmol), Example 6 (50 mg, 0.15 mmol) and cesium carbonate (98 mg, 0.3 mmol) in DMF (4 mL) was heated to 120° C. under microwave irradiation for 2 h. After cooling to r.t. the mixture was concentrated in vacuo and purified by prep HPLC to give an off-white solid (26 mg, 30%). $\delta_H$ (CDCl$_3$) 1.13 (6H, s), 1.48 (9H, s), 2.41 (2H, s), 2.74 (2H, s), 3.14 (8H, br.s), 4.15-4.24 (2H, m), 4.30-4.38 (2H, m), 6.89-7.00 (2H, m), 7.26 (2H, s), 7.89 (1H, d, J 2.4 Hz). LCMS (ES+) 593 (M+H)$^+$.

A solution of the resulting off-white solid (26 mg, 0.04 mmol) in trifluoroacetic acid (5 mL) was stirred at r.t. for 3 h. The mixture was concentrated in vacuo and partitioned between saturated aqueous sodium bicarbonate and DCM. The organic fraction was dried (MgSO$_4$), concentrated in vacuo and purified by prep HPLC. The resulting material was dissolved in DCM, washed with saturated aqueous sodium bicarbonate solution, dried (MgSO$_4$) and concentrated in vacuo to give the title compound (14 mg, 66%) as an off-white solid. $\delta_H$ (CDCl$_3$) 1.13 (6H, s), 2.41 (2H, s), 2.74 (2H, s), 3.10-3.19 (4H, m), 3.63-3.73 (4H, m), 4.15-4.23 (2H, m), 4.30-4.37 (2H, m), 6.89-7.00 (2H, m), 7.26 (2H, s), 7.86 (1H, d, J 2.4 Hz). LCMS (ES+) 493 (M+H)$^+$.

Example 93

7,7-Dimethyl-2-[7-methyl-6-(1-methyl-1H-pyrazol-4-yl)-2,3-dihydro-4H-1,4-benzoxazin-4-yl]-5,6,7,8-tetrahydro-4H[1,3]thiazolo[5,4-e]azepin-4-one A mixture of Intermediate 5 (52 mg, 0.19 mmol), Intermediate 42 (87 mg, 0.38 mmol), sodium tert-butoxide (46 mg, 0.475 mmol) and dichloro(1,1,1-bis(di-tert-butylphosphino)ferrocene)palladium (12 mg, 0.022 mmol) in toluene (1 mL) was heated to 140° C. under microwave irradiation for 1 h. Purification by prep HPLC gave the title compound (74 mg, 92%) as a brown solid. $\delta_H$ (CDCl$_3$) 1.10 (6H, s), 2.32 (3H, s), 2.83 (2H, s), 3.11 (2H, d, J 5.1 Hz), 3.96 (3H, s), 4.10-4.15 (2H, m), 4.26-4.31 (2H, m), 5.86-5.92 (1H, m), 6.82 (1H, s), 7.43 (1H, s), 7.57 (1H, s), 7.79 (1H, s). LCMS (ES+) 424.18 (M+H)$^+$.

Example 94

2-[6-(6-Methoxypyridin-3-yl)-7-methyl-2,3-dihydro-4H-1,4-benzoxazin-4-yl]-7,7-dimethyl-5,6,7,8-tetrahydro-4H-[1,3]thiazolo[5,4-e]azepin-4-one Example 94 was prepared in the same manner as Example 93 using Intermediate 5 (53 mg, 0.2 mmol), Intermediate 43 (100 mg, 0.39 mmol), sodium tert-butoxide (47 mg, 0.49 mmol) and dichloro(1,1'-bis(di-tert-butylphosphino)ferrocene)palladium (13 mg, 0.02 mmol) in toluene (1 mL) heated to 140° C. under microwave irradiation for 1 h. Purification by prep HPLC gave the title compound (68 mg, 76%) as a brown solid. OH (CDCl$_3$) 1.09 (6H, s), 2.22 (3H, s), 2.82 (2H, s), 3.10 (2H, d, J 5.3 Hz), 3.98 (3H, s), 4.11-4.16 (2H, m), 4.30-4.34 (2H, m), 5.84-5.89 (1H, m), 6.80 (1H, dd, J 8.5, 0.4 Hz), 6.86 (1H, s), 7.55 (1H, dd, J 8.5, 2.4 Hz), 7.71 (1H, s), 8.13 (1H, d, J 1.9 Hz). LCMS (ES+) 451.20 (M+H)$^+$.

Example 95

2-{6-[1-(2-Hydroxyethyl)-1H-pyrazol-4-yl]-7-methyl-2,3-dihydro-4H-1,4-benzoxazin-4-yl}-7,7-dimethyl-5,6,7,8-tetrahydro-4H-[1,3]thiazolo[5,4-c]azepin-4-one A mixture of Intermediate 5 (37 mg, 0.13 mmol), Intermediate 44 (70 mg, 0.27 mmol), sodium tert-butoxide (32 mg, 0.24 mmol) and dichloro(1,1'-bis(di-tert-butylphosphino)ferrocene)palladium (9 mg, 0.013 mmol) in toluene (1 mL) was heated to 140° C. under microwave irradiation for 1 h, then cooled to r.t. and concentrated in vacuo. The residue was purified by prep HPLC then dissolved in DCM (15 mL), washed with saturated aqueous bicarbonate solution and the organic fraction was concentrated in vacuo to give the title compound (33 mg, 57%) as a brown solid. $\delta_H$ (CDCl$_3$) 1.10 (6H, s), 2.33 (3H, s), 2.83 (2H, s), 3.11 (2H, d, J 4.9 Hz), 3.18-3.25 (1H, m), 4.04-4.11 (2H, m), 4.12-4.16 (2H, m), 4.26-4.32 (4H, m), 5.81-5.86 (1H, m), 6.83 (1H, s), 7.51 (1H, s), 7.61 (1H, s), 7.78 (1H, s). LCMS (ES+) 454.22 (M+H)$^+$.

Example 96

2-{6-[1-(2-Hydroxy-2-methylpropyl)-1H-pyrazol-4-yl]-2,3-dihydro-4H-1,4-benzoxazin-4-yl}-5,5-dimethyl-5,6-dihydro-1,3-benzothiazol-7(4H-one A mixture of Example 1 (0.20 g, 0.5 mmol), Intermediate 33 (0.20 g, 0.76 mmol), potassium phosphate (0.15 g, 0.71 mmol), tetra-n-butylammonium bromide (16 mg, 0.05 mmol), palladium acetate (57 mg, 0.25 mmol) and triphenylphosphine (20 mg, 0.076 mmol) in DME (4 mL) and water (1 mL) was heated to 120° C. under microwave irradiation for 1 h. Further portions of Intermediate 33 (0.13 g, 0.5 mmol) and tetrakis(triphenylphosphine)palladium(0) (29 mg, 0.02 mmol) were added and heating to 120° C. under microwave irradiation continued for a further 1 h. After cooling to r.t. the mixture was filtered through celite. The filtrate was washed with water and brine, concentrated in vacuo and purified by chromatography (SiO$_2$, gradient elution 100% heptane—100% EtOAc) followed by prep HPLC to give the title compound (66 mg, 29%) as a white solid. $\delta_H$ (CDCl$_3$) 1.16 (6H, s), 1.21 (6H, s), 2.44 (2H, s), 2.77 (2H, s), 3.88 (1H, s), 4.11 (2H, s), 4.20-4.28 (2H, m), 4.31-4.39 (2H, m), 6.97 (1H, d, J 8.5 Hz), 7.20 (1H, dd, J 8.5, 2.1 Hz), 7.62 (1H, s), 7.77 (1H, s), 8.01 (1H, d, J 2.1 Hz). LCMS (ES+) 453 (M+H)$^+$.

The invention claimed is:

1. A compound of formula (I), or a pharmaceutically acceptable salt thereof:

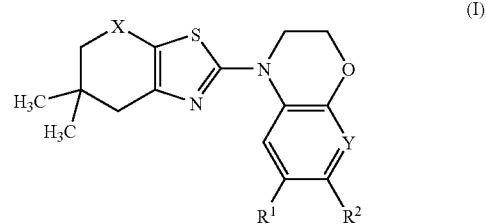

(I)

wherein
—X— represents a group of formula (b):

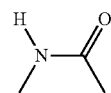

(b)

Y represents CH or N;
R$^1$ and R$^2$ independently represent hydrogen, halogen, nitro, hydroxy, C$_{1-6}$ alkyl, optionally substituted aryl, optionally substituted heteroaryl, —NR$^a$R$^b$, —CONR$^a$R$^b$, —NR$^a$COR$^c$, —N(COR$^c$)$_2$, —NR$^a$SO$_2$R$^c$, —CO$_2$R$^d$ or —OR$^e$;

R$^a$ represents hydrogen, C$_{1-6}$ alkyl or heteroaryl; and

R$^b$ represents hydrogen; or C$_{1-6}$ alkyl, aryl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^a$ and R$^b$, when taken together with the nitrogen atom to which they are both attached, represent optionally substituted C$_{3-7}$ heterocycloalkyl;

R$^c$ represents C$_{1-6}$ alkyl, aryl or heteroaryl, any of which groups may be optionally substituted by one or more substituents;

R$^d$ represents C$_{1-6}$ alkyl; and

R$^e$ represents optionally substituted heteroaryl, wherein said optional substituents on R$^1$, R$^2$, R$^b$ or R$^c$, or on the cyclic moiety —NR$^a$R$^b$, are selected from the group consisting of halogen, C$_{1-6}$ alkyl, C$_{1-6}$ alkoxy, di(C$_{1-6}$)alkylamino, C$_{2-6}$ alkoxycarbonyl, hydroxy(C$_{1-6}$)alkyl, hydroxy(C$_{1-6}$)alkylamino, hydroxy-[(C$_{1-6}$)alkoxy](C$_{1-6}$)alkyl and C$_{1-6}$ alkoxy(C$_{2-6}$)alkenyl, and wherein said optional substituents on R$^c$ are selected from the group consisting of C$_{1-6}$ alkyl and heterocycloalkyl.

2. A compound as claimed in claim 1, wherein Y represents CH.

3. A compound as claimed in claim 1, wherein R$^1$ represents optionally substituted heteroaryl.

4. A compound as claimed in claim 3, wherein R$^2$ represents hydrogen or C$_{1-6}$ alkyl.

5. A compound as claimed in claim 1 represented by formula (IIA), or a pharmaceutically acceptable salt thereof:

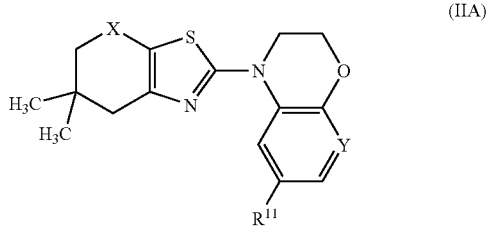

(IIA)

wherein

R$^{11}$ represents halogen, nitro, hydroxy, optionally substituted aryl, optionally substituted heteroaryl, —NR$^a$R$^b$ or —OR$^e$; and —X—, Y, R$^a$ and R$^b$ are as defined in claim 1.

6. A compound as claimed in claim 1 represented by formula (IIB), or a pharmaceutically acceptable salt thereof:

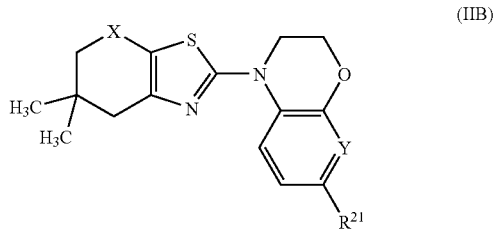

(IIB)

wherein

R$^{21}$ represents halogen, nitro, optionally substituted aryl, optionally substituted heteroaryl, —NR$^a$R$^b$, —CONR$^a$R$^b$, —NR$^a$COR$^c$, —N(COR$^c$)$_2$, —NR$^a$SO$_2$R$^c$ or —CO$_2$R$^d$; and —X—, Y, R$^a$, R$^b$, R$^c$ and R$^d$ are as defined in claim 1.

7. A compound as claimed in claim 1 represented by formula (IIC), or a pharmaceutically acceptable salt thereof:

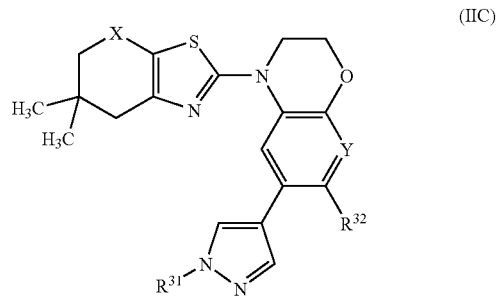

(IIC)

wherein

R$^{31}$ represents hydrogen, C$_{1-6}$ alkyl, hydroxy(C$_{1-6}$)alkyl or hydroxy[(C$_{1-6}$)alkoxy]-(C$_{1-6}$)alkyl;

R$^{32}$ represents hydrogen or C$_{1-6}$ alkyl; and

—X and —Y are as defined in claim 1.

8. A compound as claimed in claim 1, selected from the following:

7,7-Dimethyl-2-(7-nitro-2,3-dihydrobenzo[1,4]oxazin-4-yl)-5,6,7,8-tetrahydro-thiazolo[5,4-c]azepin-4-one, 7,7-Dimethyl-2-(6-hydroxy-2,3-dihydrobenzo[1,4]oxazin-4-yl)-5,6,7,8-tetrahydro-thiazolo[5,4-c]azepin-4-one, 7,7-Dimethyl-2-[6-(6-methylpyridin-3-yl)-2,3-dihydrobenzo[1,4]oxazin-4-yl]-5,6,7,8-tetrahydrothiazolo[5,4-c]azepin-4-one, 7,7-Dimethyl-2-[6-(1-methyl-1H-pyrazol-4-yl)-2,3-dihydrobenzo[1,4]oxazin-4-yl]-5,6,7,8-tetrahydrothiazolo[5,4-c]azepin-4-one, 2-(6-Bromo-2,3-dihydro-4H-1,4-benzoxazin-4-yl)-7,7-dimethyl-5,6,7,8-tetrahydro-4H-[1,3]thiazolo[5,4-c]azepin-4-one, 2-(7-Bromo-2,3-dihydro-4H-1,4-benzoxazin-4-yl)-7,7-dimethyl-5,6,7,8-tetrahydro-4H-[1,3]thiazolo[5,4-c]azepin-4-one, 2-(6-Amino-2,3-dihydro-4H-1,4-benzoxazin-4-yl)-7,7-dimethyl-5,6,7,8-tetrahydro-4H-[1,3]thiazolo[5,4-c]azepin-4-one, 7,7-Dimethyl-2-(6-pyridazin-3-yl-2,3-dihydro-4H-1,4-benzoxazin-4-yl)-5,6,7,8-tetrahydro-4H-[1,3]thiazolo[5,4-c]azepin-4-one, 2-{6-[1-(2-Hydroxy-2-methyl-propyl)-1H-pyrazol-4-yl]-2,3-dihydro-benzo[1,4]oxazin-4-yl}-7,7-dimethyl-5,6,7,8-tetrahydro-thiazolo[5,4-c]azepin-4-one, 2-{6-[1-(2-Hydroxy-3-methoxypropyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one, 7,7-Dimethyl-2-[6-(6-methyl-1-oxidopyridin-3-yl)-2,3-dihydro-4H-1,4-benzoxazin-4-yl]-5,6,7,8-tetrahydro-4H-[1,3]thiazolo[5,4-c]azepin-4-one, 2-{6-[1-(2,3-Dihydroxypropyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one, 2-[6-(1,2-Dimethyl-1H-imidazol-5-yl)-2,3-dihydro-4H-1,4-benzoxazin-4-yl]-7,7-dimethyl-5,6,7,8-tetrahydro-4H-[1,3]thiazolo[5,4-c]azepin-4-one, 2-{6-[1-(2-Hydroxyethyl)-1H-pyrazol-4-yl]-2,3-dihydro-4H-1,4-benzoxazin-4-yl}-7,7-dimethyl-5,6,7,8-tetrahydro-4H-[1,3]thiazolo[5,4-c]azepin-4-one, 7,7-Dimethyl-2-{6-[(6-methylpyridazin-3-yl)amino]-2,3-dihydro-4H-1,4-benzoxazin-4-yl}-5,6,7,8-tetrahydro-4H-[1,3]thiazolo[5,4-c]azepin-4-one acetate salt, 2-[6-({6-[(E)-2-Methoxyvinyl]pyridin-2-yl} amino)-2,3-dihydro-4H-1,4-benzoxazin-4-yl]-7,7-dimethyl-5,6,7,8-tetrahydro-4H-[1,3]thiazolo[5,4-c]azepin-4-one, 7,7-Dimethyl-2-(7-pyrrolidin-1-yl-2,3-dihydro-4H-1,4-benzoxazin-4-yl)-5,6,7,8-tetrahydro-4H-[1,3]thiazolo[5,4-c]azepin-4-one, 7,7-Dimethyl-2-[7-methyl-6-(1-methyl-1H-pyrazol-4-yl)-2,3-dihydro-4H-1,4-benzoxazin-4-yl]-5,6,7,8-tetrahydro-4H-[1,3]thiazolo[5,4-c]azepin-4-one, 2-[6-(6-Methoxypyridin-3-yl)-7-methyl-2,3-dihydro-4H-1,4-benzoxazin-4-yl]-7,7-dimethyl-5,6,7,8-tetrahydro-4H-[1,3]thiazolo[5,4-c]azepin-4-one, 2-{6-[1-(2-Hydroxyethyl)-1H-pyrazol-4-yl]-7-methyl-2,3-dihydro-4H-1,4-benzoxazin-4-yl}-7,7-dimethyl-5,6,7,8-tetrahydro-4H-[1,3]thiazolo[5,4-c]azepin-4-one, or a pharmaceutically acceptable salt of any of the foregoing.

9. A pharmaceutical composition comprising a compound of formula (I) as defined in claim 1, or a pharmaceutically acceptable salt thereof, in association with a pharmaceutically acceptable carrier.

10. A compound as claimed in claim 2, wherein $R^1$ represents optionally substituted heteroaryl.

11. The compound of claim 1 wherein $R^1$ represents hydrogen and $R^2$ represents other than hydrogen.

12. The compound of claim 1 wherein $R^1$ represents other than hydrogen and $R^2$ represents hydrogen.

13. The compound of claim 1 wherein $R^1$ represents other than hydrogen and $R^2$ represents methyl.

14. A method for the treatment of rheumatoid arthritis, multiple sclerosis, asthma, inflammatory bowel disease, psoriasis, transplant rejection, thrombosis, cardiac hypertrophy, hypertension, irregular contractility of the heart; Parkinson's disease, Huntington's disease, stroke, amyotrophic lateral sclerosis, spinal cord injury, head trauma, seizures, obesity, type 2 diabetes, leukaemia, glioblastoma, lymphoma, melanoma, cancers of the liver, bone, skin, brain, pancreas, lung, breast, stomach, colon, rectum, prostate, ovary and cervix; pain, and age-related macular degeneration (ARMD), the method comprising administering to a patient in need of such treatment an effective amount of a compound of formula (I) as defined in claim 1, or a pharmaceutically acceptable salt thereof.

* * * * *